US007968287B2

(12) United States Patent
Griffiths et al.

(10) Patent No.: US 7,968,287 B2
(45) Date of Patent: Jun. 28, 2011

(54) IN VITRO EVOLUTION IN MICROFLUIDIC SYSTEMS

(75) Inventors: Andrew Griffiths, Strasbourg (FR); David Weitz, Cambridge, MA (US); Keunho Ahn, San Diego, CA (US); Darren R. Link, Lexington, MA (US); Jerome Bibette, Paris (FR)

(73) Assignee: Medical Research Council Harvard University, Cambridge, MA (US)

( * ) Notice: Subject to any disclaimer, the term of this patent is extended or adjusted under 35 U.S.C. 154(b) by 1292 days.

(21) Appl. No.: 10/961,695

(22) Filed: Oct. 8, 2004

(65) Prior Publication Data

US 2006/0078888 A1    Apr. 13, 2006

(51) Int. Cl.
*C12Q 1/68* (2006.01)
(52) U.S. Cl. ............................. 435/6; 435/180; 435/375
(58) Field of Classification Search .................. None
See application file for complete search history.

(56) References Cited

U.S. PATENT DOCUMENTS

| | | | |
|---|---|---|---|
| 5,512,131 A | 4/1996 | Kumar et al. | |
| 5,733,526 A | 3/1998 | Trevino et al. | 424/9.52 |
| 5,783,431 A | 7/1998 | Peterson et al. | |
| 5,858,670 A | 1/1999 | Lam et al. | |
| 5,904,933 A | 5/1999 | Riess et al. | |
| 5,942,056 A | 8/1999 | Singh | |
| 6,103,537 A | 8/2000 | Ullman et al. | |
| 6,116,516 A | 9/2000 | Ganan-Calvo | |
| 6,120,666 A | 9/2000 | Jacobson et al. | |
| 6,124,439 A | 9/2000 | Friedman et al. | |
| 6,165,778 A | 12/2000 | Kedar | |
| 6,187,214 B1 | 2/2001 | Ganan-Calvo | |
| 6,210,896 B1* | 4/2001 | Chan | 435/6 |
| 6,221,654 B1 | 4/2001 | Quake et al. | |
| 6,248,378 B1 | 6/2001 | Ganan-Calvo | |
| 6,251,661 B1 | 6/2001 | Urabe et al. | |
| 6,268,222 B1 | 7/2001 | Chandler et al. | |
| 6,344,325 B1 | 2/2002 | Quake et al. | |
| 6,355,198 B1 | 3/2002 | Kim et al. | |
| 6,475,441 B1 | 11/2002 | Parce et al. | |
| 6,489,103 B1* | 12/2002 | Griffiths et al. | 435/6 |
| 6,508,988 B1 | 1/2003 | Van Dam et al. | |
| 6,540,895 B1* | 4/2003 | Spence et al. | 204/450 |
| 6,680,178 B2 | 1/2004 | Harris et al. | 435/23 |
| 6,766,817 B2 | 7/2004 | Da Silva | |
| 6,808,882 B2 | 10/2004 | Griffiths et al. | |
| 6,833,242 B2 | 12/2004 | Quake et al. | |
| 6,918,404 B2 | 7/2005 | Dias da Silva | |
| 7,066,586 B2 | 6/2006 | Da Silva | |
| 7,081,192 B1 | 7/2006 | Wang et al. | 204/547 |
| 7,138,233 B2 | 11/2006 | Griffiths et al. | |
| 7,252,943 B2 | 8/2007 | Griffiths et al. | |
| 7,294,503 B2 | 11/2007 | Quake et al. | 435/288.5 |
| 7,378,280 B2 | 5/2008 | Quake et al. | 436/63 |
| 7,514,210 B2 | 4/2009 | Holliger et al. | |
| 7,541,383 B2 | 6/2009 | Fu et al. | 514/602 |
| 7,718,578 B2* | 5/2010 | Griffiths et al. | 506/23 |
| 2001/0023078 A1 | 9/2001 | Bawendi et al. | |
| 2001/0041343 A1 | 11/2001 | Pankowsky | |
| 2001/0041344 A1 | 11/2001 | Sepetov et al. | |
| 2002/0005354 A1 | 1/2002 | Spence et al. | |
| 2002/0022261 A1 | 2/2002 | Anderson et al. | |
| 2002/0036139 A1 | 3/2002 | Becker et al. | |
| 2002/0058332 A1 | 5/2002 | Quake et al. | |
| 2002/0164271 A1 | 11/2002 | Ho | |
| 2003/0148544 A1 | 8/2003 | Nie et al. | |
| 2004/0068019 A1 | 4/2004 | Higuchi et al. | |
| 2005/0084923 A1 | 4/2005 | Mueller et al. | |
| 2006/0147909 A1 | 7/2006 | Rarbach et al. | |
| 2007/0003442 A1* | 1/2007 | Link et al. | 422/99 |

FOREIGN PATENT DOCUMENTS

| | | |
|---|---|---|
| WO | WO 84/02000 | 5/1984 |
| WO | WO 96/29629 | 9/1996 |
| WO | WO 99/02671 | 1/1999 |
| WO | WO 00/40712 | 7/2000 |
| WO | WO 01/89789 | 11/2001 |
| WO | WO 02/22869 | 3/2002 |
| WO | WO 02/23163 | 3/2002 |
| WO | WO 02/097130 | 12/2002 |
| WO | WO 02/103011 | 12/2002 |
| WO | WO 03/025113 | 3/2003 |
| WO | WO 2004/002627 | 1/2004 |
| WO | WO 2004/024917 | 3/2004 |
| WO | WO 2004/071638 | 8/2004 |
| WO | WO 2004/087308 | 10/2004 |
| WO | WO 2004/088314 | 10/2004 |
| WO | WO 2004/091763 | 10/2004 |
| WO | WO 2005/021151 | 3/2005 |
| WO | WO 2006/038035 | 4/2006 |
| WO | WO 2006/040551 | 4/2006 |
| WO | WO 2006/040554 | 4/2006 |
| WO | WO 2006/096571 | 9/2006 |
| WO | WO 2007/089541 | 8/2007 |

OTHER PUBLICATIONS

Song et al., J. Am. Chem. Soc. (2003) vol. 125, pp. 14613-14619.*
Adang, A.E., and Hermkens, P.H. (2001). The contribution of combinatorial chemistry to lead generation: an interim analysis. *Curr Med Chem* 8, 985-998.
Atwell, S. & Wells, J.A. (1999). Selection for Improved Subtiligases by Phage Display; *Proc. Natl. Acad. Sci.* USA 96, 9497-9502.
Bass, S., Greene, R. and Wells, J.A. (1990). Hormone Phage: An Enrichment Method for Variant Proteins With Altered Binding Properties; *Proteins*, 8, 309-14.
Burbaum, J. (1998). Miniaturization technologies in HTS: how fast, how small, how soon? *Drug Discov Today* 3, 313-322.
Chapman, K.B. and Szostak, J.W. (1994). In Vitro Selection of Catalytic RNAs; *Curr. op. in Struct. Biol.*, 4, 618-622.
Cull, M.G., Miller, J.F. and Schatz, P.J. (1992). Screening for Receptor Ligands Using Large Libraries of Peptides Linked to the C Terminus of the Lac Repressor; *Proc Natl Acad Sci U S A*, 89, 1865-9.
Demartis, et al. (1999). A Strategy for the Isolation of Catalytic Activities from Repertoires of Enzymes Displayed on Phase; *J. Mol. Biol.* 286, 617-633.

(Continued)

*Primary Examiner* — Jim Ketter
(74) *Attorney, Agent, or Firm* — Brown Rudnick LLP

(57) ABSTRACT

The invention describes a method for isolating one or more genetic elements encoding a gene product having a desired activity, comprising the steps of: (a) compartmentalising genetic elements into microcapsules; and (b) sorting the genetic elements which express the gene product having the desired activity; wherein at least one step is under microfluidic control. The invention enables the in vitro evolution of nucleic acids and proteins by repeated mutagenesis and iterative applications of the method of the invention.

5 Claims, 33 Drawing Sheets

OTHER PUBLICATIONS

Ellington, A.D. and Szostak, J.W. (1990); In Vitro Selection of RNA Molecules that Bind Specific Ligands *Nature*, 346, 818-822.

Ganan-Calvo, Generation of Steady Liquid Microthreads and Micron-Sized Monodisperse Sprays and Gas Streams, *Phys. Rev. Lett.*, 80:2, Jan. 12, 1998, 285-288.

Gold, L., Polisky, B., Uhlenbeck, 0. and Yarus, M. (1995). Diversity of Oligonucleotide Functions; *Annu Rev Biochem*. 64. 763-97.

Green, R. and Szostak, J.W.; Selection of a Ribozyme That Functions as a Superior Template in a Self-Copying Reaction (1992); *Science*, 258, 1910-5.

Hanes, J. & Pluckthun, A. (1997). In vitro selection and evolution of functional proteins by using ribosome display. *Proc. Natl. Acad. Sci. USA* 94, 4937-4942.

Hergenrother, P.J., Depew, K.P., and Schreiber, S.L. (2000). Small-molecule microarrays: covalent attachment and screening of alcohol-containing small molecules on glass slides. *J Am Chem Soc* 122, 7849-7850.

Janda, et al. (1997). In Vitro Selection and Evolution of Functional Proteins by Using Ribosome Display; *Science*, 275, 945-948.

Jestin, J.-L., Kristensen, P. & Winter, G. (1999). A Method for the Selection of Catalytic Activity Using Phage Display and Proximity Coupling; *Angew. Chem. Int. Ed. Engl.* 38, 1124-1127.

Joyce, G.F. (1994). In Vitro Evolution of Nucleic Acids; *Curr. op. Structural Biol.*, 4, 331-336.

Lyne, P.D. (2002). Structure-based virtual screening: an overview. *Drug Discov Today* 7, 1047-1055.

Mattheakis, L.C., Bhatt, R.R. and Dower, W.J. (1994); An in vitro polysome display system for identifying ligands from very large peptide libraries; *Proc Natl Acad Sci U S A*, 91, 9022-6.

McCafferty, et al. (1990); Phage antibodies: filamentous phage displaying antibody variable domains; *Nature*, 348, 552-4.

Nemoto, N., Miyamoto-Sato, E., Husimi, Y. and Yanagawa, H. (1997). In vitro virus: Bonding of mRNA bearing puromycin at the 3'-terminal end to the C-terminal end of its encoded protein on the ribosome in vitro. *FEBS Letters* 414, 405-408.

Parmley, S.F. and Smith, G.P. (1988); Antibody-selectable filamentous fd phage vectors: affinity purification of target genes; *Gene*, 73, 305-18.

Pedersen, et al. (1998). A Method for Directed Evolution and Functional Cloning of Enzymes; *Proc. Natl. Acad. Sci.* USA 95, 10523-10528.

Ramstrom, O., and Lehn, J.M. (2002). Drug discovery by dynamic combinatorial libraries. *Nat Rev Dru: Discov* 1, 26-36.

Roberts, R.W. & Szostak, J.W. (1997). RNA-peptide fusions for the in vitro selection of peptides and roteins. *Proc. Natl. Acad. Sci. USA* 94, 12297-12302.

Soumillion, et al. (1994); Selection of β-Lactamase on Filamentous Bacteriophage by Catalytic Activity; *J Mol Biol*, 237, 415-22.

Tawfik, D. S., and Griffiths, A. D. (1998). Man-made cell-like compartments for molecular evolution. *Nat Biotechnol* 16, 652-656.

Thorsen, et al., Dynamic Pattern Formation in a Vesicle-Generating Microfluidic Device, *Phys. Rev. Lett.*, 86:18, Apr. 30, 2001.

Tuerk, C. and Gold, L. (1990); Systematic Evolution of Ligands by Exponential Enrichment: RNA Ligands to Bacteriophage T4 DNA Polymerase; *Science*, 249, 505-10.

Aharoni et al., "High-throughput screens and selections of enzyme-encoding genes", *Curr. Opin. Chem. Biol.* 9(2): 210-6 (2005).

Arkin, M.R., and Wells, J.A., "Probing the importance of second sphere residues in an esterolytic antibody by phage display", *J Mol Biol* 284(4): 1083-94 (1998).

Beebe et al., "Functional hydrogel structures for autonomous flow control inside microfluidic channels", *Nature*, 404: 588-590 (2000).

Bernath et al., "In Vitro Compartmentalization by Double Emulsions: Sorting and Gene Enrichment by Fluorescence Activated Cell Sorting", *Anal. Biochem.*, 325: 151-157 (2004).

Bernath et al., "Directed evolution of protein inhibitors of DNA-nucleases by in vitro compartmentalization (IVC) and nano-droplet delivery", *J. Mol. Biol.* 345(5): 1015-26 (2005).

Boder, E.T. and Wittrup, K.D., "Yeast surface display for screening combinatorial polypeptide libraries", *Nat Biotechnol* 15(6): 553-7 (1997).

Calvert, P., "Inkjet printing for materials and devices", *Chem. Mater.*, 13: 3299-3305 (2001).

Chen-Goodspeed et al., "Structural determinants of the substrate and stereochemical specificity of phosphotriesterase", *Biochemistry* 40(5): 1325-31 (2001).

Chiu et al., "Chemical transformations in individual ultrasmall biomimetic containers", *Science*, 283: 1892-1895 (1999).

Curran, D.P., "Strategy-Level Separations in Organic Synthesis: From Planning to Practice", *Angew. Chem. Int. Ed.*, 37: 1174-1196 (1998).

Czarnik, A.W., "Encoding Methods for Combinatorial Chemistry", *Curr. Opin. Chem. Biol.*, 1: 60-66 (1997).

Davis et al., "Multiple Emulsions as Targetable Delivery Systems",*Meth. Enzymol.*, 149: 51-64 (1987).

de Gans, et al., "Inkjet printing of polymers: state of the art and future developments",*Advanced Materials*, 16: 203-213 (2004).

Dickinson, E., "Emulsions and Droplet Size Control", in Wedlock, D.J. (ed.), *Controlled Particle, Droplet and Bubble Formulation*, Butterworth-Heinemann, Oxford, Chapter 7, pp. 191-216 (1994).

Dittrich et al., "A new embedded process for compartmentalized cell-free protein expression and on-line detection in microfluidic devices", *Chembiochem* 6(5): 811-4 (2005).

Doi, N. and Yanagawa, "H. Stable: protein-DNA fusion system for screening of combinatorial protein libraries in vitro", *FEBS Lett.*, 457: 227-230 (1999).

Doi et al., In vitro selection of restriction endonucleases by in vitro compartmentalization. *Nucleic Acids Res.* 32(12): e95 (2004).

Dömling A., "Recent advances in isocyanide-based multicomponent chemistry", *Curr Opin Chem Biol.*, 6(3): 306-13 (2002).

Dömling A. and Ugi 1.1., "Multicomponent Reactions with Isocyanides",*Angew Chem Int Ed Engl.*, 39(18): 3168-3210 (2000).

Dubertret et al., "In Vivo Imaging of Quantum Dots Encapsulated in Phospholipid Micelles", Science, 298: 1759-1762 (2002).

Duffy et al., "Rapid Prototyping of Microfluidic Systems and Polydimethylsiloxane",*Anat. Chem.*, 70: 474-480 (1998).

Ellington, A.D. and Szostak, J.W., "In Vitro Selection of RNA Molecules that Bind Specific Ligands", *Nature*, 346: 818-822 (1990).

Fastrez, J., "In vivo versus in vitro screening or selection for catalytic activity in enzymes and abzymes",*Mol Biotechnol* 7(1): 37-55 (1997).

Fields, S. and Song, O., "A novel genetic system to detect protein-protein interactions", *Nature* 340(6230): 245-6 (1989).

Finch, C.A., "Industrial Microencapsulation: Polymers for Microcapsule Walls", *Encapsulation and Controlled Release. Spec. Publ. -R. Soc. Chem.*, pp. 1-12 (1993).

Fu et al., "An Integrated Microfabricated Cell Sorter", *Anal. Chem.*, 74: 2451-2457 (2002).

Fulton. et al., "Advanced Multiplexed Analysis with the FlowMetrik™ System", *Clin. Chem.*, 43: 1749-1756 (1997).

Georgiou, et al., "Display of heterologous proteins on the surface of microorganisms: from the screening of combinatorial libraries to live recombinant vaccines", *Nat Biotechnol* 15(1): 29-34 (1997).

Ghadessy et al, "Directed Evolution of Polymerase Function by Compartmentalized Self-Replication", *Proc. Natl. Acad. Sci USA*, 98(8): 4552-4557 (2001).

Gibbs et al., "Detection of single DNA base differences by competitive oligonucleotide priming",*Nucleic Acids Res.* 17(7): 2437-48 (1989).

Gordon et al., "Solid Phase Synthesis—Designer Linkers for Combinatorial Chemistry: A Review",*J. Chem. Technol. Biotechnol.*, 74: 835-851 (1999).

Griffiths et al., "Isolation of High Affinity Human Antibodies Directly from Large Synthetic Repertoires", *EMBO. J.*, 13(14): 3245-3260 (1994).

Griffiths, A.D., and Tawfilc D.S., "Man-made enzymes—from design to in vitro compartmentalization", *Curr. Opin. Biotechnol.* 11(4): 338-53 (2000).

Griffiths et al., "Directed Evolution of an Extremely Fast Phosphotriesterase by In Vitro Compartmentalization", *EMBO. J.*, 22(1):24-35 (2003).

Guixe et al., "Ligand-Induced Conformational Transitions in *Escherichia coli* Phosphofructokinase 2: Evidence for an Allosteric Site for MgATP$^{2-}$", *Biochem.*, 37: 13269-12375 (1998).

Hai, M. and Magdassi, S., "Investigation on the release of fluorescent markers from w/o/w emulsions by fluorescence-activated cell sorter", *J. Control Release* 96(3): 393-402 (2004).

Han et al., "Quantum-dot-tagged Microbeads for Multiplexed Optical Coding of Biomolecules", *Nat. Biotechnol.*, 19(7): 631-635 (2001).

Handen, J. S., "High-Throughput Screening-Challenges for the Future", *Drug Discov. World*, pp. 47-50 (2002).

Heim et al., "Engineering Green Fluorescent Protein for Improved Brightness, Longer Wavelengths and Fluorescence Response Energy Transfer", *Curr. Biol.*, 6(2): 178-182 (1996).

Hildebrand et al., "Liquid-Liquid Solubility of Perfluoromethylcyclohexane with Benzene, Carbon Tetrachloride, Chlorobenzene, Chloroform and Toluene", *J. Am. Chem. Soc.*, 71: 22-25 (1949).

Holmes et al., "Reagents for Combinatorial Organic Synthesis: Development of a New O-Nitrobenzyl Photolabile Linder for Solid Phase Synthesis",*J. Org Chem.*, 60: 2318-2319 (1995).

Jermutus, et al., "Recent advances in producing and selecting functional proteins by using cell-free translation", *Curr Opin Biotechnol* 9(5): 534-48 (1998).

Joerger et al., "Analyte detection with DNA-labeled antibodies and polymerase chain reaction", *Clin. Chem.* 41(9): 1371-7 (1995).

Johannsson, A., "Heterogeneous Enzyme Immunoassays", *In Principles and Practice of Immunoassay*, pp. 295-325 (1991).

Johannsson et al., "Amplification by Second Enzymes", In *ELISA and Other Solid Phase Immunoassays*. Kemeny et al (ed.). Chapter 4. pp. 85-106 (1988).

Keij et al., "High-Speed Photodamage Cell Selection Using a Frequency-Doubled Argon Ion Laser", *Cytometry*, 19(3): 209-216 (1995).

Kerker, M., "Elastic and Inelastic Light Scattering in Flow Cytometry$^{1,2-1}$" *Cytometry*, 4(1): 1-10 (1983).

Klug, S.J., and Famulok, M., "All you wanted to know about SELEX", *Mol. Biol. Rep.* 20(2): 97-107 (1994).

Krafft et al., "Emulsions and Microemulsions with a Fluorocarbon Phase", *Curr. Op. Colloid Interface Sci.*, 8: 251-258 (2003).

Lee et al., "Investigating the target recognition of DNA cytosine-5 methyltransferase HhaI by library selection using in vitro compartmentalisation (IVC)", *Nucleic Acids Res.*, 30: 4937-4944 (2002).

Lim et al., "Microencapsulated islets as bioartificial endocrine pancreas." *Science, New Series*, 210(4472): 908-910 (1980).

Link et al., "Geometrically Mediated Breakup of Drops in Microfluidic Devices",*Phys. Rev. Lett.*, 92(5): 054503-1 thru 054503-4 (2004).

Link et al., "Electric control droplets in microfluidic devices." *Angew. Chem. Int. Ed.*, 45: 2556-2560 (2006).

Lipinski et al., "Experimental and Computational Approaches to Estimate Solubility and Permeability in Drug Discovery and Development Settings",*Adv. Drug Deliv. Rev.*, 46: 3-26 (2001).

Lorenz et al., "Isolation and expression of a cDNA encoding Renilla reniformis luciferase", *Proc Natl Acad Sci U S A.* 88(10): 4438-42 (1991).

Lowe, K. C., "Perfluorochemical Respiratory Gas Carriers: Benefits to Cell Culture Systems",*J. Fluorine Chem.*, 118: 19-26 (2002).

Luisi et al., "Activity and Conformation of Enzymes in Reverse Micellar Solutions",*Meth. Enzymol.*, 136: 188-216 (1987).

Mackenzie et al., "The Application of Flow Microfluorimetry to Biomedical Research and Diagnosis: A Review", *Dev. Biol. Stand.*, 64: 181-193 (1986).

Mahajan et al., "Bcl-2 and Bax Interactions in Mitochondria Probed with Green Florescent Protein and Fluorescence Resonance Energy Transfer", *Nat. Biotechnol.* 16(6): 547-552 (1998).

Mastrobattista et al., "High-throughput screening of enzyme libraries: in vitro evolution of a beta-galactosidase by fluorescence-activated sorting of double emulsions", *Chem. Biol.* 12(12): 1291-300 (2005).

Masui et al., "Probing of DNA-Binding Sites of *Escherichia coli* RecA Protein Utilizing 1-anilinonaphthalene-8-Sulfonic Acid", *Biochem.*, 37(35): 12133-12143 (1998).

McDonald, J. C. and Whitesides, G. M. "Poly(dimethylsiloxane) as a material for fabricating microfluidic devices", *Acc. Chem. Res.*, 35: 491-499 (2002).

Minshull, J. and Stemmer, W.P., "Protein evolution by molecular breeding", *Curr Opin Chem Biol* 3(3): 284-90 (1999).

Miyawaki et al., "Fluorescent Indicators for Ca2+ Based on Green Fluorescent Proteins and Calmodulin", *Nature*, 388: 882-887 (1997).

Mize et al., "Dual-enzyme cascade—an amplified method for the detection of alkaline phosphatase", *Anal. Biochem.* 179(2): 229-35 (1989).

Nisisako et al., "Formation of droplets using branch channels in a microfluidic circuit", *Proceedings of the SICE Annual Conference. International Session Papers* 1262-1264 (2002).

Norman, A., "Flow Cytometry", *Med. Phys.*, 7(6): 609-615 (1980).

Oberholzer et al., "Polymerase chain reaction in liposomes", *Chem. Biol.* 2(10): 677-82 (1995).

Okushima et al. "Controlled production of monodisperse double emulsions by two-step droplet breakup in microfluidic devices", *Langmuir* 20(23): 9905-8 (2004).

Olsen, et al., "Function-based isolation of novel enzymes from a large library", *Nat Biotechnol* 18(10): 1071-4 (2000).

Ostermeier, el al., "A combinatorial approach to hybrid enzymes independent of DNA homology",*Nat Biotechnol* 17(12): 1205-9 (1999).

Perelson, A.S., "Theoretical Studies of Clonal Selection: Minimal Antibody Repertoire Size and Reliability of Self-Non-Self Discrimination", *J. Theor. Biol.*, 81: 645-670 (1979).

Pirrung et al., "A General Method for the Spatially Defined Immobilization of Biomolecules on Glass Surfaces Using 'Caged' Biotin", *Bioconjug. Chem.*, 7: 317-321 (1996).

Pollack, et al., "Selective chemical catalysis by an antibody", *Science* 234(4783): 1570-3 (1986).

Qi et al., "Acid Beta-Glucosidase: Intrinsic Fluorescence and Conformational Changes Induced by Phospholipids and Saposin C", *Biochem.*, 37(33): 11544-11554 (1998).

Riess, J.G., "Fluorous Micro- and Nanophases with a Biomedical Perspective", *Tetrahedron*, 58: 4113-4131 (2002).

Roberts, R.W., "Totally in vitro protein selection using mRNA-protein fusions and ribosome display" *Curr Opin Chem Biol* 3(3): 268-73 (1999).

Roberts, R.W. and Ja, W.W., "In vitro selection of nucleic acids and proteins: What are we learning?", *Curr Opin Struct Biol* 9(4): 521-9 (1999).

Rolland et al., "Review Article: Fluorescence Polarization Assay by Flow Cytometry",*J. Immunol. Meth.*, 76(1): 1-10 (1985).

Sadtler et al., "Achieving Stable, Reverse Water-in-Fluorocarbon Emulsions", *Angew. Chem. Int. Ed. Engl.*, 35(17): 1976-1978 (1996).

Schatz, et al., "Screening of peptide libraries linked to lac repressor", *Methods Enzymol* 267: 171-91 (1996).

Scott, R.L., "The Solubility of Fluorocarbons", *J. Am. Chem. Soc.*, 70: 4090-4093 (1948).

Sepp et al., "Microbead Display by In Vitro Compartmentalisation: Selection for Binding Using Flow Cytometry", *FEBS Lett.*, 532: 455-458 (2002).

Shapiro H.M., "Multistation multiparameter flow cytometry: a critical review and rationale", *Cytometry* 3(4): 227-43 (1983).

Sims et al., "Immunopolymerase chain reaction using real-time polymerase chain reaction for detection", *Anal. Biochem.* 281(2): 230-2 (2000).

Smith G.P., "Filamentous fusion phage: novel expression vectors that display cloned antigens on the virion surface", *Science* 228(4705): 1315-7 (1985).

Smith, G.P. and Petrenko, V.A., "Phage display", *Chemical reviews* 97(2): 391-410 (1997).

Song et al., "A Microfluidic System for Controlling Reaction Networks in Time", Angew.*Chem. Int. Ed. Engl.*, 42(7): 767-772 (2003).

Song, H. and Ismagilov, R.F., "Millisecond kinetics on a microfluidic chip using nanoliters of reagents", *J Am Chem Soc.*, 125: 14613-14619 (2003).

Strizhkov et al., "PCR amplification on a microarray of gel-immobilized oligonucleotides: Detection of bacterial toxin- and drug-resistant genes and their mutations." *Biotechniques*, 29(4): 844-857 (2000).

Studer et al., "Fluorous Synthesis: A Fluorous-Phase Strategy for Improving Separation Efficiency in Organic Synthesis", *Science* 275: 823-826 (1997).

Sugiura et al., "Interfacial tension driven monodispersed droplet formation from microfabricated channel array" *Langmuir*, 17: 5562-5566 (2001).

Sundberg et al., "Spatially-Addressable Immobilisation of Macromolecules on Solid Supports", *J. Am. Chem. Soc.*, 117: 12050-12057 (1995).

Tramontano, et al., "Catalyic antibodies" *Science* 234(4783): 1566-70 (1986).

Umbanhowar et al., "Monodisperse Emulsions Generated Via Drop Break Off in a Coflowing Steam", *Langmuir*, 16: 347-351 (2000).

Venter, et al., "The sequence of the human genome", *Science* 291(5507): 1304-51 (2001).

Voss, E. W., "Kinetic Measurements of Molecular Interactions by Spectrofluorometry", *J. Mol. Recognition*, 6:51-58 (1993).

Warburton, B., "Microcapsules for Multiple Emulsions", *Encapsulation and Controlled Release, Spec. Publ.-R. Soc. Chem.*, pp. 35-51 (1993).

Wilson, D.S. and Szostak, J.W., "In vitro selection of functional nucleic acids", *Ann. Rev. Biochem.* 68: 611-647 (1999).

Yu et al., "Specific inhibition of PCR by non-extendable oligonucleotides using a 5' to 3' exonuclease-deficient DNA polymerase", *Biotechniques* 23(4): 714-6, 718-20 (1987).

Yonezawa et al., "DNA display for in vitro selection of diverse peptide libraries", *Nucleic Acids Research* 31(19):e118 (2003).

Tan et al., "Design of microfluidic channel geometries for the control of droplet volume, chemical concentration, and sorting", *Lab on a Chip*, 4:292-298 (2004).

Taniguchi et al., "Chemical Reactions in Microdroplets by Electrostatic Manipulation of Droplets in Liquid Media", *Lab on a Chip*, 2:19-23 (2002).

* cited by examiner

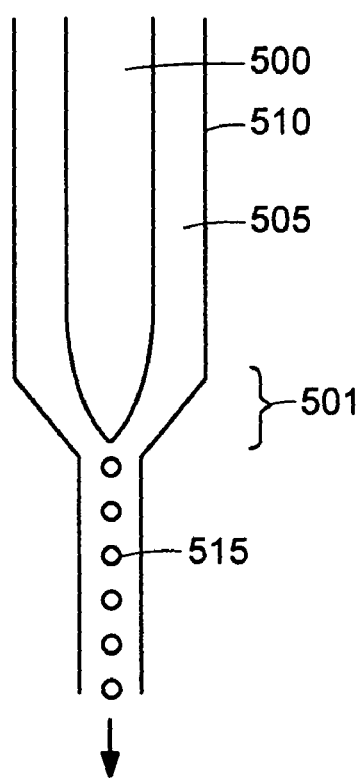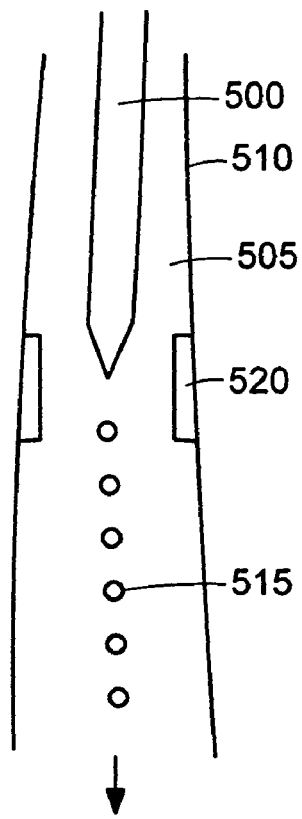
FIG. 7A   FIG. 7B
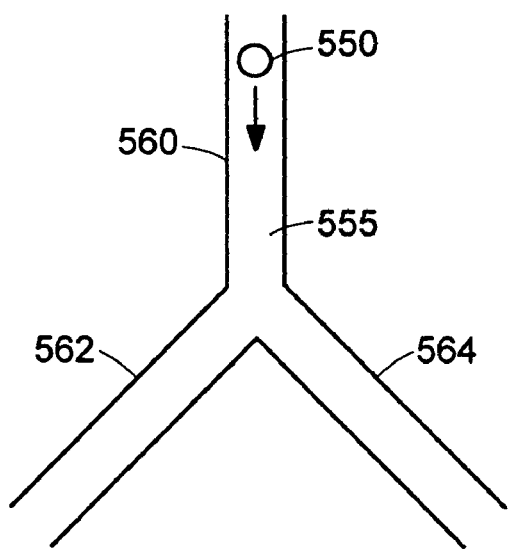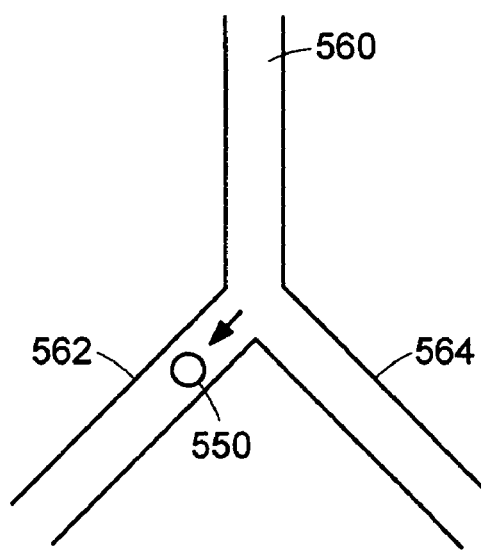
FIG. 8A   FIG. 8B

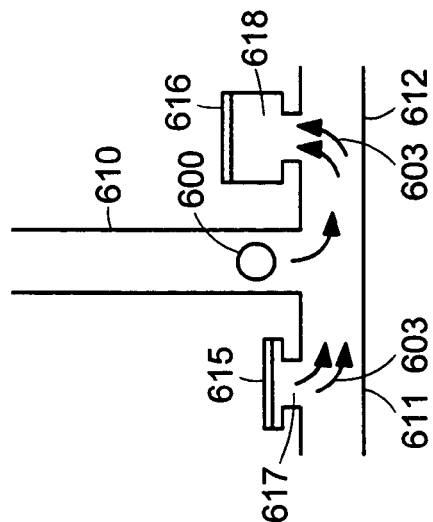
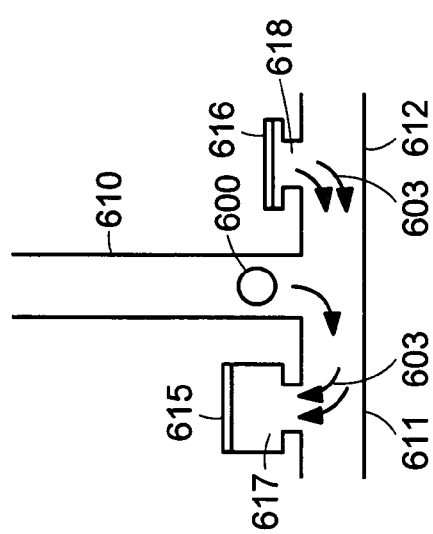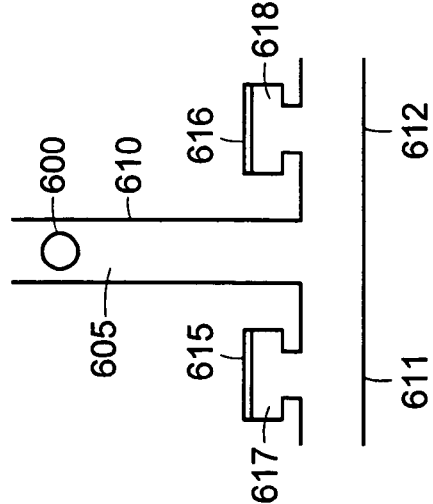

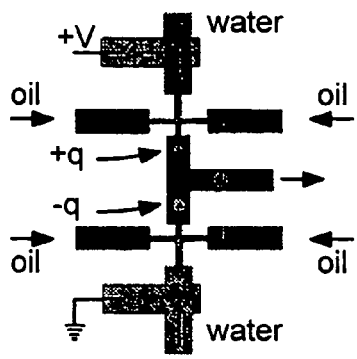
FIG. 18A
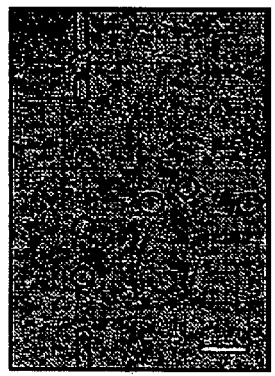     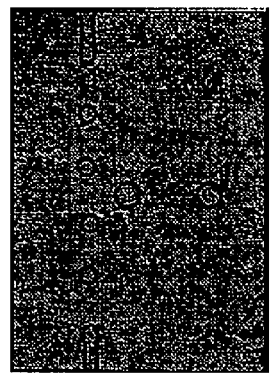
FIG. 18B     FIG. 18C
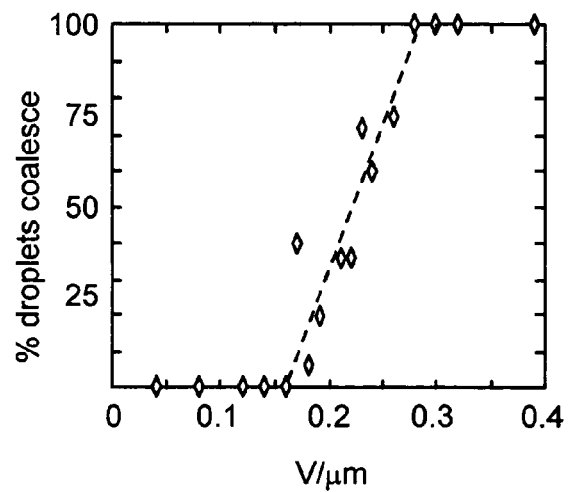
FIG. 18D

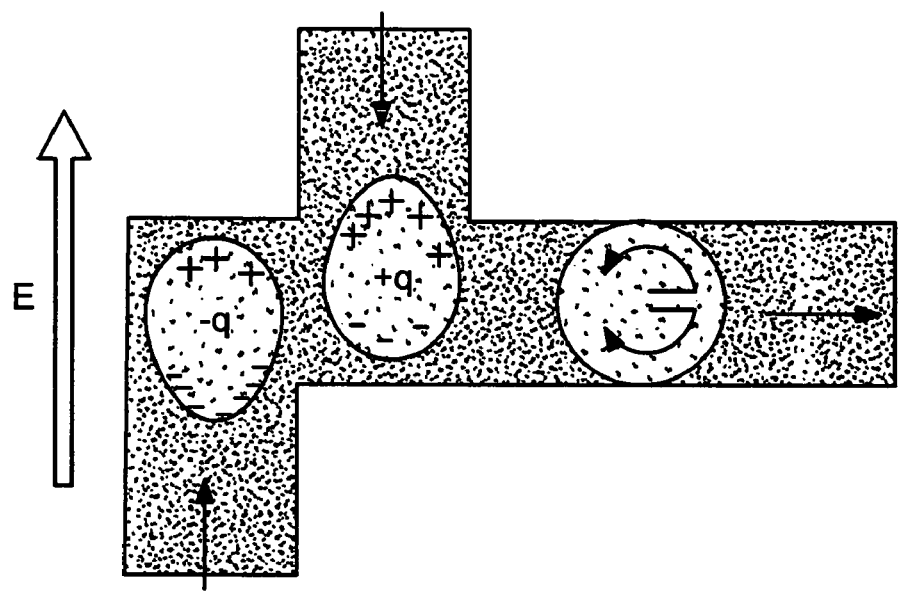
FIG. 20F
  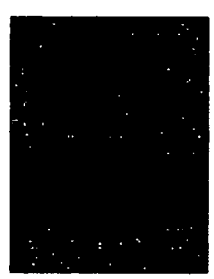
FIG. 20G          FIG. 20H          FIG. 20I

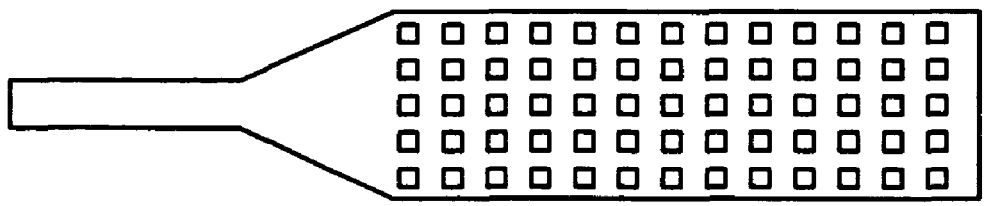
large crossectional area channel
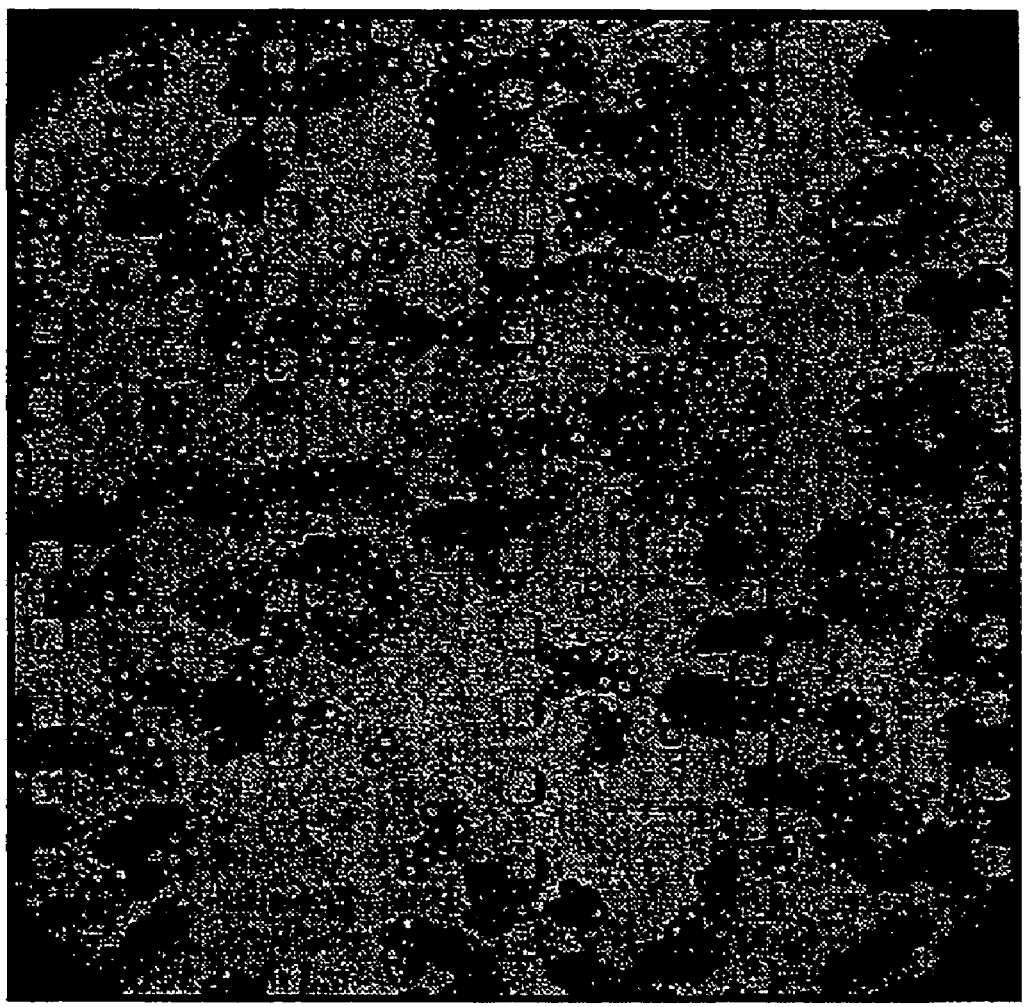
FIG. 21B

IN VITRO EVOLUTION IN MICROFLUIDIC SYSTEMS

The present invention relates to methods for use in vitro evolution of molecular libraries. In particular, the present invention relates to methods of selecting nucleic acids encoding gene products in which the nucleic acid and the activity of the encoded gene product are linked by compartmentation, using microfluidic systems to create and/or handle the compartments.

Evolution requires the generation of genetic diversity (diversity in nucleic acid) followed by the selection of those nucleic acids which result in beneficial characteristics. Because the nucleic acid and the activity of the encoded gene product of an organism are physically linked (the nucleic acids being confined within the cells which they encode) multiple rounds of mutation and selection can result in the progressive survival of organisms with increasing fitness. Systems for rapid evolution of nucleic acids or proteins in vitro advantageously mimic this process at the molecular level in that the nucleic acid and the activity of the encoded gene product are linked and the activity of the gene product is selectable.

Recent advances in molecular biology have allowed some molecules to be co-selected according to their properties along with the nucleic acids that encode them. The selected nucleic acids can subsequently be cloned for further analysis or use, or subjected to additional rounds of mutation and selection.

Common to these methods is the establishment of large libraries of nucleic acids. Molecules having the desired characteristics (activity) can be isolated through selection regimes that select for the desired activity of the encoded gene product, such as a desired biochemical or biological activity, for example binding activity.

Phage display technology has been highly successful as providing a vehicle that allows for the selection of a displayed protein by providing the essential link between nucleic acid and the activity of the encoded gene product (Smith, 1985; Bass et al., 1990; McCafferty et al., 1990; for review see Clackson and Wells, 1994). Filamentous phage particles act as genetic display packages with proteins on the outside and the genetic elements which encode them on the inside. The tight linkage between nucleic acid and the activity of the encoded gene product is a result of the assembly of the phage within bacteria. As individual bacteria are rarely multiply infected, in most cases all the phage produced from an individual bacterium will carry the same genetic element and display the same protein.

However, phage display relies upon the creation of nucleic acid libraries in vivo in bacteria. Thus, the practical limitation on library size allowed by phage display technology is of the order of $10^7$ to $10^{11}$, even taking advantage of □ phage vectors with excisable filamentous phage replicons. The technique has mainly been applied to selection of molecules with binding activity. A small number of proteins with catalytic activity have also been isolated using this technique, however, selection was not directly for the desired catalytic activity, but either for binding to a transition-state analogue (Widersten and Mannervik, 1995) or reaction with a suicide inhibitor (Soumillion et al., 1994; Janda et al., 1997). More recently there have been some examples of enzymes selected using phage-display by product formation (Atwell & Wells, 1999; Demartis et al., 1999; Jestin et al., 1999; Pederson, et al., 1998), but in all these cases selection was not for multiple turnover.

Specific peptide ligands have been selected for binding to receptors by affinity selection using large libraries of peptides linked to the C terminus of the lac repressor LacI (Cull et al., 1992). When expressed in *E. coli* the repressor protein physically links the ligand to the encoding plasmid by binding to a lac operator sequence on the plasmid.

An entirely in vitro polysome display system has also been reported (Mattheakis et al., 1994; Hanes and Pluckthun, 1997) in which nascent peptides are physically attached via the ribosome to the RNA which encodes them. An alternative, entirely in vitro system for linking genotype to phenotype by making RNA-peptide fusions (Roberts and Szostak, 1997; Nemoto et al., 1997) has also been described.

However, the scope of the above systems is limited to the selection of proteins and furthermore does not allow direct selection for activities other than binding, for example catalytic or regulatory activity.

In vitro RNA selection and evolution (Ellington and Szostak, 1990), sometimes referred to as SELEX (systematic evolution of ligands by exponential enrichment) (Tuerk and Gold, 1990) allows for selection for both binding and chemical activity, but only for nucleic acids. When selection is for binding, a pool of nucleic acids is incubated with immobilised substrate. Non-binders are washed away, then the binders are released, amplified and the whole process is repeated in iterative steps to enrich for better binding sequences. This method can also be adapted to allow isolation of catalytic RNA and DNA (Green and Szostak, 1992; for reviews see Chapman and Szostak, 1994; Joyce, 1994; Gold et al., 1995; Moore, 1995).

However, selection for "catalytic" or binding activity using SELEX is only possible because the same molecule performs the dual role of carrying the genetic information and being the catalyst or binding molecule (aptamer). When selection is for "auto-catalysis" the same molecule must also perform the third role of being a substrate. Since the genetic element must play the role of both the substrate and the catalyst, selection is only possible for single turnover events. Because the "catalyst" is in this process itself modified, it is by definition not a true catalyst. Additionally, proteins may not be selected using the SELEX procedure. The range of catalysts, substrates and reactions which can be selected is therefore severely limited.

Those of the above methods that allow for iterative rounds of mutation and selection are mimicking in vitro mechanisms usually ascribed to the process of evolution: iterative variation, progressive selection for a desired the activity and replication. However, none of the methods so far developed have provided molecules of comparable diversity and functional efficacy to those that are found naturally. Additionally, there are no man-made "evolution" systems which can evolve both nucleic acids and proteins to effect the full range of biochemical and biological activities (for example, binding, catalytic and regulatory activities) and that can combine several processes leading to a desired product or activity.

There is thus a great need for an in vitro system that overcomes the limitations discussed above.

In Tawfik and Griffiths (1998), and in International patent application PCT/GB98/01889, we describe a system for in vitro evolution that overcomes many of the limitations described above by using compartmentalisation in microcapsules to link genotype and phenotype at the molecular level.

In Tawfik and Griffiths (1998), and in several embodiments of International patent application WO9902671, the desired activity of a gene product results in a modification of the genetic element which encoded it (and is present in the same microcapsule). The modified genetic element can then be selected in a subsequent step.

Our subsequent international patent application WO0040712 describes a variation of this technology in which the modification of the genetic element causes a change in the optical properties of the element itself, and which has many advantages over the methods described previously.

The manipulation of fluids to form fluid streams of desired configuration, discontinuous fluid streams, droplets, particles, dispersions, etc., for purposes of fluid delivery, product manufacture, analysis, and the like, is a relatively well-studied art. For example, highly monodisperse gas bubbles, less than 100 microns in diameter, have been produced using a technique referred to as capillary flow focusing. In this technique, gas is forced out of a capillary tube into a bath of liquid, the tube is positioned above a small orifice, and the contraction flow of the external liquid through this orifice focuses the gas into a thin jet which subsequently breaks into equal-sized bubbles via a capillary instability. In a related technique, a similar arrangement was used to produce liquid droplets in air.

An article entitled "Generation of Steady Liquid Microthreads and Micron-Sized Monodisperse Sprays and Gas Streams," Phys. Rev. Lett., 80:2, Jan. 12, 1998, 285-288 (Ganan-Calvo) describes formation of a microscopic liquid thread by a laminar accelerating gas stream, giving rise to a fine spray.

An articled entitled "Dynamic Pattern Formation in a Vesicle-Generating Microfluidic Device," Phys. Rev. Lett., 86:18, Apr. 30, 2001 (Thorsen, et al.) describes formation of a discontinuous water phase in a continuous oil phase via microfluidic cross-flow, specifically, by introducing water, at a "T" junction between two microfluidic channels, into flowing oil.

U.S. Pat. No. 6,120,666, issued Sep. 19, 2000, describes a micofabricated device having a fluid focusing chamber for spatially confining first and second sample fluid streams for analysing microscopic particles in a fluid medium, for example in biological fluid analysis.

U.S. Pat. No. 6,116,516, issued Sep. 12, 2000, describes formation of a capillary microjet, and formation of a monodisperse aerosol via disassociation of the microjet.

U.S. Pat. No. 6,187,214, issued Feb. 13, 2001, describes atomised particles in a size range of from about 1 to about 5 microns, produced by the interaction of two immiscible fluids.

U.S. Pat. No. 6,248,378, issued Jun. 19, 2001, describes production of particles for introduction into food using a microjet and a monodisperse aerosol formed when the microjet dissociates.

Microfluidic systems have been described in a variety of contexts, typically in the context of miniaturised laboratory (e.g., clinical) analysis. Other uses have been described as well. For example, International Patent Publication No. WO 01/89789, published Nov. 29, 2001 by Anderson, et al., describes multi-level microfluidic systems that can be used to provide patterns of materials, such as biological materials and cells, on surfaces. Other publications describe microfluidic systems including valves, switches, and other components.

BRIEF DESCRIPTION OF THE INVENTION

According to a first aspect of the present invention, there is provided a method for isolating one or more genetic elements encoding a gene product having a desired activity, comprising the steps of:
(a) compartmentalising the genetic elements into microcapsules;
(b) sorting the genetic elements which express gene product (s) having the desired activity;
wherein at least one step is under microfluidic control.

In the method of the invention, a genetic element may be expressed to form its gene product before or after compartmentalisation; where the gene product is expressed before compartmentalisation, it is linked to the genetic element such that they are compartmentalised together.

Preferably, at least one step is performed using electronic control of fluidic species.

Advantageously at least one step involves fusion or splitting of microcapsules.

Methods for electronic control of fluidic species, as well as splitting (and fusing) of microcapsules under microfluidic control, are described herein.

Preferably, the method of the invention comprises the steps of:
(a) compartmentalising the genetic elements into microcapsules;
(b) expressing the genetic elements to produce their respective gene products within the microcapsules; and
(c) sorting the genetic elements which encode gene product (s) having the desired activity.

Alternatively, the method of the invention comprises the steps of:
(a) expressing the genetic elements to produce their respective gene products such that the gene products are linked to the genes encoding them;
(b) compartmentalising the genetic elements into microcapsules; and
(c) sorting the genetic elements which encode gene product(s) having the desired activity.

The microcapsules according to the present invention compartmentalise genetic elements and gene products such that they remain physically linked together.

As used herein, a genetic element is a molecule or molecular construct comprising a nucleic acid. The genetic elements of the present invention may comprise any nucleic acid (for example, DNA, RNA or any analogue, natural or artificial, thereof). The nucleic acid component of the genetic element may moreover be linked, covalently or non-covalently, to one or more molecules or structures, including proteins, chemical entities and groups, and solid-phase supports such as beads (including nonmagnetic, magnetic and paramagnetic beads), and the like. In the method of the invention, these structures or molecules can be designed to assist in the sorting and/or isolation of the genetic element encoding a gene product with the desired activity.

Expression, as used herein, is used in its broadest meaning, to signify that a nucleic acid contained in the genetic element is converted into its gene product. Thus, where the nucleic acid is DNA, expression refers to the transcription of the DNA into RNA; where this RNA codes for protein, expression may also refer to the translation of the RNA into protein. Where the nucleic acid is RNA, expression may refer to the replication of this RNA into further RNA copies, the reverse transcription of the RNA into DNA and optionally the transcription of this DNA into further RNA molecule(s), as well as optionally the translation of any of the RNA species produced into protein. Preferably, therefore, expression is performed by one or more processes selected from the group consisting of transcription, reverse transcription, replication and translation.

Expression of the genetic element may thus be directed into either DNA, RNA or protein, or a nucleic acid or protein containing unnatural bases or amino acids (the gene product)

within the microcapsule of the invention, so that the gene product is confined within the same microcapsule as the genetic element.

The genetic element and the gene product thereby encoded are linked by confining each genetic element and the respective gene product encoded by the genetic element within the same microcapsule. In this way the gene product in one microcapsule cannot cause a change in any other microcapsules. In addition, further linking means may be employed to link gene products to the genetic elements encoding them, as set forth below.

The term "microcapsule" is used herein in accordance with the meaning normally assigned thereto in the art and further described hereinbelow. In essence, however, a microcapsule is an artificial compartment whose delimiting borders restrict the exchange of the components of the molecular mechanisms described herein which allow the sorting of the genetic elements according to the function of the gene products which they encode. Preferably, the microcapsules used in the method of the present invention will be capable of being produced in very large numbers, and thereby to compartmentalise a library of genetic elements which encodes a repertoire of gene products.

As used herein, a change in optical properties refers to any change in absorption or emission of electromagnetic radiation, including changes in absorbance, luminescence, phosphorescence or fluorescence. All such properties are included in the term "optical". Microcapsules and/or genetic elements can be sorted, for example, by luminescence, fluorescence or phosphorescence activated sorting. In a preferred embodiment, flow cytometry is employed to sort microcapsules and/or genetic elements, for example, light scattering (Kerker, 1983) and fluorescence polarisation (Rolland et al., 1985) can be used to trigger flow sorting. In a highly preferred embodiment genetic elements are sorted using a fluorescence activated cell sorter (FACS) sorter (Norman, 1980; Mackenzie and Pinder, 1986). Such a sorting device can be integrated directly on the microfluidic device, and can use electronic means to sort the microcapsules and/or genetic elements. Optical detection, also integrated directly on the microfluidic device, can be used to screen the microcapsules and/or genetic elements to trigger the sorting. Other means of control of the microcapsules and/or genetic elements, in addition to charge, can also be incorporated onto the microfluidic device.

Changes in optical properties may be direct or indirect. Thus, the change may result in the alteration of an optical property in the microcapsule or genetic element itself, or may lead indirectly to such a change. For example, modification of a genetic element may alter its ability to bind an optically active ligand, thus indirectly altering its optical properties.

Alternatively, imaging techniques can be used to screen thin films of genetic elements to allow enrichment for a genetic element with desirable properties, for example by physical isolation of the region where a genetic element with desirable properties is situated, or ablation of non-desired genetic elements. The genetic elements can be detected by luminescence, phosphorescence or fluorescence.

The sorting of genetic elements may be performed in one of essentially seven techniques.

(I) In a first embodiment, the microcapsules are sorted according to an activity of the gene product or derivative thereof which makes the microcapsule detectable as a whole. Accordingly, a gene product with the desired activity induces a change in the microcapsule, or a modification of one or more molecules within the microcapsule, which enables the microcapsule containing the gene product and the genetic element encoding it to be sorted. In this embodiment the microcapsules are physically sorted from each other according to the activity of the gene product(s) expressed from the genetic element(s) contained therein, which makes it possible selectively to enrich for microcapsules containing gene products of the desired activity.

(II) In a second embodiment, the genetic elements are sorted following pooling of the microcapsules into one or more common compartments. In this embodiment, a gene product having the desired activity modifies the genetic element which encoded it (and which resides in the same microcapsule) in such a way as to make it selectable in a subsequent step. The reactions are stopped and the microcapsules are then broken so that all the contents of the individual microcapsules are pooled. Selection for the modified genetic elements enables enrichment of the genetic elements encoding the gene product(s) having the desired activity. Accordingly, the gene product having the desired activity modifies the genetic element encoding it to enable the isolation of the genetic element. It is to be understood, of course, that modification may be direct, in that it is caused by the direct action of the gene product on the genetic element, or indirect, in which a series of reactions, one or more of which involve the gene product having the desired activity, leads to modification of the genetic element.

(III) In a third embodiment, the genetic elements are sorted following pooling of the microcapsules into one or more common compartments. In this embodiment, a gene with a desired activity induces a change in the microcapsule containing the gene product and the genetic element encoding it. This change, when detected, triggers the modification of the gene within the compartment. The reactions are stopped and the microcapsules are then broken so that all the contents of the individual microcapsules are pooled. Selection for the modified genetic elements enables enrichment of the genetic elements encoding the gene product(s) having the desired activity. Accordingly the gene product having the desired activity induces a change in the compartment which is detected and triggers the modification of the genetic element within the compartment so as to allow its isolation. It is to be understood that the detected change in the compartment may be caused by the direct action of the gene product, or indirect action, in which a series of reactions, one or more of which involve the gene product having the desired activity leads to the detected change.

(IV) In a fourth embodiment, the genetic elements may be sorted by a multi-step procedure, which involves at least two steps, for example, in order to allow the exposure of the genetic elements to conditions which permit at least two separate reactions to occur. As will be apparent to a persons skilled in the art, the first microencapsulation step of the invention must result in conditions which permit the expression of the genetic elements—be it transcription, transcription and/or translation, replication or the like. Under these conditions, it may not be possible to select for a particular gene product activity, for example because the gene product may not be active under these conditions, or because the expression system contains an interfering activity. The method therefore comprises expressing the genetic elements to produce their respective gene products within the microcapsules, linking the gene products to the genetic elements encoding them and isolating the complexes thereby formed. This allows for the genetic elements and their associated gene products to be isolated from the capsules before sorting according to gene product activity takes place. In a preferred embodiment, the complexes are subjected to a further compartmentalisation step prior to isolating the genetic elements encoding a gene product having the desired activity. This further compartmentalisation step, which advantageously takes place in microcapsules, permits the performance of further reactions, under different conditions, in an environment where the genetic elements and their respective gene products are physically linked. Eventual sorting of genetic elements may be performed according to embodiment (I), (II) or (III) above.

Where the selection is for optical changes in the genetic elements, the selection may be performed as follows:

(V) In a fifth embodiment, the genetic elements are sorted following pooling of the microcapsules into one or more common compartments. In this embodiment, a gene product having the desired activity modifies the genetic element which encoded it (and which resides in the same microcapsule) so as to make it selectable as a result of its modified optical properties in a subsequent step. The reactions are stopped and the microcapsules are then broken so that all the contents of the individual microcapsules are pooled. The modification of the genetic element in the microcapsule may result directly in the modification of the optical properties of the genetic element. Alternatively, the modification may allow the genetic elements to be further modified outside the microcapsules so as to induce a change in their optical properties. Selection for the genetic elements with modified optical properties enables enrichment of the genetic elements encoding the gene product(s) having the desired activity. Accordingly, the gene product having the desired activity modifies the genetic element encoding it to enable the isolation of the genetic element as a result in a change in the optical properties of the genetic element. It is to be understood, of course, that modification may be direct, in that it is caused by the direct action of the gene product on the genetic element, or indirect, in which a series of reactions, one or more of which involve the gene product having the desired activity, leads to modification of the genetic element.

(VI) In a sixth embodiment, the genetic elements may be sorted by a multi-step procedure, which involves at least two steps, for example, in order to allow the exposure of the genetic elements to conditions which permit at least two separate reactions to occur. As will be apparent to persons skilled in the art, the first microencapsulation step of the invention advantageously results in conditions which permit the expression of the genetic elements—be it transcription, transcription and/or translation, replication or the like. Under these conditions, it may not be possible to select for a particular gene product activity, for example because the gene product may not be active under these conditions, or because the expression system contains an interfering activity. The method therefore comprises expressing the genetic elements to produce their respective gene products within the microcapsules, linking the gene products to the genetic elements encoding them and isolating the complexes thereby formed. This allows for the genetic elements and their associated gene products to be isolated from the capsules before sorting according to gene product activity takes place. In a preferred embodiment, the complexes are subjected to a further compartmentalisation step prior to isolating the genetic elements encoding a gene product having the desired activity. This further compartmentalisation step, which advantageously takes place in microcapsules, permits the performance of further reactions, under different conditions, in an environment where the genetic elements and their respective gene products are physically linked. Eventual sorting of genetic elements may be performed according to embodiment (V) above.

The "secondary encapsulation" may also be performed with genetic elements linked to gene products by other means, such as by phage display, polysome display, RNA-peptide fusion or lac repressor peptide fusion, optionally where expression takes place prior to encapsulation; or even by the encapsulation of whole cells containing the desired genetic element.

The selected genetic element(s) may also be subjected to subsequent, possibly more stringent rounds of sorting in iteratively repeated steps, reapplying the method described above either in its entirety or in selected steps only. By tailoring the conditions appropriately, genetic elements encoding gene products having a better optimised activity may be isolated after each round of selection.

Additionally, the genetic elements isolated after a first round of sorting may be subjected to mutagenesis before repeating the sorting by iterative repetition of the steps of the method of the invention as set out above. After each round of mutagenesis, some genetic elements will have been modified in such a way that the activity of the gene products is enhanced.

Moreover, the selected genetic elements can be cloned into an expression vector to allow further characterisation of the genetic elements and their products.

(VII) In a seventh embodiment, the microcapsules may be sorted using microfluidic approaches. The microcapsules may be produced using microfluidic droplet formation techniques, such as those described herein, or by other techniques, for example conventional emulsification by forcing together two fluid phases. Sorting using microfluidics is applicable to embodiments I to VI above, and provides enhanced processing of microcapsules leading to improved sorting. Microcapsules may be split or fused according to methods described herein, or the contents thereof mixed. Moreover, the contents of the microcapsules may be analysed and the microcapsules sorted using detectors in microfluidic systems.

In a second aspect, the invention provides a product when selected according to the first aspect of the invention. As used in this context, a "product" may refer to a gene product, selectable according to the invention, or the genetic element (or genetic information comprised therein).

In a third aspect, the invention provides a method for preparing a gene product, the expression of which may result, directly or indirectly, in the modification the optical properties of a genetic element encoding it, comprising the steps of:
(a) preparing a genetic element encoding the gene product;
(b) compartmentalising genetic elements into microcapsules;
(c) expressing the genetic elements to produce their respective gene products within the microcapsules;
(d) sorting the genetic elements which produce the gene product(s) having the desired activity using the changed optical properties of the genetic elements; and
(e) expressing the gene product having the desired activity; wherein one or both of steps (b) and (d) is performed under microfluidic control.

In accordance with the third aspect, step (a) preferably comprises preparing a repertoire of genetic elements, wherein each genetic element encodes a potentially differing gene product. Repertoires may be generated by conventional techniques, such as those employed for the generation of libraries intended for selection by methods such as phage display. Gene products having the desired activity may be selected from the repertoire, according to the present invention, according to their ability to modify the optical properties of the genetic elements in a manner which differs from that of other gene products. For example, desired gene products may modify the optical properties to a greater extent than other gene products, or to a lesser extent, including not at all.

In a fourth aspect, the invention provides a method for screening a compound or compounds capable of modulation the activity of a gene product, the expression of which may result, directly or indirectly, in the modification of the optical properties of a genetic element encoding it, comprising the steps of:
(a) preparing a repertoire of genetic elements encoding gene product;
(b) compartmentalising genetic elements into microcapsules;
(c) expressing the genetic elements to produce their respective gene products within the microcapsules;
(d) sorting the genetic elements which produce the gene product(s) having the desired activity using the changed optical properties of the genetic elements; and
(e) contacting a gene product having the desired activity with the compound or compounds and monitoring the modulation of an activity of the gene product by the compound or compounds; wherein one or both of steps (b) and (d) is performed under microfluidic control.

Advantageously, the method further comprises the step of:
(f) identifying the compound or compounds capable of modulating the activity of the gene product and synthesising said compound or compounds.

This selection system can be configured to select for RNA, DNA or protein molecules with catalytic, regulatory or binding activity.

BRIEF DESCRIPTION OF THE FIGURES

FIGS. 7a and 7b are schematic diagrams of the formation of microfluidic droplets in accordance with the present invention;

FIGS. 8a-f illustrate the splitting of droplets in accordance with the invention;

FIGS. 11a-c illustrate the use of pressure changes in the microfluidic system to control the direction of flow of droplets;

FIG. 18 Coalescing drops. (A) Drops having opposite sign of electrostatic charge can be generated by applying a voltage across the two aqueous streams. (B) In the absence of the field the frequency and timing of drop formation at the two nozzles are independent and each nozzle produces a different size drop at a different frequency; infusion rates are the same at both nozzles. After the confluence of the two streams, drops from the upper and lower nozzles stay in their respective halves of the stream and due to surfactant there are no coalescence events even in the case of large slugs that fill the channel width. (C) With an applied voltage of 200V across the 500 micron separation of the nozzles, the drops simultaneously break-off from the two nozzles and are identical; simultaneous drop formation can be achieved for unequal infusion rates of the aqueous streams even up to a factor of two difference in volumes. (D) The fraction of the drops that encounter each other and coalesce increases linearly above a critical field when a surfactant, sorbiton-monooleate 3% is present.

DEFINITIONS

Figure 1A:
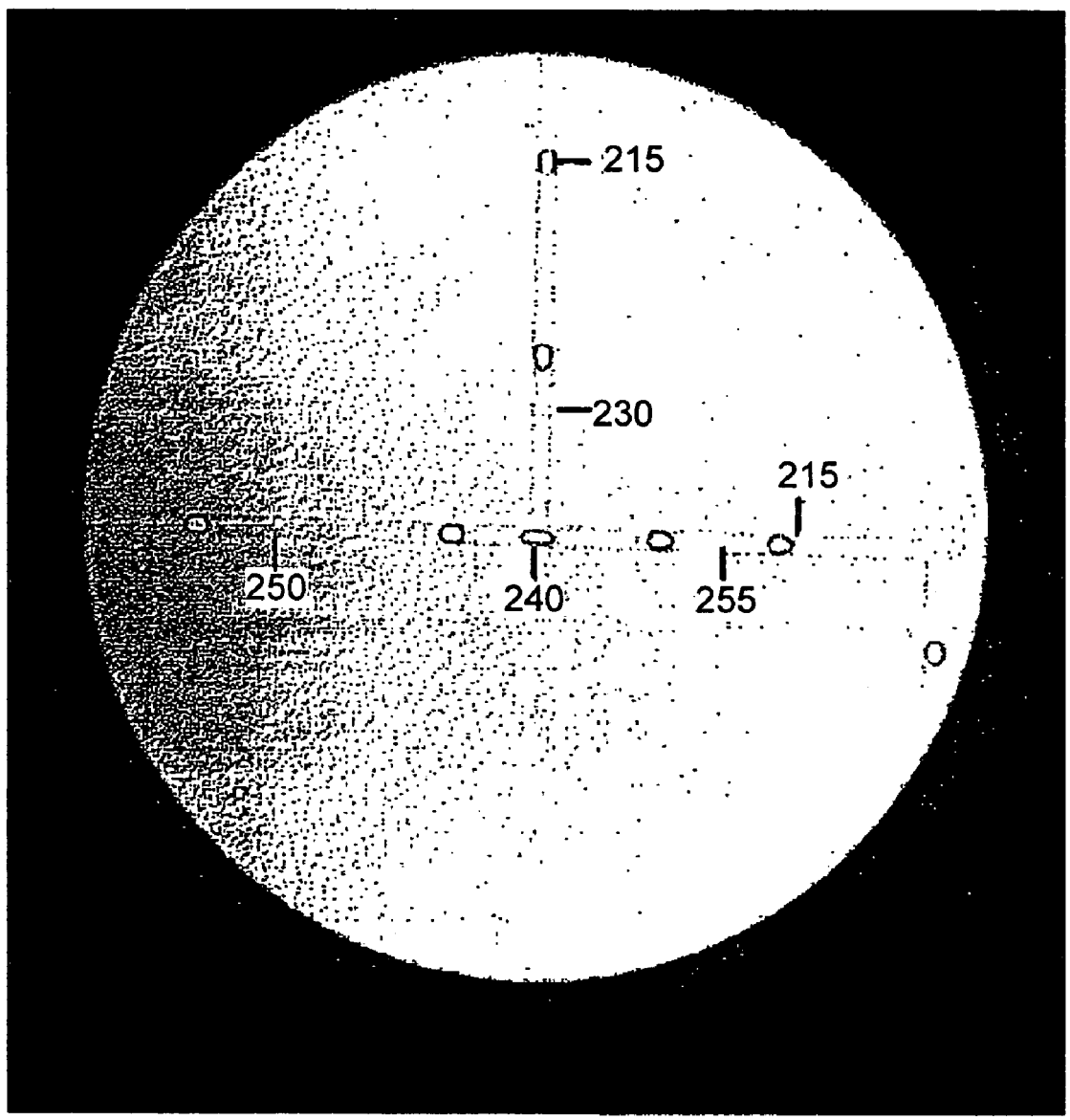
FIGS. 1A and 1B illustrate the splitting of droplets in accordance with one embodiment of the invention.

As used herein, "or" is understood to mean "inclusively or," i.e., the inclusion of at least one, but including more than one, of a number or list of elements. In contrast, the term "exclusively or" refers to the inclusion of exactly one element of a number or list of elements.

The indefinite articles "a" and "an," as used herein in the specification and in the claims, should be understood to mean "at least one."

The term "about," as used herein in reference to a numerical parameter (for example, a physical, chemical, electrical, or biological property), will be understood by those of ordinary skill in the art to be an approximation of a numerical value, the exact value of which may be subject to errors such as those resulting from measurement errors of the numerical parameter, uncertainties resulting from the variability and/or reproducibility of the numerical parameter (for example, in separate experiments), and the like.

The term "microcapsule" is used herein in accordance with the meaning normally assigned thereto in the art and further described hereinbelow. In essence, however, a microcapsule is an artificial compartment whose delimiting borders restrict the exchange of the components of the molecular mechanisms described herein which allow the identification of the molecule with the desired activity. The delimiting borders preferably completely enclose the contents of the microcapsule. Preferably, the microcapsules used in the method of the present invention will be capable of being produced in very large numbers, and thereby to compartmentalise a library of genetic elements. Optionally, the genetic elements can comprise genes attached to microbeads. The microcapsules used herein allow mixing and sorting to be performed thereon, in order to facilitate the high throughput potential of the methods of the invention. A microcapsule can be a droplet of one fluid in a different fluid, where the confined components are soluble in the droplet but not in the carrier fluid. In another embodiment there is a third material defining a wall, such as a membrane.

Arrays of liquid droplets on solid surfaces, multiwell plates and "plugs" in microfluidic systems, that is fluid droplets that are not completely surrounded by a second fluid as defined herein, are not microcapsules as defined herein.

The term "microbead" is used herein in accordance with the meaning normally assigned thereto in the art and further described hereinbelow. Microbeads, are also known by those skilled in the art as microspheres, latex particles, beads, or minibeads, are available in diameters from 20 nm to 1 mm and can be made from a variety of materials including silica and a variety of polymers, copolymers and terpolymers. Highly uniform derivatised and non-derivatised nonmagnetic and paramagnetic microparticles (beads) are commercially available from many sources (e.g. Sigma, Bangs Laboratories, Luminex and Molecular Probes) (Fornusek and Vetvicka, 1986).

Microbeads can be "compartmentalised" in accordance with the present invention by distribution into microcapsules. For example, in a preferred aspect the microbeads can be placed in a water/oil mixture and emulsified to form a water-in-oil emulsion comprising microcapsules according to the invention. The concentration of the microbeads can be adjusted such that a single microbead, on average, appears in each microcapsule.

As used herein, the "target" is any compound, molecule, or supramolecular complex. Typical targets include targets of medical significance, including drug targets such as receptors, for example G protein coupled receptors and hormone receptors; transcription factors, protein kinases and phosphatases involved in signalling pathways; gene products specific to microorganisms, such as components of cell walls, replicases and other enzymes; industrially relevant targets, such as enzymes used in the food industry, reagents intended for research or production purposes, and the like.

A "desired activity", as referred to herein, is the modulation of any activity of a target, or an activity of a molecule which is influenced by the target, which is modulatable directly or indirectly by a genetic element or genetic elements as assayed herein. The activity of the target may be any measurable biological or chemical activity, including binding activity, an enzymatic activity, an activating or inhibitory activity on a third enzyme or other molecule, the ability to cause disease or influence metabolism or other functions, and the like. Activation and inhibition, as referred to herein, denote the increase or decrease of a desired activity 1.5 fold, 2 fold, 3 fold, 4 fold, 5 fold, 10 fold, 100 fold or more. Where the modulation is inactivation, the inactivation can be substantially complete inactivation. The desired activity may moreover be purely a binding activity, which may or may not involve the modulation of the activity of the target bound to.

A compound defined herein as "low molecular weight" or a "small molecule" is a molecule commonly referred to in the pharmaceutical arts as a "small molecule". Such compounds are smaller than polypeptides and other, large molecular complexes and can be easily administered to and assimilated by patients and other subjects. Small molecule drugs can advantageously be formulated for oral administration or intramuscular injection. For example, a small molecule may have a molecular weight of up to 2000 Dalton; preferably up to 1000 Dalton; advantageously between 250 and 750 Dalton; and more preferably less than 500 Dalton.

A "selectable change" is any change which can be measured and acted upon to identify or isolate the genetic element which causes it. The selection may take place at the level of the microcapsule, the microbead, or the genetic element itself, optionally when complexed with another reagent. A particularly advantageous embodiment is optical detection, in which the selectable change is a change in optical properties, which can be detected and acted upon for instance in a flow sorting device to separate microcapsules or microbeads displaying the desired change.

As used herein, a change in optical properties refers to any change in absorption or emission of electromagnetic radiation, including changes in absorbance, luminescence, phosphorescence or fluorescence. All such properties are included in the term "optical". Microcapsules or microbeads can be identified and, optionally, sorted, for example, by luminescence, fluorescence or phosphorescence activated sorting. In a preferred embodiment, flow sorting is employed to identify and, optionally, sort microcapsules or microbeads. A variety of optical properties can be used for analysis and to trigger sorting, including light scattering (Kerker, 1983) and fluorescence polarisation (Rolland et al., 1985).

The genetic elements in microcapsules or on beads can be identified using a variety of techniques familiar to those skilled in the art, including mass spectroscopy, chemical tagging or optical tagging.

As used herein, "microfluidic control" refers to the use of a microfluidic system comprising microfluidic channels as defined herein to direct or otherwise control the formation and/or movement of microcapsules (or "droplets") in order to carry out the methods of the present invention. For example, "microfluidic control" of microcapsule formation refers to the creation of microcapsules using a microfluidic device to form "droplets" of fluid within a second fluid, thus creating a microcapsule. Microcapsules sorted under microfluidic control are sorted, as described herein, using a microfluidic device to perform one or more of the functions associated with the sorting procedure. "Microfluidic control of fluidic species", therefore, refers to the handling of fluids in a microfluidic system as defined in order to carry out the methods of the present invention.

As used herein, a "cell" is given its ordinary meaning as used in biology. The cell may be any cell or cell type. For example, the cell may be a bacterium or other single-cell organism, a plant cell, or an animal cell. If the cell is a single-cell organism, then the cell may be, for example, a protozoan, a trypanosome, an amoeba, a yeast cell, algae, etc. If the cell is an animal cell, the cell may be, for example, an invertebrate cell (e.g., a cell from a fruit fly), a fish cell (e.g., a zebrafish cell), an amphibian cell (e.g., a frog cell), a reptile cell, a bird cell, or a mammalian cell such as a primate cell, a bovine cell, a horse cell, a porcine cell, a goat cell, a dog cell, a cat cell, or a cell from a rodent such as a rat or a mouse. If the cell is from a multicellular organism, the cell may be from any part of the organism. For instance, if the cell is from an animal, the cell may be a cardiac cell, a fibroblast, a keratinocyte, a heptaocyte, a chondrocyte, a neural cell, a osteocyte, a muscle cell, a blood cell, an endothelial cell, an immune cell (e.g., a T-cell, a B-cell, a macrophage, a neutrophil, a basophil, a mast cell, an eosinophil), a stem cell, etc. In some cases, the cell may be a genetically engineered cell. In certain embodiments, the cell may be a Chinese hamster ovarian ("CHO") cell or a 3T3 cell.

"Microfluidic," as used herein, refers to a device, apparatus or system including at least one fluid channel having a cross-sectional dimension of less than 1 mm, and a ratio of length to largest cross-sectional dimension of at least 3:1. A "microfluidic channel," as used herein, is a channel meeting these criteria.

The "cross-sectional dimension" of the channel is measured perpendicular to the direction of fluid flow. Most fluid channels in components of the invention have maximum cross-sectional dimensions less than 2 mm, and in some cases, less than 1 mm. In one set of embodiments, all fluid channels containing embodiments of the invention are microfluidic or have a largest cross sectional dimension of no more than 2 mm or 1 mm. In another embodiment, the fluid channels may be formed in part by a single component (e.g. an etched substrate or moulded unit). Of course, larger channels, tubes, chambers, reservoirs, etc. can be used to store fluids in bulk and to deliver fluids to components of the invention. In one set of embodiments, the maximum cross-sectional dimension of the channel(s) containing embodiments of the invention are less than 500 microns, less than 200 microns, less than 100 microns, less than 50 microns, or less than 25 microns.

A "channel," as used herein, means a feature on or in an article (substrate) that at least partially directs the flow of a fluid. The channel can have any cross-sectional shape (circular, oval, triangular, irregular, square or rectangular, or the like) and can be covered or uncovered. In embodiments where it is completely covered, at least one portion of the channel can have a cross-section that is completely enclosed, or the entire channel may be completely enclosed along its entire length with the exception of its inlet(s) and outlet(s). A channel may also have an aspect ratio (length to average cross sectional dimension) of at least 2:1, more typically at least 3:1, 5:1, or 10:1 or more. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an open channel is used, the fluid may be held within the channel, for example, using surface tension (i.e., a concave or convex meniscus).

The channel may be of any size, for example, having a largest dimension perpendicular to fluid flow of less than about 5 mm or 2 mm, or less than about 1 mm, or less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm. In some cases the dimensions of the channel may be chosen such that fluid is able to freely flow through the article or substrate. The dimensions of the channel may also be chosen, for example, to allow a certain volumetric or linear flowrate of fluid in the channel. Of course, the number of channels and the shape of the channels can be varied by any method known to those of ordinary skill in the art. In some cases, more than one channel or capillary may be used. For example, two or more channels may be used, where they are positioned inside each other, positioned adjacent to each other, positioned to intersect with each other, etc.

As used herein, "integral" means that portions of components are joined in such a way that they cannot be separated from each other without cutting or breaking the components from each other.

A "droplet," as used herein is an isolated portion of a first fluid that is completely surrounded by a second fluid. It is to be noted that a droplet is not necessarily spherical, but may assume other shapes as well, for example, depending on the external environment. In one embodiment, the droplet has a minimum cross-sectional dimension that is substantially equal to the largest dimension of the channel perpendicular to fluid flow in which the droplet is located.

The "average diameter" of a population of droplets is the arithmetic average of the diameters of the droplets. Those of ordinary skill in the art will be able to determine the average diameter of a population of droplets, for example, using laser light scattering or other known techniques. The diameter of a droplet, in a non-spherical droplet, is the mathematically-defined average diameter of the droplet, integrated across the entire surface. As non-limiting examples, the average diameter of a droplet may be less than about 1 mm, less than about 500 micrometers, less than about 200 micrometers, less than about 100 micrometers, less than about 75 micrometers, less than about 50 micrometers, less than about 25 micrometers, less than about 10 micrometers, or less than about 5 micrometers. The average diameter of the droplet may also be at least about 1 micrometer, at least about 2 micrometers, at least about 3 micrometers, at least about 5 micrometers, at least about 10 micrometers, at least about 15 micrometers, or at least about 20 micrometers in certain cases.

As used herein, a "fluid" is given its ordinary meaning, i.e., a liquid or a gas. Preferably, a fluid is a liquid. The fluid may have any suitable viscosity that permits flow. If two or more fluids are present, each fluid may be independently selected among essentially any fluids (liquids, gases, and the like) by those of ordinary skill in the art, by considering the relationship between the fluids. The fluids may each be miscible or immiscible. For example, two fluids can be selected to be immiscible within the time frame of formation of a stream of fluids, or within the time frame of reaction or interaction. Where the portions remain liquid for a significant period of time then the fluids should be significantly immiscible. Where, after contact and/or formation, the dispersed portions are quickly hardened by polymerisation or the like, the fluids need not be as immiscible. Those of ordinary skill in the art can select suitable miscible or immiscible fluids, using contact angle measurements or the like, to carry out the techniques of the invention.

As used herein, a first entity is "surrounded" by a second entity if a closed loop can be drawn around the first entity through only the second entity. A first entity is "completely surrounded" if closed loops going through only the second entity can be drawn around the first entity regardless of direction. In one aspect, the first entity may be a cell, for example, a cell suspended in media is surrounded by the media. In another aspect, the first entity is a particle. In yet another aspect of the invention, the entities can both be fluids. For example, a hydrophilic liquid may be suspended in a hydrophobic liquid, a hydrophobic liquid may be suspended in a hydrophilic liquid, a gas bubble may be suspended in a liquid, etc. Typically, a hydrophobic liquid and a hydrophilic liquid are substantially immiscible with respect to each other, where the hydrophilic liquid has a greater affinity to water than does the hydrophobic liquid. Examples of hydrophilic liquids include, but are not limited to, water and other aqueous solutions comprising water, such as cell or biological media, ethanol, salt solutions, etc. Examples of hydrophobic liquids include, but are not limited to, oils such as hydrocarbons, silicon oils, fluorocarbon oils, organic solvents etc.

The term "determining," as used herein, generally refers to the analysis or measurement of a species, for example, quantitatively or qualitatively, or the detection of the presence or absence of the species. "Determining" may also refer to the analysis or measurement of an interaction between two or more species, for example, quantitatively or qualitatively, or by detecting the presence or absence of the interaction. Example techniques include, but are not limited to, spectroscopy such as infrared, absorption, fluorescence, UV/visible, FTIR ("Fourier Transform Infrared Spectroscopy"), or Raman; gravimetric techniques; ellipsometry; piezoelectric measurements; immunoassays; electrochemical measurements; optical measurements such as optical density measurements; circular dichroism; light scattering measurements such as quasielectric light scattering; polarimetry; refractometry; or turbidity measurements.

Unless defined otherwise, all technical and scientific terms used herein have the same meaning as commonly understood by one of ordinary skill in the art (e.g., in cell culture, molecular genetics, nucleic acid chemistry, hybridisation techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999)$4^{th}$ Ed, John Wiley & Sons, Inc. which are incorporated herein by reference) and chemical methods. In addition Harlow & Lane, A Laboratory Manual Cold Spring Harbor, N.Y., is referred to for standard Immunological Techniques.

(A) General Description

The microcapsules of the present invention require appropriate physical properties to allow the working of the invention.

First, to ensure that the genetic elements and gene products may not diffuse between microcapsules, the contents of each microcapsule are preferably isolated from the contents of the surrounding microcapsules, so that there is no or little exchange of the genetic elements and gene products between the microcapsules over the timescale of the experiment. However, the permeability of the microcapsules may be adjusted such that reagents may be allowed to diffuse into and/or out of the microcapsules if desired.

Second, the method of the present invention requires that there are only a limited number of genetic elements per microcapsule. This ensures that the gene product of an individual genetic element will be isolated from other genetic elements. Thus, coupling between genetic element and gene product will be highly specific. The enrichment factor is greatest with on average one or fewer genetic elements per microcapsule, the linkage between nucleic acid and the activity of the encoded gene product being as tight as is possible, since the gene product of an individual genetic element will be isolated from the products of all other genetic elements. However, even if the theoretically optimal situation of, on average, a single genetic element or less per microcapsule is not used, a ratio of 5, 10, 50, 100 or 1000 or more genetic elements per microcapsule may prove beneficial in sorting a large library. Subsequent rounds of sorting, including renewed encapsulation with differing genetic element distribution, will permit more stringent sorting of the genetic elements. Preferably, there is a single genetic element, or fewer, per microcapsule.

Third, the formation and the composition of the microcapsules advantageously does not abolish the function of the machinery the expression of the genetic elements and the activity of the gene products.

Consequently, any microencapsulation system used preferably fulfils these three requirements. The appropriate system(s) may vary depending on the precise nature of the requirements in each application of the invention, as will be apparent to the skilled person.

A wide variety of microencapsulation procedures are available (see Benita, 1996) and may be used to create the microcapsules used in accordance with the present invention. Indeed, more than 200 microencapsulation methods have been identified in the literature (Finch, 1993).

Enzyme-catalysed biochemical reactions have also been demonstrated in microcapsules generated by a variety of other methods. Many enzymes are active in reverse micellar solutions (Bru & Walde, 1991; Bru & Walde, 1993; Creagh et al., 1993; Haber et al., 1993; Kumar et al., 1989; Luisi & B., 1987; Mao & Walde, 1991; Mao et al., 1992; Perez et al., 1992; Walde et al., 1994; Walde et al., 1993; Walde et al., 1988) such as the AOT-isooctane-water system (Menger & Yamada, 1979).

Microcapsules can also be generated by interfacial polymerisation and interfacial complexation (Whateley, 1996). Microcapsules of this sort can have rigid, nonpermeable membranes, or semipermeable membranes. Semipermeable microcapsules bordered by cellulose nitrate membranes, polyamide membranes and lipid-polyamide membranes can all support biochemical reactions, including multienzyme systems (Chang, 1987; Chang, 1992; Lim, 1984). Alginate/polylysine microcapsules (Lim & Sun, 1980), which can be formed under very mild conditions, have also proven to be very biocompatible, providing, for example, an effective method of encapsulating living cells and tissues (Chang, 1992; Sun et al., 1992).

Non-membranous microencapsulation systems based on phase partitioning of an aqueous environment in a colloidal system, such as an emulsion, may also be used.

Preferably, the microcapsules of the present invention are formed from emulsions; heterogeneous systems of two immiscible liquid phases with one of the phases dispersed in the other as droplets of microscopic or colloidal size (Becher, 1957; Sherman, 1968; Lissant, 1974; Lissant, 1984).

Emulsions may be produced from any suitable combination of immiscible liquids. Preferably the emulsion of the present invention has "water" (an aqueous liquid containing the biochemical components) as the phase present in the form of finely divided droplets (the disperse, internal or discontinuous phase) and a hydrophobic, immiscible liquid (an 'oil') as the matrix in which these droplets are suspended (the nondisperse, continuous or external phase). Such emulsions are termed 'water-in-oil' (W/O). This has the advantage that the entire aqueous phase containing the biochemical components is compartmentalised in discreet droplets (the internal phase). The external phase, being a hydrophobic liquid, generally contains none of the biochemical components and hence is inert.

The emulsion may be stabilised by addition of one or more surface-active agents (surfactants). These surfactants are termed emulsifying agents and act at the water/oil interface to prevent (or at least delay) separation of the phases. Many oils and many emulsifiers can be used for the generation of water-in-oil emulsions; a recent compilation listed over 16,000 surfactants, many of which are used as emulsifying agents (Ash and Ash, 1993). Suitable oils include light white mineral oil and decane. Suitable surfactants include: non-ionic surfactants (Schick, 1966) such as sorbitan monooleate (Span™80; ICI), sorbitan monostearate (Span™60; ICI), polyoxyethylenesorbitan monooleate (Tween™ 80; ICI), and octylphenoxyethoxyethanol (Triton X-100); ionic surfactants such as sodium cholate and sodium taurocholate and sodium deoxycholate; chemically inert silicone-based surfactants such as polysiloxane-polycetyl-polyethylene glycol copolymer (Cetyl Dimethicone Copolyol) (e.g. Abil™EM90; Goldschmidt); and cholesterol.

Emulsions with a fluorocarbon (or perfluorocarbon) continuous phase (Krafft et al., 2003; Riess, 2002) may be particularly advantageous. For example, stable water-in-perfluorooctyl bromide and water-in-perfluorooctylethane emulsions can be formed using F-alkyl dimorpholinophosphates as surfactants (Sadtler et al., 1996). Non-fluorinated compounds are essentially insoluble in fluorocarbons and perfluorocarbons (Curran, 1998; Hildebrand and Cochran, 1949; Hudlicky, 1992; Scott, 1948; Studer et al., 1997) and small drug-like molecules (typically <500 Da and Log P<5) (Lipinski et al., 2001) are compartmentalised very effectively in the aqueous microcapsules of water-in-fluorocarbon and water-in-perfluorocarbon emulsions—with little or no exchange between microcapsules.

Creation of an emulsion generally requires the application of mechanical energy to force the phases together. There are a variety of ways of doing this which utilise a variety of mechanical devices, including stirrers (such as magnetic stirbars, propeller and turbine stirrers, paddle devices and whisks), homogenisers (including rotor-stator homogenisers, high-pressure valve homogenisers and jet homogenisers), colloid mills, ultrasound and 'membrane emulsification' devices (Becher, 1957; Dickinson, 1994), and microfluidic devices (Umbanhowar et al., 2000).

Complicated biochemical processes, notably gene transcription and translation are also active in aqueous microcapsules formed in water-in-oil emulsions. This has enabled compartmentalisation in water-in-oil emulsions to be used for the selection of genes, which are transcribed and translated in emulsion microcapsules and selected by the binding or catalytic activities of the proteins they encode (Doi and Yanagawa, 1999; Griffiths and Tawfik, 2003; Lee et al., 2002; Sepp et al., 2002; Tawfik and Griffiths, 1998). This was possible because the aqueous microcapsules formed in the emulsion were generally stable with little if any exchange of nucleic acids, proteins, or the products of enzyme catalysed reactions between microcapsules.

The technology exists to create emulsions with volumes all the way up to industrial scales of thousands of liters (Becher, 1957; Sherman, 1968; Lissant, 1974; Lissant, 1984).

The preferred microcapsule size will vary depending upon the precise requirements of any individual selection process that is to be performed according to the present invention. In all cases, there will be an optimal balance between gene library size, the required enrichment and the required concentration of components in the individual microcapsules to achieve efficient expression and reactivity of the gene products.

The processes of expression occurs within each individual microcapsule provided by the present invention. Both in vitro transcription and coupled transcription-translation become less efficient at sub-nanomolar DNA concentrations. Because of the requirement for only a limited number of DNA molecules to be present in each microcapsule, this therefore sets a practical upper limit on the possible microcapsule size. Preferably, the mean volume of the microcapsules is less that $5.2 \times 10^{-16}$ m$^3$, (corresponding to a spherical microcapsule of diameter less than 10 µm, more preferably less than $6.5 \times 10^{-17}$ m$^3$ (5 µm diameter), more preferably about $4.2 \times 10^{-18}$ m$^3$ (2 µm diameter) and ideally about $9 \times 10^{-18}$ m$^3$ (2.6 µm diameter).

The effective DNA or RNA concentration in the microcapsules may be artificially increased by various methods that will be well-known to those versed in the art. These include, for example, the addition of volume excluding chemicals such as polyethylene glycols (PEG) and a variety of gene amplification techniques, including transcription using RNA polymerases including those from bacteria such as *E. coli* (Roberts, 1969; Blattner and Dahlberg, 1972; Roberts et al., 1975; Rosenberg et al., 1975), eukaryotes e.g. (Weil et al., 1979; Manley et al., 1983) and bacteriophage such as T7, T3 and SP6 (Melton et al., 1984); the polymerase chain reaction (PCR) (Saiki et al., 1988); Qb replicase amplification (Miele et al., 1983; Cahill et al., 1991; Chetverin and Spirin, 1995; Katanaev et al., 1995); the ligase chain reaction (LCR) (Landegren et al., 1988; Barany, 1991); and self-sustained sequence replication system (Fahy et al., 1991) and strand displacement amplification (Walker et al., 1992). Gene amplification techniques requiring thermal cycling such as PCR and LCR may be used if the emulsions and the in vitro transcription or coupled transcription-translation systems are thermostable (for example, the coupled transcription-translation systems can be made from a thermostable organism such as *Thermus aquaticus*).

Increasing the effective local nucleic acid concentration enables larger microcapsules to be used effectively. This allows a preferred practical upper limit to the microcapsule volume of about $5.2 \times 10^{-16}$ m$^3$ (corresponding to a sphere of diameter 10 µm).

The microcapsule size is preferably sufficiently large to accommodate all of the required components of the biochemical reactions that are needed to occur within the microcapsule. For example, in vitro, both transcription reactions and coupled transcription-translation reactions require a total nucleoside triphosphate concentration of about 2 mM.

For example, in order to transcribe a gene to a single short RNA molecule of 500 bases in length, this would require a minimum of 500 molecules of nucleoside triphosphate per microcapsule ($8.33 \times 10^{-22}$ moles). In order to constitute a 2 mM solution, this number of molecules is contained within a microcapsule of volume $4.17 \times 10^{-19}$ liters ($4.17 \times 10^{-22}$ m$^3$ which if spherical would have a diameter of 93 nm.

Furthermore, particularly in the case of reactions involving translation, it is to be noted that the ribosomes necessary for the translation to occur are themselves approximately 20 nm in diameter. Hence, the preferred lower limit for microcapsules is a diameter of approximately 0.1 µm (100 nm).

Therefore, the microcapsule volume is preferably of the order of between $5.2 \times 10^{-22}$ m$^3$ and $5.2 \times 10^{-16}$ m$^3$ corresponding to a sphere of diameter between 0.1 µm and 10 µm, more preferably of between about $5.2 \times 10^{-19}$ m3 and $6.5 \times 10^{-17}$ m$^3$ (1 µm and 5 µm). Sphere diameters of about 2.6 µm are most advantageous.

It is no coincidence that the preferred dimensions of the compartments (droplets of 2.6 µm mean diameter) closely resemble those of bacteria, for example, *Escherichia* are 1.1-1.5×2.0-6.0 µm rods and *Azotobacter* are 1.5-2.0 µm diameter ovoid cells. In its simplest form, Darwinian evolution is based on a 'one genotype one phenotype' mechanism. The concentration of a single compartmentalised gene, or genome, drops from 0.4 nM in a compartment of 2 µm diameter, to 25 pM in a compartment of 5 µm diameter. The prokaryotic transcription/translation machinery has evolved to operate in compartments of ~1-2 µm diameter, where single genes are at approximately nanomolar concentrations. A single gene, in a compartment of 2.6 µm diameter is at a concentration of 0.2 nM. This gene concentration is high enough for efficient translation. Compartmentalisation in such a volume also ensures that even if only a single molecule of the gene product is formed it is present at about 0.2 nM, which is important if the gene product is to have a modifying activity of the genetic element itself. The volume of the microcapsule is thus selected bearing in mind not only the requirements for transcription and translation of the genetic element, but also the modifying activity required of the gene product in the method of the invention.

The size of emulsion microcapsules may be varied simply by tailoring the emulsion conditions used to form the emulsion according to requirements of the selection system. The larger the microcapsule size, the larger is the volume that will be required to encapsulate a given genetic element library, since the ultimately limiting factor will be the size of the microcapsule and thus the number of microcapsules possible per unit volume.

The size of the microcapsules is selected not only having regard to the requirements of the transcription/translation system, but also those of the selection system employed for the genetic element. Thus, the components of the selection system, such as a chemical modification system, may require reaction volumes and/or reagent concentrations which are not optimal for transcription/translation. As set forth herein, such requirements may be accommodated by a secondary re-encapsulation step; moreover, they may be accommodated by selecting the microcapsule size in order to maximise transcription/translation and selection as a whole. Empirical determination of optimal microcapsule volume and reagent concentration, for example as set forth herein, is preferred.

A "genetic element" in accordance with the present invention is as described above. Preferably, a genetic element is a molecule or construct selected from the group consisting of a DNA molecule, an RNA molecule, a partially or wholly artificial nucleic acid molecule consisting of exclusively synthetic or a mixture of naturally-occurring and synthetic bases, any one of the foregoing linked to a polypeptide, and any one of the foregoing linked to any other molecular group or construct. Advantageously, the other molecular group or construct may be selected from the group consisting of nucleic acids, polymeric substances, particularly beads, for example polystyrene beads, and magnetic or paramagnetic substances such as magnetic or paramagnetic beads.

The nucleic acid portion of the genetic element may comprise suitable regulatory sequences, such as those required for efficient expression of the gene product, for example promoters, enhancers, translational initiation sequences, polyadenylation sequences, splice sites and the like.

As will be apparent from the following, in many cases the polypeptide or other molecular group or construct is a ligand or a substrate which directly or indirectly binds to or reacts with the gene product in order to alter the optical properties of the genetic element. This allows the sorting of the genetic element on the basis of the activity of the gene product. The ligand or substrate can be connected to the nucleic acid by a variety of means that will be apparent to those skilled in the art (see, for example, Hermanson, 1996).

One way in which the nucleic acid molecule may be linked to a ligand or substrate is through biotinylation. This can be done by PCR amplification with a 5'-biotinylation primer such that the biotin and nucleic acid are covalently linked.

The ligand or substrate can be attached to the modified nucleic acid by a variety of means that will be apparent to those of skill in the art (see, for example, Hermanson, 1996). A biotinylated nucleic acid may be coupled to a polystyrene or paramagnetic microbead (0.02 to approx. 5.0 µm in diameter) that is coated with avidin or streptavidin, that will therefore bind the nucleic acid with very high affinity. This bead can be derivatised with substrate or ligand by any suitable method such as by adding biotinylated substrate or by covalent coupling.

Alternatively, a biotinylated nucleic acid may be coupled to avidin or streptavidin complexed to a large protein molecule such as thyroglobulin (669 Kd) or ferritin (440 Kd). This complex can be derivatised with substrate or ligand, for example by covalent coupling to the E-amino group of lysines or through a non-covalent interaction such as biotin-avidin.

The substrate may be present in a form unlinked to the genetic element but containing an inactive "tag" that requires a further step to activate it such as photoactivation (e.g. of a "caged" biotin analogue, (Sundberg et al., 1995; Pirrung and Huang, 1996)). The catalyst to be selected then converts the substrate to product. The "tag" is then activated and the "tagged" substrate and/or product bound by a tag-binding molecule (e.g. avidin or streptavidin) complexed with the nucleic acid. The ratio of substrate to product attached to the nucleic acid via the "tag" will therefore reflect the ratio of the substrate and product in solution.

An alternative is to couple the nucleic acid to a product-specific antibody (or other product-specific molecule). In this scenario, the substrate (or one of the substrates) is present in each microcapsule unlinked to the genetic element, but has a molecular "tag" (for example biotin, DIG or DNP or a fluorescent group). When the catalyst to be selected converts the substrate to product, the product retains the "tag" and is then captured in the microcapsule by the product-specific antibody. In this way the genetic element only becomes associated with the "tag" when it encodes or produces an enzyme capable of converting substrate to product.

The terms "isolating", "sorting" and "selecting", as well as variations thereof, are used herein. Isolation, according to the present invention, refers to the process of separating an entity from a heterogeneous population, for example a mixture, such that it is free of at least one substance with which it was associated before the isolation process. In a preferred embodiment, isolation refers to purification of an entity essentially to homogeneity. Sorting of an entity refers to the process of preferentially isolating desired entities over undesired entities. In as far as this relates to isolation of the desired entities, the terms "isolating" and "sorting" are equivalent. The method of the present invention permits the sorting of desired genetic elements from pools (libraries or repertoires) of genetic elements which contain the desired genetic element. Selecting is used to refer to the process (including the sorting process) of isolating an entity according to a particular property thereof.

In a highly preferred application, the method of the present invention is useful for sorting libraries of genetic elements. The invention accordingly provides a method according to preceding aspects of the invention, wherein the genetic elements are isolated from a library of genetic elements encoding a repertoire of gene products. Herein, the terms "library", "repertoire" and "pool" are used according to their ordinary signification in the art, such that a library of genetic elements encodes a repertoire of gene products. In general, libraries are constructed from pools of genetic elements and have properties which facilitate sorting.

Initial selection of a genetic element from a genetic element library using the present invention will in most cases require the screening of a large number of variant genetic elements. Libraries of genetic elements can be created in a variety of different ways, including the following.

Pools of naturally occurring genetic elements can be cloned from genomic DNA or cDNA (Sambrook et al., 1989); for example, phage antibody libraries, made by PCR amplification repertoires of antibody genes from immunised or unimmunised donors have proved very effective sources of functional antibody fragments (Winter et al., 1994; Hoogenboom, 1997). Libraries of genes can also be made by encoding all (see for example Smith, 1985; Parmley and Smith, 1988) or part of genes (see for example Lowman et al., 1991) or pools of genes (see for example Nissim et al., 1994) by a randomised or doped synthetic oligonucleotide. Libraries can also be made by introducing mutations into a genetic element or pool of genetic elements 'randomly' by a variety of techniques in vivo, including; using mutator strains of bacteria such as *E. coli* mutD5 (Liao et al., 1986; Yamagishi et al., 1990; Low et al., 1996); using the antibody hypermutation system of B-lymphocytes (Yelamos et al., 1995). Random mutations can also be introduced both in vivo and in vitro by chemical mutagens, and ionising or UV irradiation (see Friedberg et al., 1995), or incorporation of mutagenic base analogues (Freese, 1959; Zaccolo et al., 1996). Random' mutations can also be introduced into genes in vitro during polymerisation for example by using error-prone polymerases (Leung et al., 1989).

Further diversification can be introduced by using homologous recombination either in vivo (see Kowalczykowski et al., 1994) or in vitro (Stemmer, 1994a; Stemmer, 1994b).

According to a further aspect of the present invention, therefore, there is provided a method of in vitro evolution comprising the steps of:
(a) selecting one or more genetic elements from a genetic element library according to the present invention;
(b) mutating the selected genetic element(s) in order to generate a further library of genetic elements encoding a repertoire to gene products; and
(c) iteratively repeating steps (a) and (b) in order to obtain a gene product with enhanced activity.

Mutations may be introduced into the genetic elements(s) as set forth above.

The genetic elements according to the invention advantageously encode enzymes, preferably of pharmacological or industrial interest, activators or inhibitors, especially of biological systems, such as cellular signal transduction mechanisms, antibodies and fragments thereof, and other binding agents (e.g. transcription factors) suitable for diagnostic and therapeutic applications. In a preferred aspect, therefore, the invention permits the identification and isolation of clinically or industrially useful products. In a further aspect of the invention, there is provided a product when isolated by the method of the invention.

The selection of suitable encapsulation conditions is desirable. Depending on the complexity and size of the library to be screened, it may be beneficial to set up the encapsulation procedure such that 1 or less than 1 genetic element is encapsulated per microcapsule. This will provide the greatest power of resolution. Where the library is larger and/or more complex, however, this may be impracticable; it may be preferable to encapsulate several genetic elements together and rely on repeated application of the method of the invention to achieve sorting of the desired activity. A combination of encapsulation procedures may be used to obtain the desired enrichment.

Theoretical studies indicate that the larger the number of genetic element variants created the more likely it is that a molecule will be created with the properties desired (see Perelson and Oster, 1979 for a description of how this applies to repertoires of antibodies). Recently it has also been confirmed practically that larger phage-antibody repertoires do indeed give rise to more antibodies with better binding affinities than smaller repertoires (Griffiths et al., 1994). To ensure that rare variants are generated and thus are capable of being selected, a large library size is desirable. Thus, the use of optimally small microcapsules is beneficial.

The largest repertoire created to date using methods that require an in vivo step (phage-display and LacI systems) has been a $1.6 \times 10^{11}$ clone phage-peptide library which required the fermentation of 15 liters of bacteria (Fisch et al., 1996). SELEX experiments are often carried out on very large numbers of variants (up to $10^{15}$).

Using the present invention, at a preferred microcapsule diameter of 2.6 µm, a repertoire size of at least $10^{11}$ can be selected using 1 ml aqueous phase in a 20 ml emulsion.

In addition to the genetic elements described above, the microcapsules according to the invention will comprise further components required for the sorting process to take place. Other components of the system will for example comprise those necessary for transcription and/or translation of the genetic element. These are selected for the requirements of a specific system from the following; a suitable buffer, an in vitro transcription/replication system and/or an in vitro translation system containing all the necessary ingredients, enzymes and cofactors, RNA polymerase, nucleotides, nucleic acids (natural or synthetic), transfer RNAs, ribosomes and amino acids, and the substrates of the reaction of interest in order to allow selection of the modified gene product.

A suitable buffer will be one in which all of the desired components of the biological system are active and will therefore depend upon the requirements of each specific reaction system. Buffers suitable for biological and/or chemical reactions are known in the art and recipes provided in various laboratory texts, such as Sambrook et al., 1989.

The in vitro translation system will usually comprise a cell extract, typically from bacteria (Zubay, 1973; Zubay, 1980; Lesley et al., 1991; Lesley, 1995), rabbit reticulocytes (Pelham and Jackson, 1976), or wheat germ (Anderson et al., 1983). Many suitable systems are commercially available (for example from Promega) including some which will allow coupled transcription/translation (all the bacterial systems and the reticulocyte and wheat germ TNT™ extract systems from Promega). The mixture of amino acids used may include synthetic amino acids if desired, to increase the possible number or variety of proteins produced in the library. This can be accomplished by charging tRNAs with artificial amino acids and using these tRNAs for the in vitro translation of the proteins to be selected (Ellman et al., 1991; Benner, 1994; Mendel et al., 1995).

After each round of selection the enrichment of the pool of genetic elements for those encoding the molecules of interest can be assayed by non-compartmentalised in vitro transcription/replication or coupled transcription-translation reactions. The selected pool is cloned into a suitable plasmid vector and RNA or recombinant protein is produced from the individual clones for further purification and assay.

In a preferred aspect, the internal environment of a microcapsule may be altered by addition of reagents to the oil phase of the emulsion. The reagents diffuse through the oil phase to the aqueous microcapsule environment. Preferably, the reagents are at least partly water-soluble, such that a proportion thereof is distributed from the oil phase to the aqueous microcapsule environment. Advantageously, the reagents are substantially insoluble in the oil phase. Reagents are preferably mixed into the oil phase by mechanical mixing, for example vortexing.

The reagents which may be added via the oil phase include substrates, buffering components, factors and the like. In particular, the internal pH of microcapsules may be altered in situ by adding acidic or basic components to the oil phase.

The invention moreover relates to a method for producing a gene product, once a genetic element encoding the gene product has been sorted by the method of the invention. Clearly, the genetic element itself may be directly expressed by conventional means to produce the gene product. However, alternative techniques may be employed, as will be apparent to those skilled in the art. For example, the genetic information incorporated in the gene product may be incorporated into a suitable expression vector, and expressed therefrom.

The invention also describes the use of conventional screening techniques to identify compounds which are capable of interacting with the gene products identified by the first aspect of the invention. In preferred embodiments, gene product encoding nucleic acid is incorporated into a vector, and introduced into suitable host cells to produce transformed cell lines that express the gene product. The resulting cell lines can then be produced for reproducible qualitative and/or quantitative analysis of the effect(s) of potential drugs affecting gene product function. Thus gene product expressing cells may be employed for the identification of compounds, particularly small molecular weight compounds, which modulate the function of gene product. Thus host cells expressing gene product are useful for drug screening and it is a further object of the present invention to provide a method for identifying compounds which modulate the activity of the gene product, said method comprising exposing cells containing heterologous DNA encoding gene product, wherein said cells produce functional gene product, to at least one compound or mixture of compounds or signal whose ability to modulate the activity of said gene product is sought to be determined, and thereafter monitoring said cells for changes caused by said modulation. Such an assay enables the identification of modulators, such as agonists, antagonists and allosteric modulators, of the gene product. As used herein, a compound or signal that modulates the activity of gene product refers to a compound that alters the activity of gene product in such a way that the activity of the gene product is different in the presence of the compound or signal (as compared to the absence of said compound or signal).

Cell-based screening assays can be designed by constructing cell lines in which the expression of a reporter protein, i.e. an easily assayable protein, such as □-galactosidase, chloramphenicol acetyltransferase (CAT), green fluorescent protein (GFP) or luciferase, is dependent on gene product.

Such an assay enables the detection of compounds that directly modulate gene product function, such as compounds that antagonise gene product, or compounds that inhibit or potentiate other cellular functions required for the activity of gene product.

The present invention also provides a method to exogenously affect gene product dependent processes occurring in cells. Recombinant gene product producing host cells, e.g. mammalian cells, can be contacted with a test compound, and the modulating effect(s) thereof can then be evaluated by comparing the gene product-mediated response in the presence and absence of test compound, or relating the gene product-mediated response of test cells, or control cells (i.e., cells that do not express gene product), to the presence of the compound.

In a further aspect, the invention relates to a method for optimising a production process which involves at least one step which is facilitated by a polypeptide. For example, the step may be a catalytic step, which is facilitated by an enzyme. Thus, the invention provides a method for preparing a compound or compounds comprising the steps of:
 (a) providing a synthesis protocol wherein at least one step is facilitated by a polypeptide;
 (b) preparing genetic elements encoding variants of the polypeptide which facilitates this step, the expression of which may result, directly or indirectly, in the modification of the optical properties of the genetic elements;
 (c) compartmentalising genetic elements into microcapsules;
 (d) expressing the genetic elements to produce their respective gene products within the microcapsules;
 (e) sorting the genetic elements which produce polypeptide gene product(s) having the desired activity using the changed optical properties of the genetic elements; and
 (f) preparing the compound or compounds using the polypeptide gene product identified in (g) to facilitate the relevant step of the synthesis.

By means of the invention, enzymes involved in the preparation of a compound may be optimised by selection for optimal activity. The procedure involves the preparation of variants of the polypeptide to be screened, which equate to a library of polypeptides as refereed to herein. The variants may be prepared in the same manner as the libraries discussed elsewhere herein.

The size of emulsion microcapsules may be varied simply by tailoring the emulsion conditions used to form the emulsion according to requirements of the screening system. The larger the microcapsule size, the larger is the volume that will be required to encapsulate a given library, since the ultimately limiting factor will be the size of the microcapsule and thus the number of microcapsules possible per unit volume.

Water-in-oil emulsions can be re-emulsified to create water-in-oil-in water double emulsions with an external (continuous) aqueous phase. These double emulsions can be analysed and, optionally, sorted using a flow cytometer (Bernath et al., 2004).

Highly monodisperse microcapsules can be produced using microfluidic techniques. For example, water-in-oil emulsions with less than 1.5% polydispersity can be generated by droplet break off in a co-flowing steam of oil (Umbanhowar et al., 2000). Microfluidic systems can also be used for laminar-flow of aqueous microdroplets dispersed in a stream of oil in microfluidic channels (Thorsen et al., 2001). This allows the construction of microfluidic devices for flow analysis and, optionally, flow sorting of microdroplets (Fu et al., 2002).

Advantageously, highly monodisperse microcapsules can be formed using systems and methods for the electronic control of fluidic species. One aspect of the invention relates to systems and methods for producing droplets of fluid surrounded by a liquid. The fluid and the liquid may be essentially immiscible in many cases, i.e., immiscible on a time scale of interest (e.g., the time it takes a fluidic droplet to be transported through a particular system or device). In certain cases, the droplets may each be substantially the same shape or size, as further described below. The fluid may also contain other species, for example, certain molecular species (e.g., as further discussed below), cells, particles, etc.

In one set of embodiments, electric charge may be created on a fluid surrounded by a liquid, which may cause the fluid to separate into individual droplets within the liquid. In some embodiments, the fluid and the liquid may be present in a channel, e.g., a microfluidic channel, or other constricted space that facilitates application of an electric field to the fluid (which may be "AC" or alternating current, "DC" or direct current etc.), for example, by limiting movement of the fluid with respect to the liquid. Thus, the fluid can be present as a series of individual charged and/or electrically inducible droplets within the liquid. In one embodiment, the electric force exerted on the fluidic droplet may be large enough to cause the droplet to move within the liquid. In some cases, the electric force exerted on the fluidic droplet may be used to direct a desired motion of the droplet within the liquid, for example, to or within a channel or a microfluidic channel (e.g., as further described herein), etc. As one example, in apparatus 5 in FIG. 3A, droplets 15 created by fluid source 10 can be electrically charged using an electric filed created by electric field generator 20.

Electric charge may be created in the fluid within the liquid using any suitable technique, for example, by placing the fluid within an electric field (which may be AC, DC, etc.), and/or causing a reaction to occur that causes the fluid to have an electric charge, for example, a chemical reaction, an ionic reaction, a photocatalyzed reaction, etc. In one embodiment, the fluid is an electrical conductor. As used herein, a "conductor" is a material having a conductivity of at least about the conductivity of 18 megohm (MOhm or MΩ) water. The liquid surrounding the fluid may have a conductivity less than that of the fluid. For instance, the liquid may be an insulator, relative to the fluid, or at least a "leaky insulator," i.e., the liquid is able to at least partially electrically insulate the fluid for at least a short period of time. Those of ordinary skill in the art will be able to identify the conductivity of fluids. In one non-limiting embodiment, the fluid may be substantially hydrophilic, and the liquid surrounding the fluid may be substantially hydrophobic.

In some embodiments, the charge created on the fluid (for example, on a series of fluidic droplets) may be at least about $10^{-22}$ C/micrometer$^3$. In certain cases, the charge may be at least about $10^{-21}$ C/micrometer$^3$, and in other cases, the charge may be at least about $10^{-20}$ C/micrometer$^3$, at least about $10^{-19}$ C/micrometer$^3$, at least about $10^{-18}$ C/micrometer$^3$, at least about $10^{-17}$ C/micrometer$^3$, at least about $10^{-16}$ C/micrometer$^3$, at least about $10^{-15}$ C/micrometer$^3$, at least about $10^{-14}$ C/micrometer$^3$, at least about $10^{-13}$ C/micrometer$^3$, at least about $10^{-12}$ C/micrometer$^3$, at least about $10^{-11}$ C/micrometer$^3$, at least about $10^{-10}$ C/micrometer$^3$, or at least about $10^{-9}$ C/micrometer$^3$ or more. In certain embodiments, the charge created on the fluid may be at least about $10^{-21}$ C/micrometer$^2$, and in some cases, the charge may be at least about $10^{-20}$ C/micrometer$^2$, at least about $10^{-19}$ C/micrometer$^2$, at least about $10^{-18}$ C/micrometer$^2$, at least about $10^{-17}$ C/micrometer$^2$, at least about $10^{-16}$ C/micrometer$^2$, at least about $10^{-15}$ C/micrometer$^2$, at least about $10^{-14}$ C/micrometer$^2$, or at least about $10^{-13}$ C/micrometer$^2$ or more. In other embodiments, the charge may be at least about $10^{-14}$ C/droplet, and, in some cases, at least about $10^{-13}$ C/droplet, in other cases at least about $10^{-12}$ C/droplet, in other cases at least about $10^{-11}$ C/droplet, in other cases at least about $10^{-10}$ C/droplet, or in still other cases at least about $10^{-9}$ C/droplet.

The electric field, in some embodiments, is generated from an electric field generator, i.e., a device or system able to create an electric field that can be applied to the fluid. The electric field generator may produce an AC field (i.e., one that varies periodically with respect to time, for example, sinusoidally, sawtooth, square, etc.), a DC field (i.e., one that is constant with respect to time), a pulsed field, etc. The electric field generator may be constructed and arranged to create an electric field within a fluid contained within a channel or a microfluidic channel. The electric field generator may be integral to or separate from the fluidic system containing the channel or microfluidic channel, according to some embodiments. As used herein, "integral" means that portions of the components integral to each other are joined in such a way that the components cannot be manually separated from each other without cutting or breaking at least one of the components.

Techniques for producing a suitable electric field (which may be AC, DC, etc.) are known to those of ordinary skill in the art. For example, in one embodiment, an electric field is produced by applying voltage across a pair of electrodes, which may be positioned on or embedded within the fluidic system (for example, within a substrate defining the channel or microfluidic channel), and/or positioned proximate the fluid such that at least a portion of the electric field interacts with the fluid. The electrodes can be fashioned from any suitable electrode material or materials known to those of ordinary skill in the art, including, but not limited to, silver, gold, copper, carbon, platinum, copper, tungsten, tin, cadmium, nickel, indium tin oxide ("ITO"), etc., as well as combinations thereof. In some cases, transparent or substantially transparent electrodes can be used. In certain embodiments, the electric field generator can be constructed and arranged (e.g., positioned) to create an electric field applicable to the fluid of at least about 0.01 V/micrometer, and, in some cases, at least about 0.03 V/micrometer, at least about 0.05 V/micrometer, at least about 0.08 V/micrometer, at least about 0.1 V/micrometer, at least about 0.3 V/micrometer, at least about 0.5 V/micrometer, at least about 0.7 V/micrometer, at least about 1 V/micrometer, at least about 1.2 V/micrometer, at least about 1.4 V/micrometer, at least about 1.6 V/micrometer, or at least about 2 V/micrometer. In some embodiments, even higher electric field intensities may be used, for example, at least about 2 V/micrometer, at least about 3 V/micrometer, at least about 5 V/micrometer, at least about 7 V/micrometer, or at least about 10 V/micrometer or more.

In some embodiments, an electric field may be applied to fluidic droplets to cause the droplets to experience an electric force. The electric force exerted on the fluidic droplets may be, in some cases, at least about $10^{-16}$ N/micrometer$^3$. In certain cases, the electric force exerted on the fluidic droplets may be greater, e.g., at least about $10^{-15}$ N/micrometer$^3$, at least about $10^{-14}$ N/micrometer$^3$, at least about $10^{-13}$ N/micrometer$^3$, at least about $10^{-12}$ N/micrometer 3, at least about $10^{-11}$ N/micrometer 3, at least about $10^{-10}$ N/micrometer$^3$, at least about $10^{-9}$ N/micrometer$^3$, at least about $10^{-8}$ N/micrometer$^3$, or at least about $10^{-7}$ N/micrometer$^3$ or more. In other embodiments, the electric force exerted on the fluidic droplets, relative to the surface area of the fluid, may be at least about $10^{-15}$ N/micrometer$^2$, and in some cases, at least about $10^{-14}$ N/micrometer$^2$, at least about $10^{-13}$ N/micrometer$^2$, at least about $10^{-12}$ N/micrometer$^2$, at least about $10^{-11}$ N/micrometer$^2$, at least about $10^{-10}$ N/micrometer$^2$, at least about $10^{-9}$ N/micrometer$^2$, at least about $10^{-8}$ N/micrometer$^2$, at least about $10^{-7}$ N/micrometer$^2$, or at least about $10^{-6}$ N/micrometer$^2$ or more. In yet other embodiments, the electric force exerted on the fluidic droplets may be at least about $10^{-9}$ N, at least about $10^{-8}$ N, at least about $10^{-7}$ N, at least about $10^{-6}$ N, at least about $10^{-5}$ N, or at least about $10^{-4}$ N or more in some cases.

In some embodiments of the invention, systems and methods are provided for at least partially neutralizing an electric charge present on a fluidic droplet, for example, a fluidic droplet having an electric charge, as described above. For example, to at least partially neutralize the electric charge, the fluidic droplet may be passed through an electric field and/or brought near an electrode, e.g., using techniques such as those described herein. Upon exiting of the fluidic droplet from the electric field (i.e., such that the electric field no longer has a strength able to substantially affect the fluidic droplet), and/or other elimination of the electric field, the fluidic droplet may become electrically neutralized, and/or have a reduced electric charge.

In another set of embodiments, droplets of fluid can be created from a fluid surrounded by a liquid within a channel by altering the channel dimensions in a manner that is able to induce the fluid to form individual droplets. The channel may, for example, be a channel that expands relative to the direction of flow, e.g., such that the fluid does not adhere to the channel walls and forms individual droplets instead, or a channel that narrows relative to the direction of flow, e.g., such that the fluid is forced to coalesce into individual droplets. One example is shown in FIG. 7A, where channel 510 includes a flowing fluid 500 (flowing downwards), surrounded by liquid 505. Channel 510 narrows at location 501, causing fluid 500 to form a series of individual fluidic droplets 515. In other embodiments, internal obstructions may also be used to cause droplet formation to occur. For instance, baffles, ridges, posts, or the like may be used to disrupt liquid flow in a manner that causes the fluid to coalesce into fluidic droplets.

In some cases, the channel dimensions may be altered with respect to time (for example, mechanically or electromechanically, pneumatically, etc.) in such a manner as to cause the formation of individual fluidic droplets to occur. For example, the channel may be mechanically contracted ("squeezed") to cause droplet formation, or a fluid stream may be mechanically disrupted to cause droplet formation, for example, through the use of moving baffles, rotating blades, or the like. As a non-limiting example, in FIG. 7B, fluid 500 flows through channel 510 in a downward direction. Fluid 500 is surrounded by liquid 505. Piezoelectric devices 520 positioned near or integral to channel 510 may then mechanically constrict or "squeeze" channel 510, causing fluid 500 to break up into individual fluidic droplets 515.

Figure 14A:
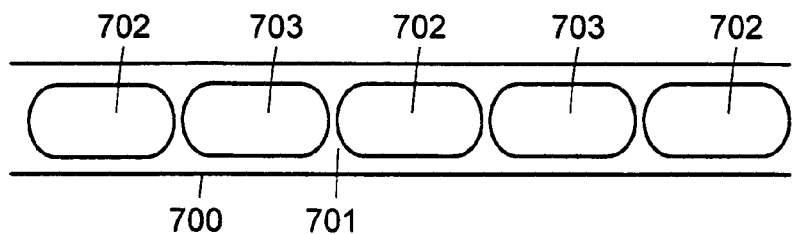
FIGS. 14a-14c are illustrations of the formation and maintenance of microfluidic droplets using three immiscible liquids.
Figure 14B:
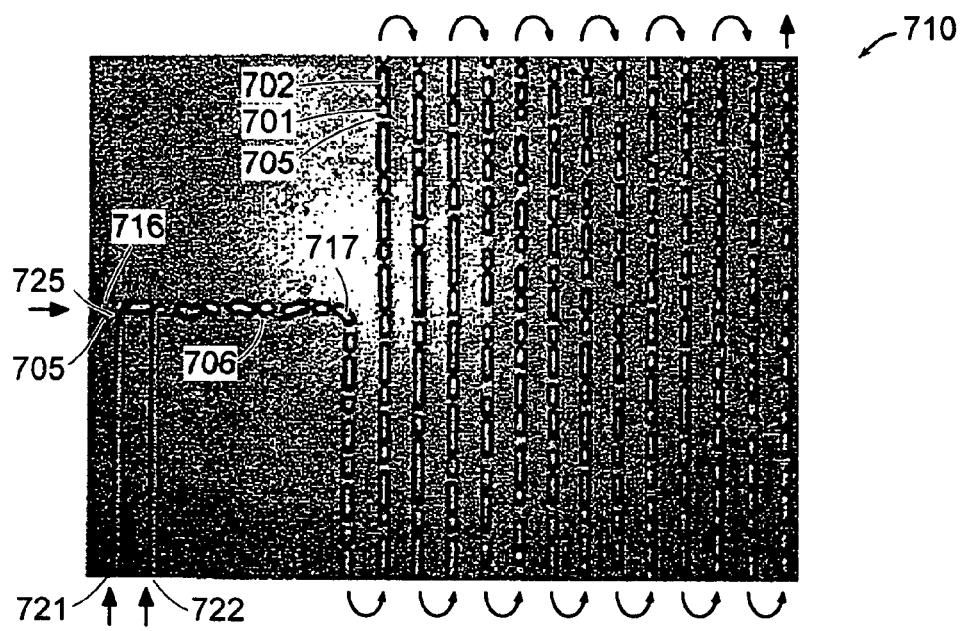
Figure 14C:
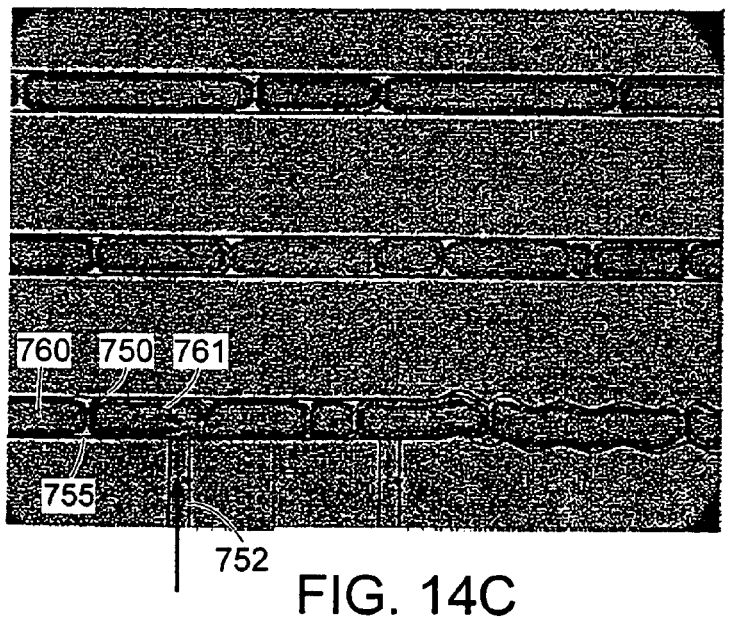

In yet another set of embodiments, individual fluidic droplets can be created and maintained in a system comprising three essentially mutually immiscible fluids (i.e., immiscible on a time scale of interest), where one fluid is a liquid carrier, and the second fluid and the third fluid alternate as individual fluidic droplets within the liquid carrier. In such a system, surfactants are not necessarily required to ensure separation of the fluidic droplets of the second and third fluids. As an example, with reference to FIG. 14A, within channel 700, a first fluid 701 and a second fluid 702 are each carried within liquid carrier 705. First fluid 701 and second fluid 702 alternate as a series of alternating, individual droplets, each carried by liquid carrier 705 within channel 700. As the first fluid, the second fluid, and the liquid carrier are all essentially mutually immiscible, any two of the fluids (or all three fluids) can come into contact without causing droplet coalescence to occur. A photomicrograph of an example of such a system is shown in FIG. 14B, illustrating first fluid 701 and second fluid 702, present as individual, alternating droplets, each contained within liquid carrier 705.

One example of a system involving three essentially mutually immiscible fluids is a silicone oil, a mineral oil, and an aqueous solution (i.e., water, or water containing one or more other species that are dissolved and/or suspended therein, for example, a salt solution, a saline solution, a suspension of water containing particles or cells, or the like). Another example of a system is a silicone oil, a fluorocarbon oil, and an aqueous solution. Yet another example of a system is a hydrocarbon oil (e.g., hexadecane), a fluorocarbon oil, and an aqueous solution. In these examples, any of these fluids may be used as the liquid carrier. Non-limiting examples of suitable fluorocarbon oils include octadecafluorodecahydro naphthalene:

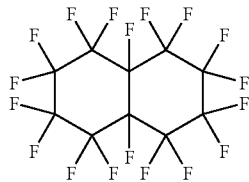

or 1-(1,2,2,3,3,4,4,5,5,6,6-undecafluorocyclohexyl)ethanol:

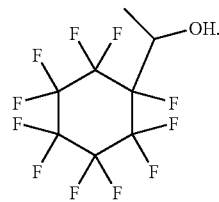

A non-limiting example of such a system is illustrated in FIG. 14B. In this figure, fluidic network 710 includes a channel containing liquid carrier 705, and first fluid 701 and second fluid 702. Liquid carrier 705 is introduced into fluidic network 710 through inlet 725, while first fluid 701 is introduced through inlet 721, and second fluid 702 is introduced through inlet 722. Channel 716 within fluidic network 710 contains liquid carrier 715 introduced from inlet 725. Initially, first fluid 701 is introduced into liquid carrier 705, forming fluidic droplets therein. Next, second fluid 702 is introduced into liquid 705, forming fluidic droplets therein that are interspersed with the fluidic droplets containing first fluid 701. Thus, upon reaching channel 717, liquid carrier 705 contains a first set of fluidic droplets containing first fluid 701, interspersed with a second set of fluidic droplets containing second fluid 702. In the embodiment illustrated, channel 706 optionally comprises a series of bends, which may allow mixing to occur within each of the fluidic droplets, as further discussed below. However, it should be noted that in this embodiment, since first fluid 701 and second fluid 702 are essentially immiscible, significant fusion and/or mixing of the droplets containing first fluid 701 with the droplets containing second fluid 702 is not generally expected.

Other examples of the production of droplets of fluid surrounded by a liquid are described in International Patent Application Serial No. PCT/US2004/010903, filed Apr. 9, 2004 by Link, et al. and International Patent Application Serial No. PCT/US03/20542, filed Jun. 30, 2003 by Stone, et al., published as WO 2004/002627 on Jan. 8, 2004, each incorporated herein by reference.

In some embodiments, the fluidic droplets may each be substantially the same shape and/or size. The shape and/or size can be determined, for example, by measuring the average diameter or other characteristic dimension of the droplets. The term "determining," as used herein, generally refers to the analysis or measurement of a species, for example, quantitatively or qualitatively, and/or the detection of the presence or absence of the species. "Determining" may also refer to the analysis or measurement of an interaction between two or more species, for example, quantitatively or qualitatively, or by detecting the presence or absence of the interaction. Examples of suitable techniques include, but are not limited to, spectroscopy such as infrared, absorption, fluorescence, UV/visible, FTIR ("Fourier Transform Infrared Spectroscopy"), or Raman; gravimetric techniques; ellipsometry; piezoelectric measurements; immunoassays; electrochemical measurements; optical measurements such as optical density measurements; circular dichroism; light scattering measurements such as quasielectric light scattering; polarimetry; refractometry; or turbidity measurements.

The "average diameter" of a plurality or series of droplets is the arithmetic average of the average diameters of each of the droplets. Those of ordinary skill in the art will be able to determine the average diameter (or other characteristic dimension) of a plurality or series of droplets, for example, using laser light scattering, microscopic examination, or other known techniques. The diameter of a droplet, in a non-spherical droplet, is the mathematically-defined average diameter of the droplet, integrated across the entire surface. The average diameter of a droplet (and/or of a plurality or series of droplets) may be, for example, less than about 1 mm, less than about 500 micrometers, less than about 200 micrometers, less than about 100 micrometers, less than about 75 micrometers, less than about 50 micrometers, less than about 25 micrometers, less than about 10 micrometers, or less than about 5 micrometers in some cases. The average diameter may also be at least about 1 micrometer, at least about 2 micrometers, at least about 3 micrometers, at least about 5 micrometers, at least about 10 micrometers, at least about 15 micrometers, or at least about 20 micrometers in certain cases.

In certain instances, the invention provides for the production of droplets consisting essentially of a substantially uniform number of entities of a species therein (i.e., molecules, compounds, cells, genetic elements, particles, etc.). For example, about 90%, about 93%, about 95%, about 97%, about 98%, or about 99%, or more of a plurality or series of droplets may each contain the same number of entities of a particular species. For instance, a substantial number of fluidic droplets produced, e.g., as described above, may each contain 1 entity, 2 entities, 3 entities, 4 entities, 5 entities, 7 entities, 10 entities, 15 entities, 20 entities, 25 entities, 30 entities, 40 entities, 50 entities, 60 entities, 70 entities, 80 entities, 90 entities, 100 entities, etc., where the entities are molecules or macromolecules, cells, particles, etc. In some cases, the droplets may each independently contain a range of entities, for example, less than 20 entities, less than 15 entities, less than 10 entities, less than 7 entities, less than 5 entities, or less than 3 entities in some cases. In one set of embodiments, in a liquid containing droplets of fluid, some of which contain a species of interest and some of which do not contain the species of interest, the droplets of fluid may be screened or sorted for those droplets of fluid containing the species as further described below (e.g., using fluorescence or other techniques such as those described above), and in some cases, the droplets may be screened or sorted for those droplets of fluid containing a particular number or range of entities of the species of interest, e.g., as previously described. Thus, in some cases, a plurality or series of fluidic droplets, some of which contain the species and some of which do not, may be enriched (or depleted) in the ratio of droplets that do contain the species, for example, by a factor of at least about 2, at least about 3, at least about 5, at least about 10, at least about 15, at least about 20, at least about 50, at least about 100, at least about 125, at least about 150, at least about 200, at least about 250, at least about 500, at least about 750, at least about 1000, at least about 2000, or at least about 5000 or more in some cases. In other cases, the enrichment (or depletion) may be in a ratio of at least about $10^4$, at least about $10^5$, at least about $10^6$, at least about $10^7$, at least about $10^8$, at least about $10^9$, at least about $10^{10}$, at least about $10^{11}$, at least about $10^{12}$, at least about $10^{13}$, at least about $10^{14}$, at least about $10^{15}$, or more. For example, a fluidic droplet containing a particular species may be selected from a library of fluidic droplets containing various species, where the library may have about $10^5$, about $10^6$, about $10^7$, about $10^8$, about $10^9$, about $10^{10}$, about $10^{11}$, about $10^{12}$, about $10^{13}$, about $10^{14}$, about $10^{15}$, or more items, for example, a DNA library, an RNA library, a protein library, a combinatorial chemistry library, a library of genetic elements, etc. In certain embodiments, the droplets carrying the species may then be fused, reacted, or otherwise used or processed, etc., as further described below, for example, to initiate or determine a reaction.

The use of microfluidic handling to create microcapsoules according to the invention has a number of advantages:
(a) They allow the formation of highly monodisperse microcapsules (<1.5% polydispersity), each of which functions as an almost identical, very small microreactor;
(b) The microcapsules can have volumes ranging from about 1 femtoliter to about 1 nanoliter;
(c) Compartmentalisation in microcapsules prevents diffusion and dispersion due to parabolic flow;
(d) By using a perfluorocarbon carrier fluid it is possible to prevent exchange of molecules between microcapsules;
(e) Reagents in microcapsules cannot react or interact with the fabric of the microchannels as they are separated by a layer of inert perfluorocarbon carrier fluid.
(f) Microcapsules can be created at up to 10,000 per second and screened using optical methods at the same rate. This is a throughput of ~$10^9$ per day.

Microcapsules (or droplets; the terms may be used intechangeably for the purposes envisaged herein) can, advantageously, be fused or split. For example, aqueous microdroplets can be merged and split using microfluidics systems (Link et al., 2004; Song et al., 2003). Microcapsule fusion allows the mixing of reagents. Fusion, for example, of a microcapsule containing the genetic element with a microcapsule containing a transcription factor could initiate transcription of the genetic information. Microcapsule splitting allows single microcapsules to be split into two or more smaller microcapsules. For example a single microcapsule containing a ragent can be split into multiple microcapsules which can then each be fused with a different microcapsule containing a different reagent or genetic element. A single microcapsule containing a reagent can also be split into multiple microcapsules which can then each be fused with a different microcapsule containing a different genetic element, or other reagents, for example at different concentrations.

In one aspect, the invention relates to microfluidic systems and methods for splitting a fluidic droplet into two or more droplets. The fluidic droplet may be surrounded by a liquid, e.g., as previously described, and the fluid and the liquid are essentially immiscible in some cases. The two or more droplets created by splitting the original fluidic droplet may each be substantially the same shape and/or size, or the two or more droplets may have different shapes and/or sizes, depending on the conditions used to split the original fluidic droplet. In many cases, the conditions used to split the original fluidic droplet can be controlled in some fashion, for example, manually or automatically (e.g., with a processor, as discussed below). In some cases, each droplet in a plurality or series of fluidic droplets may be independently controlled. For example, some droplets may be split into equal parts or unequal parts, while other droplets are not split.

According to one set of embodiments, a fluidic droplet can be split using an applied electric field. The electric field may be an AC field, a DC field, etc. The fluidic droplet, in this embodiment, may have a greater electrical conductivity than the surrounding liquid, and, in some cases, the fluidic droplet may be neutrally charged. In some embodiments, the droplets produced from the original fluidic droplet are of approximately equal shape and/or size. In certain embodiments, in an applied electric field, electric charge may be urged to migrate from the interior of the fluidic droplet to the surface to be distributed thereon, which may thereby cancel the electric field experienced in the interior of the droplet. In some embodiments, the electric charge on the surface of the fluidic droplet may also experience a force due to the applied electric field, which causes charges having opposite polarities to migrate in opposite directions. The charge migration may, in some cases, cause the drop to be pulled apart into two separate fluidic droplets. The electric field applied to the fluidic droplets may be created, for example, using the techniques described above, such as with a reaction an electric field generator, etc.

Figure 1B:
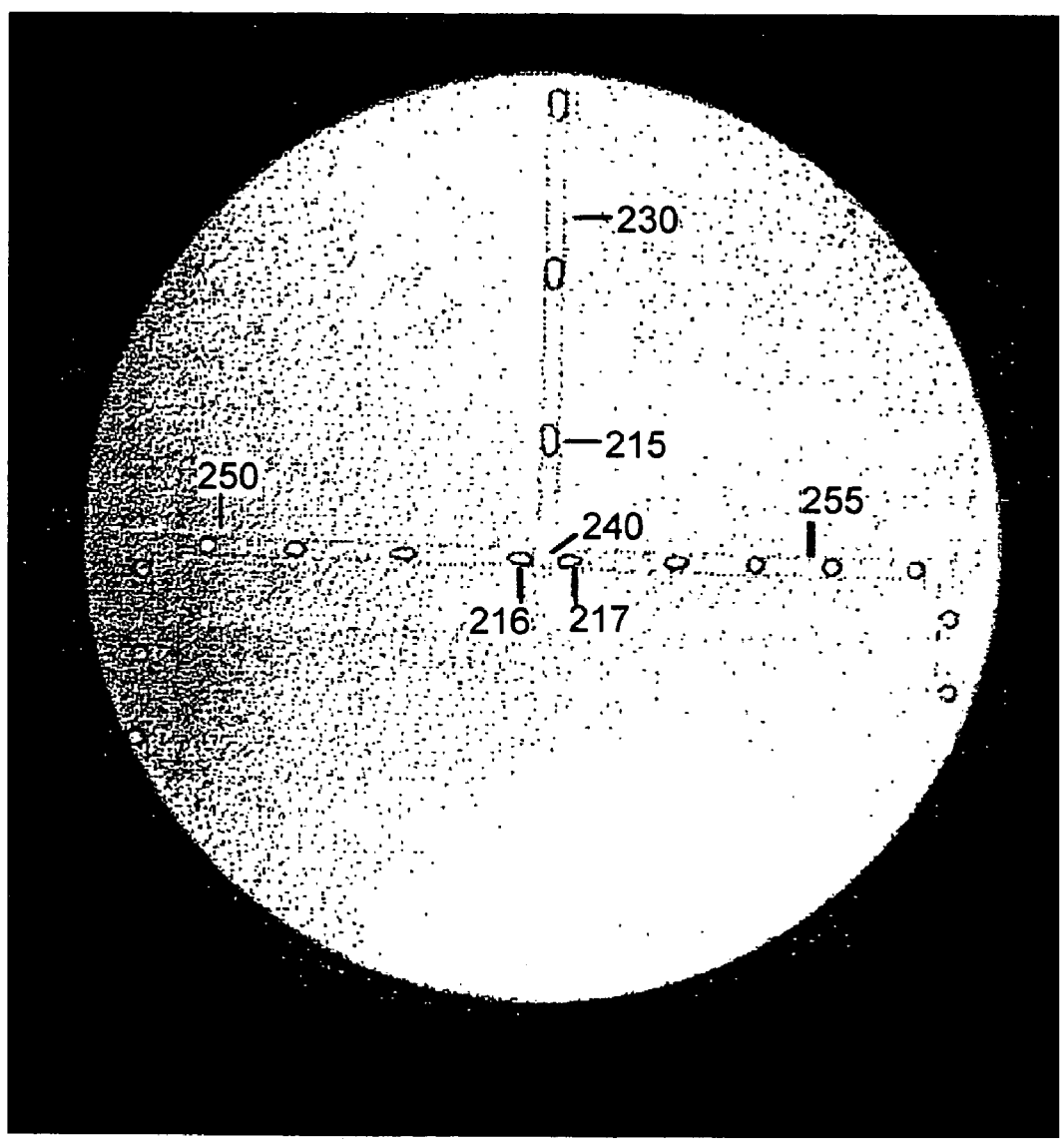

As a non-limiting example, in FIG. 1A, where no electric field is applied, fluidic droplets 215 contained in channel 230 are carried by a surrounding liquid, which flows towards intersection 240, leading to channels 250 and 255. In this example, the surrounding liquid flows through channels 250 and 255 at equal flowrates. Thus, at intersection 240, fluidic droplets 215 do not have a preferred orientation or direction, and move into exit channels 250 and 255 with equal probability due to the surrounding liquid flow. In contrast, in FIG. 1B, while the surrounding liquid flows in the same fashion as FIG. 1A, under the influence of an applied electric field of 1.4 V/micrometers, fluidic droplets 215 are split into two droplets at intersection 240, forming new droplets 216 and 217. Droplet 216 moves to the left in channel 250, while droplet 217 moves to the right in channel 255.

Figure 5:
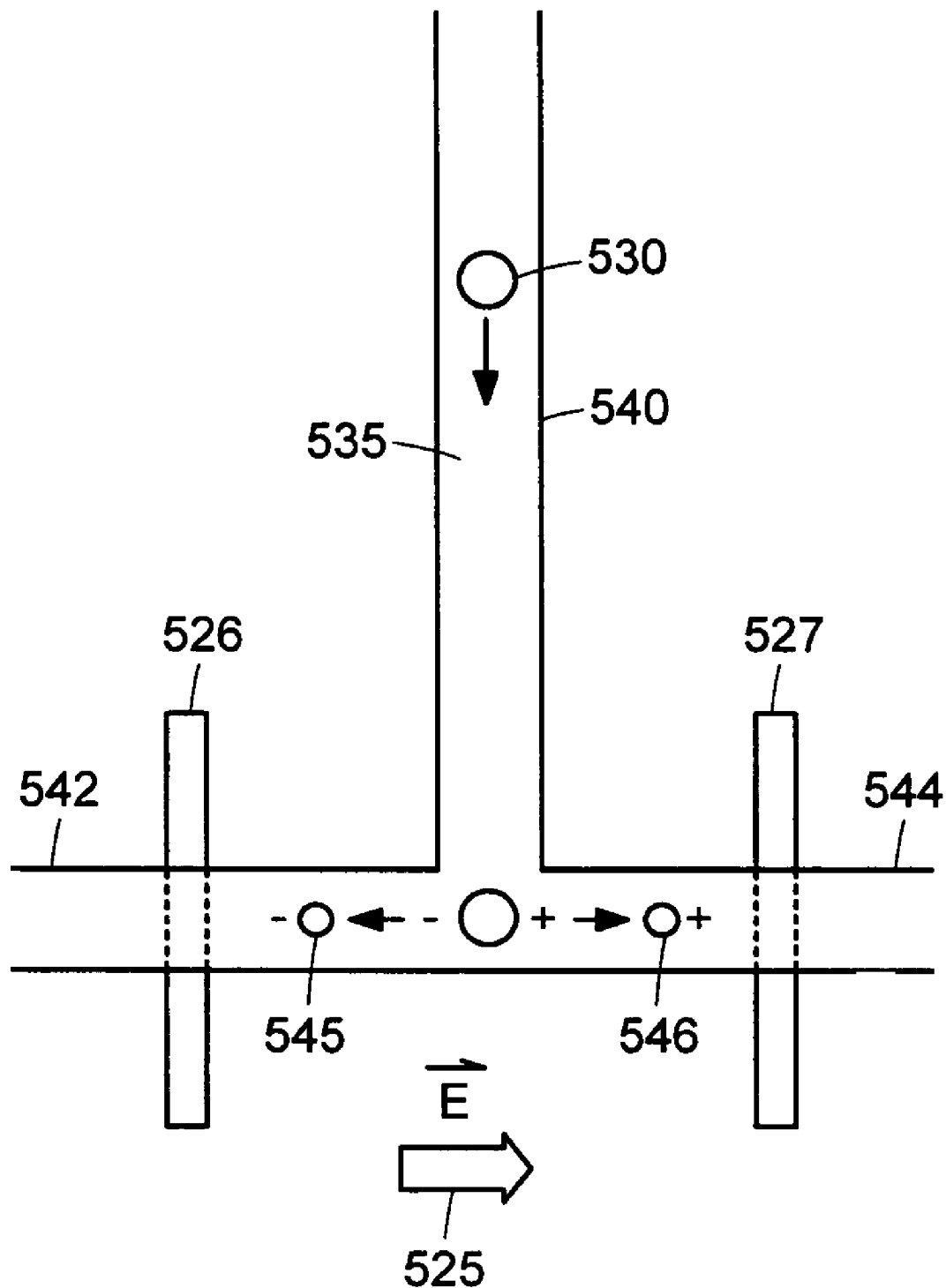
FIG. 5 is a schematic diagram of droplet splitting, in accordance with one embodiment of the invention.

A schematic of this process can be seen in FIG. 5, where a neutral fluidic droplet 530, surrounded by a liquid 535 in channel 540, is subjected to applied electric field 525, created by electrodes 526 and 527. Electrode 526 is positioned near channel 542, while electrode 527 is positioned near channel 544. Under the influence of electric field 525, charge separation is induced within fluidic droplet 530, i.e., such that a positive charge is induced at one end of the droplet, while a negative charge is induced at the other end of the droplet. The droplet may then split into a negatively charged droplet 545 and a positively charged droplet 546, which then may travel in channels 542 and 544, respectively. In some cases, one or both of the electric charges on the resulting charged droplets may also be neutralized, as previously described.

Other examples of splitting a fluidic droplet into two droplets are described in International Patent Application Serial No. PCT/US2004/010903, filed Apr. 9, 2004 by Link, et al.; U.S. Provisional Patent Application Ser. No. 60/498,091, filed Aug. 27, 2003, by Link, et. al.; and International Patent Application Serial No. PCT/US03/20542, filed Jun. 30, 2003 by Stone, et al., published as WO 2004/002627 on Jan. 8, 2004, each incorporated herein by reference.

The invention, in yet another aspect, relates to systems and methods for fusing or coalescing two or more fluidic droplets into one droplet. For example, in one set of embodiments, systems and methods are provided that are able to cause two or more droplets (e.g., arising from discontinuous streams of fluid) to fuse or coalesce into one droplet in cases where the two or more droplets ordinarily are unable to fuse or coalesce, for example, due to composition, surface tension, droplet size, the presence or absence of surfactants, etc. In certain microfluidic systems, the surface tension of the droplets, relative to the size of the droplets, may also prevent fusion or coalescence of the droplets from occurring in some cases.

Figure 13B:
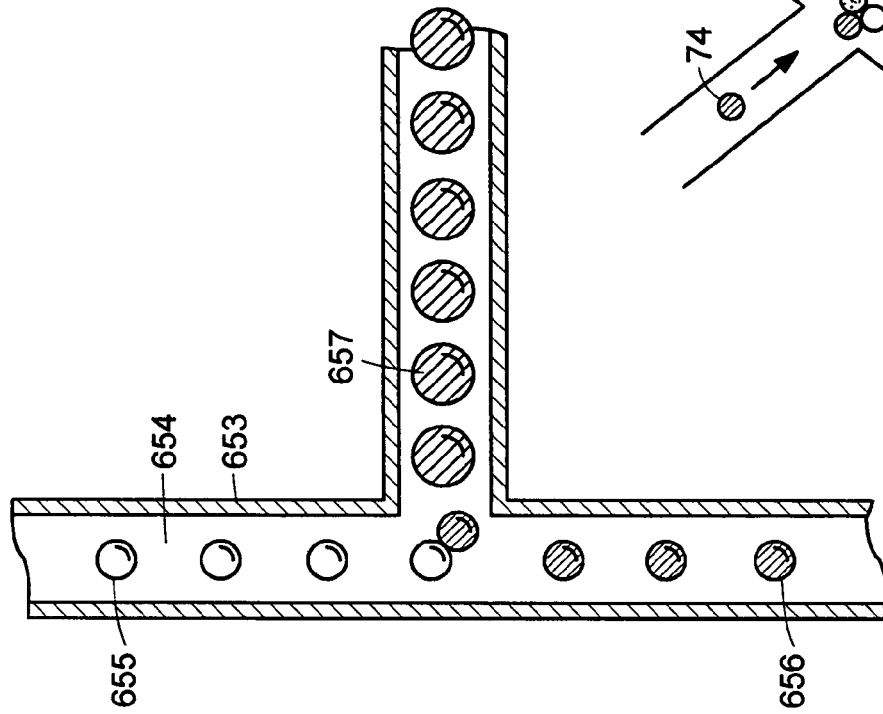
FIGS. 13a-d illustrate the use of oppositely charged droplets in the invention.
Figure 13A:
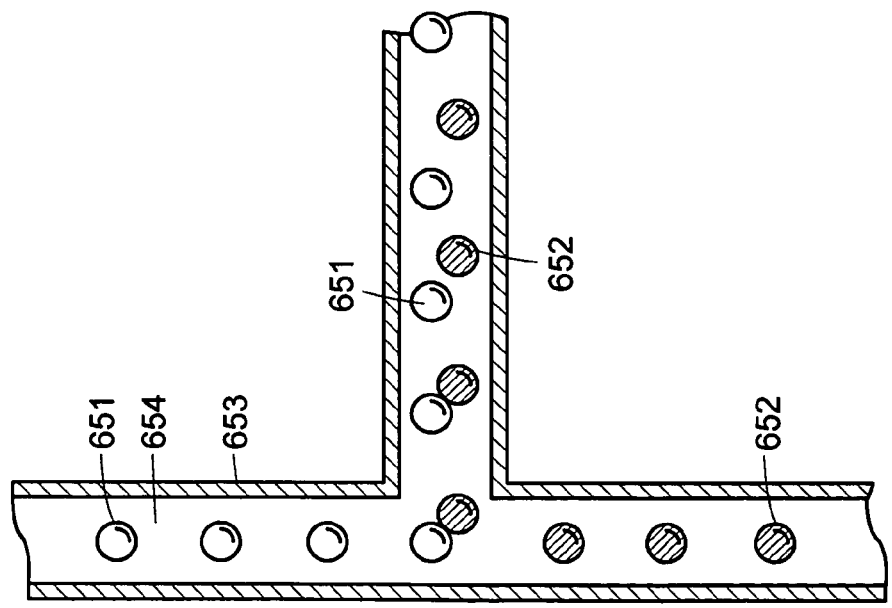

In one embodiment, two fluidic droplets may be given opposite electric charges (i.e., positive and negative charges, not necessarily of the same magnitude), which may increase the electrical interaction of the two droplets such that fusion or coalescence of the droplets can occur due to their opposite electric charges, e.g., using the techniques described herein. For instance, an electric field may be applied to the droplets, the droplets may be passed through a capacitor, a chemical reaction may cause the droplets to become charged, etc. As an example, as is shown schematically in FIG. 13A, uncharged droplets 651 and 652, carried by a liquid 654 contained within a microfluidic channel 653, are brought into contact with each other, but the droplets are not able to fuse or coalesce, for instance, due to their size and/or surface tension. The droplets, in some cases, may not be able to fuse even if a surfactant is applied to lower the surface tension of the droplets. However, if the fluidic droplets are electrically charged with opposite charges (which can be, but are not necessarily of, the same magnitude), the droplets may be able to fuse or coalesce. For instance, in FIG. 13B, positively charged droplets 655 and negatively charged droplets 656 are directed generally towards each other such that the electrical interaction of the oppositely charged droplets causes the droplets to fuse into fused droplets 657.

Figure 13C:
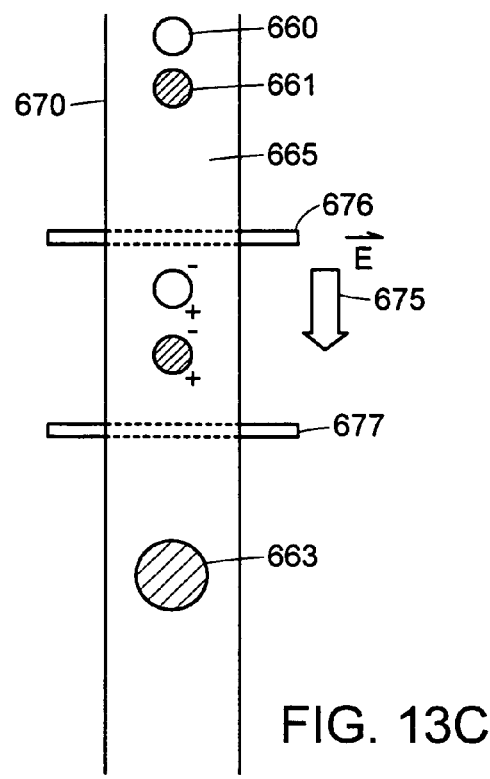
Figure 13D:
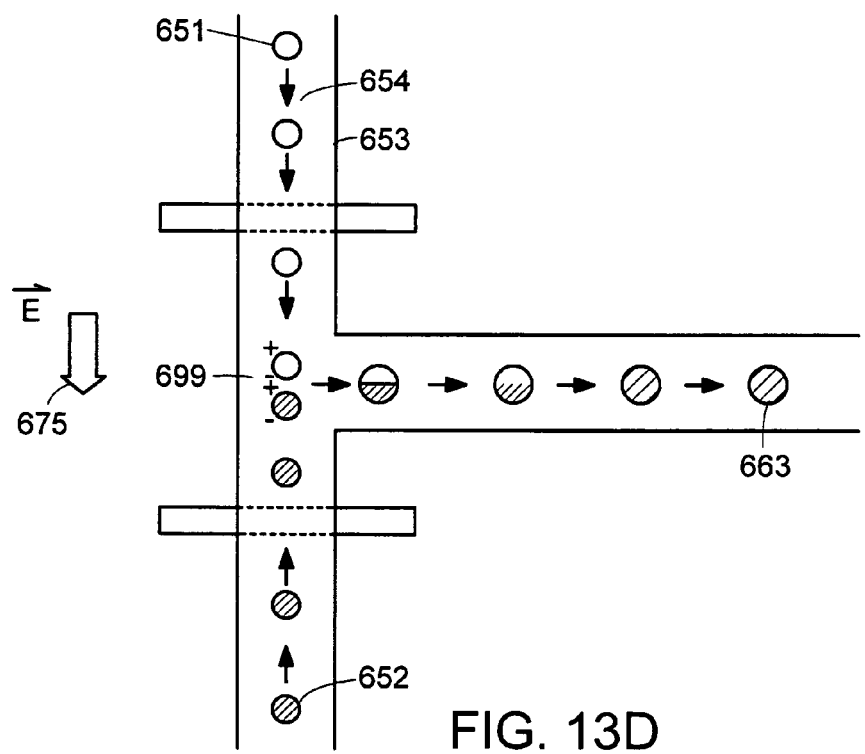

In another embodiment, the fluidic droplets may not necessarily be given opposite electric charges (and, in some cases, may not be given any electric charge), and are fused through the use of dipoles induced in the fluidic droplets that causes the fluidic droplets to coalesce. In the example illustrated in FIG. 13C, droplets 660 and 661 (which may each independently be electrically charged or neutral), surrounded by liquid 665 in channel 670, move through the channel such that they are the affected by an applied electric field 675. Electric field 675 may be an AC field, a DC field, etc., and may be created, for instance, using electrodes 676 and 677, as shown here. The induced dipoles in each of the fluidic droplets, as shown in FIG. 13C, may cause the fluidic droplets to become electrically attracted towards each other due to their local opposite charges, thus causing droplets 660 and 661 to fuse to produce droplet 663. In FIG. 13D, droplets 651 and 652 flow together to fuse to form droplet 653, which flows in a third channel.

Figure 12A:
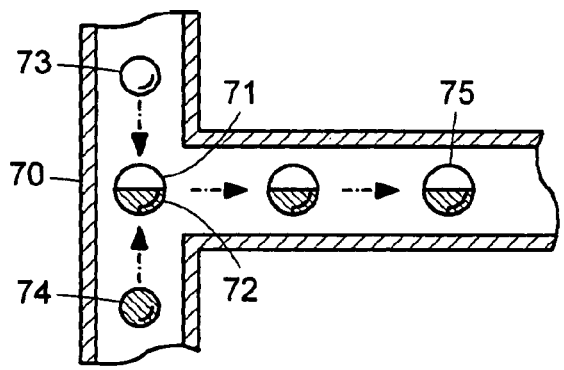
FIGS. 12a-j illustrate flow patterns for droplets in microfluidic systems in accordance with the invention.
Figure 12G:
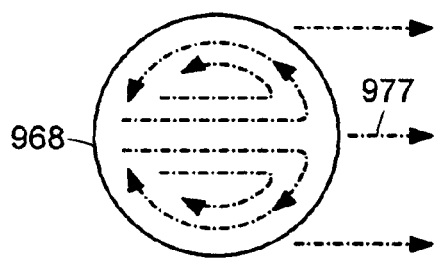
Figure 12B:
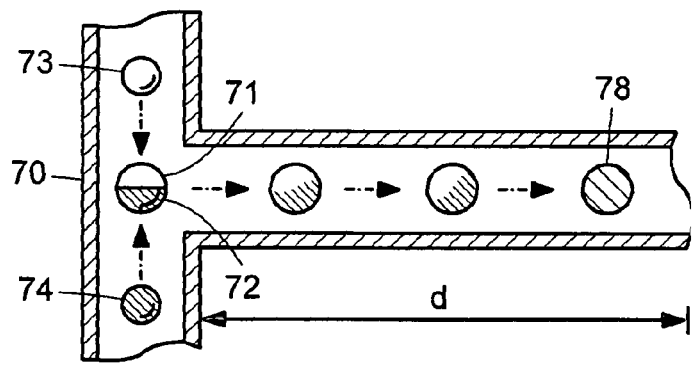
Figure 12C:
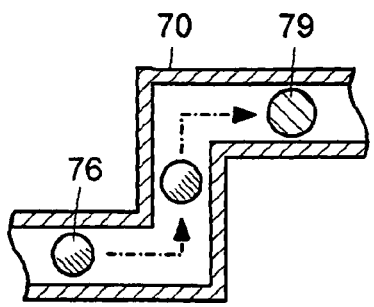
Figure 12D:
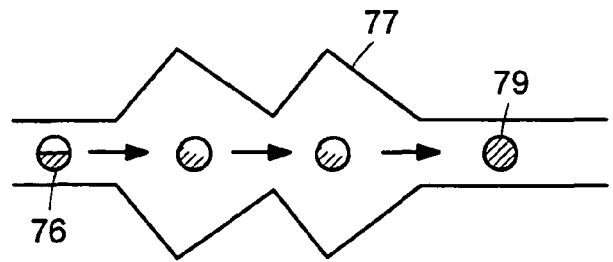
Figure 12E:
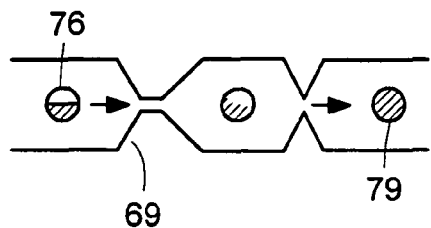
Figure 12F:
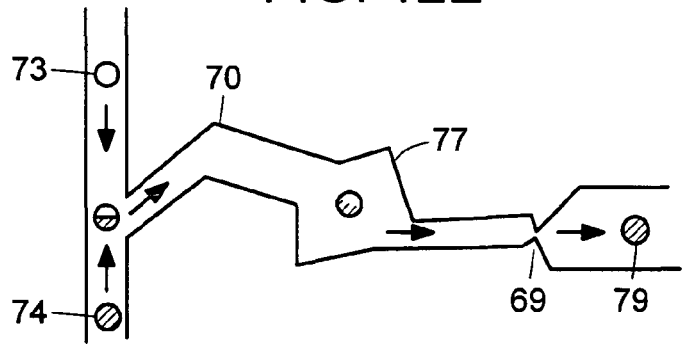
Figure 12H:
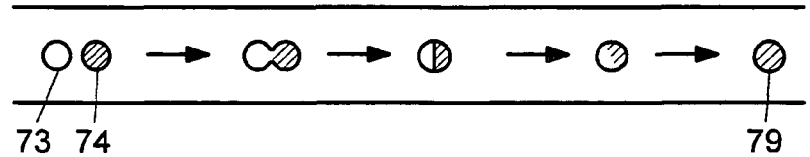
Figure 12I:
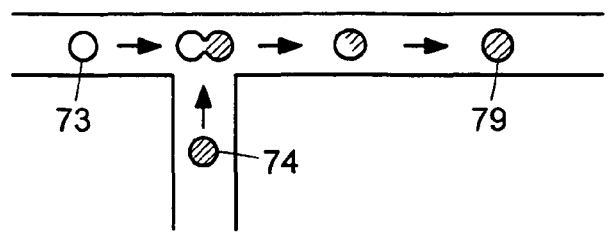
Figure 12J:
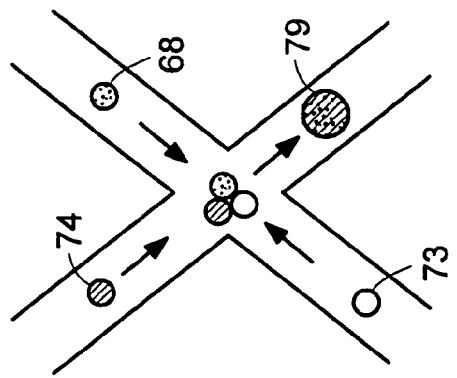

It should be noted that, in various embodiments, the two or more droplets allowed to coalesce are not necessarily required to meet "head-on." Any angle of contact, so long as at least some fusion of the droplets initially occurs, is sufficient. As an example, in FIG. 12H, droplets 73 and 74 each are traveling in substantially the same direction (e.g., at different velocities), and are able to meet and fuse. As another example, in FIG. 12I, droplets 73 and 74 meet at an angle and fuse. In FIG. 12J, three fluidic droplets 73, 74 and 68 meet and fuse to produce droplet 79.

Other examples of fusing or coalescing fluidic droplets are described in International Patent Application Serial No. PCT/US2004/010903, filed Apr. 9, 2004 by Link, et al., incorporated herein by reference.

Fluidic handling of microcapsules therefore results in further advantages:
 (a) Microcapsules can be split into two or more smaller microdroplets allowing the reagents contained therein to be reacted with a series of different molecules in parallel or assayed in multiplicate.
 (b) Microcapsules can be fused. This allows molecules to be: (a) diluted, (b) mixed with other molecules, and (c) reactions initiated, terminated or modulated at precisely defined times.
 (c) Reagents can be mixed very rapidly (in <2 ms) in microcapsules using chaotic advection, allowing fast kinetic measurements and very high throughput.
 (d) Reagents can be mixed in a combinatorial manner. For example, allowing the effect of all possible pairwise combinations of compounds in a library to be tested.

Creating and manipulating microcapsules in microfluidic systems means that:
 (a) Stable streams of microcapsules can be formed in microchannels and identified by their relative positions.
 (b) If the reactions are accompanied by an optical signal (e.g. a change in fluorescence) a spatially-resolved optical image of the microfluidic network allows time resolved measurements of the reactions in each microcapsules.
 (c) Microcapsules can be separated using a microfluidic flow sorter to allow recovery and further analysis or manipulation of the molecules they contain.

Screening/Sorting of Microcapsules

In still another aspect, the invention provides systems and methods for screening or sorting fluidic droplets in a liquid, and in some cases, at relatively high rates. For example, a characteristic of a droplet may be sensed and/or determined in some fashion (e.g., as further described below), then the droplet may be directed towards a particular region of the device, for example, for sorting or screening purposes.

In some embodiments, a characteristic of a fluidic droplet may be sensed and/or determined in some fashion, for example, as described herein (e.g., fluorescence of the fluidic droplet may be determined), and, in response, an electric field may be applied or removed from the fluidic droplet to direct the fluidic droplet to a particular region (e.g. a channel). In some cases, high sorting speeds may be achievable using certain systems and methods of the invention. For instance, at least about 10 droplets per second may be determined and/or sorted in some cases, and in other cases, at least about 20 droplets per second, at least about 30 droplets per second, at least about 100 droplets per second, at least about 200 droplets per second, at least about 300 droplets per second, at least about 500 droplets per second, at least about 750 droplets per second, at least about 1000 droplets per second, at least about 1500 droplets per second, at least about 2000 droplets per second, at least about 3000 droplets per second, at least about 5000 droplets per second, at least about 7500 droplets per second, at least about 10,000 droplets per second, at least about 15,000 droplets per second, at least about 20,000 droplets per second, at least about 30,000 droplets per second, at least about 50,000 droplets per second, at least about 75,000 droplets per second, at least about 100,000 droplets per second, at least about 150,000 droplets per second, at least about 200,000 droplets per second, at least about 300,000 droplets per second, at least about 500,000 droplets per second, at least about 750,000 droplets per second, at least about 1,000,000 droplets per second, at least about 1,500,000 droplets per second, at least about 2,000,000 or more droplets per second, or at least about 3,000,000 or more droplets per second may be determined and/or sorted in such a fashion.

Figure 2A:
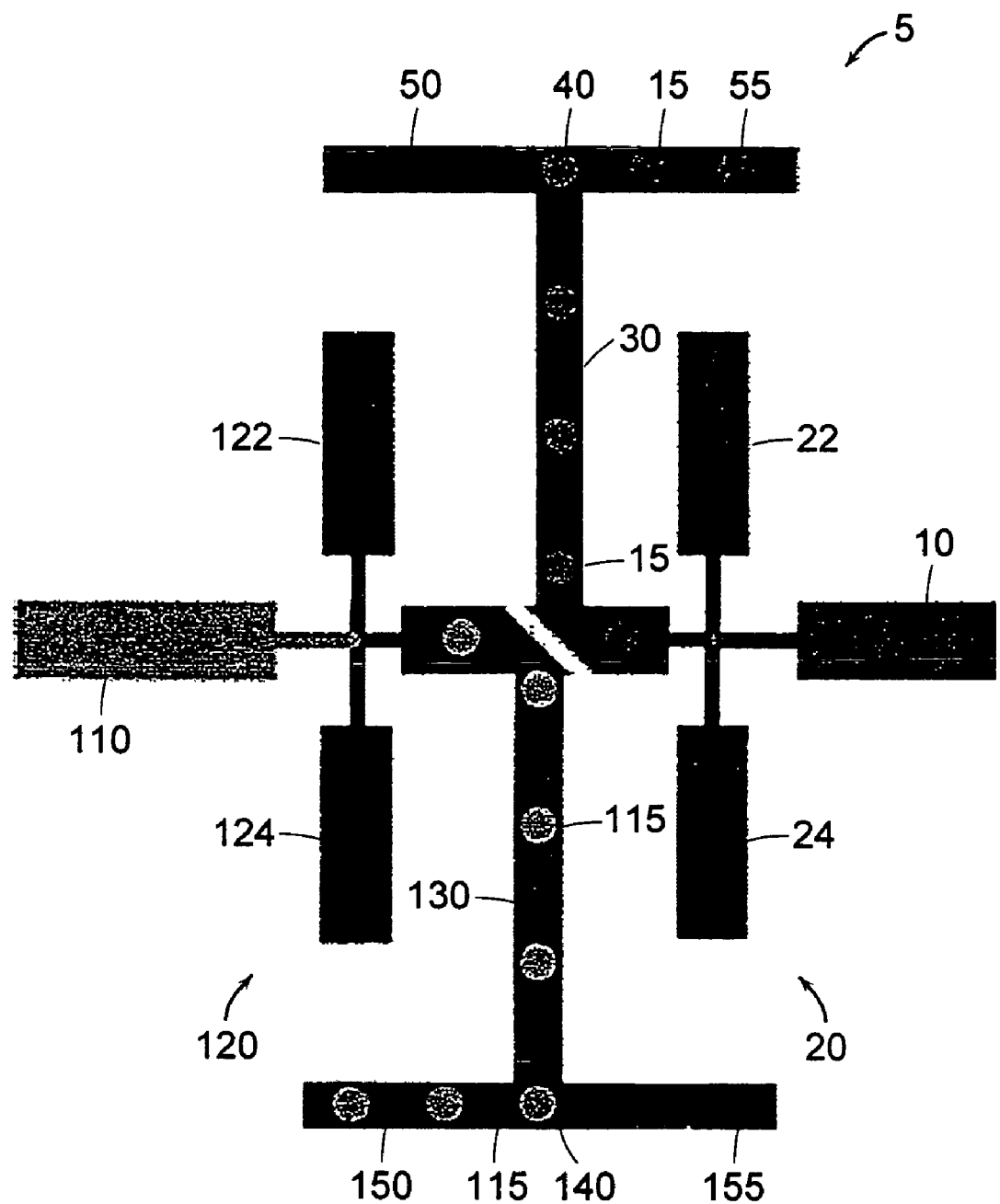
FIGS. 2A and 2B illustrate an apparatus in accordance with an embodiment of the invention, before the application of an electric field thereto.

In one set of embodiments, a fluidic droplet may be directed by creating an electric charge (e.g., as previously described) on the droplet, and steering the droplet using an applied electric field, which may be an AC field, a DC field, etc. As an example, in reference to FIGS. 2-4, an electric field may be selectively applied and removed (or a different electric field may be applied, e.g., a reversed electric field as shown in FIG. 4A) as needed to direct the fluidic droplet to a particular region. The electric field may be selectively applied and removed as needed, in some embodiments, without substantially altering the flow of the liquid containing the fluidic droplet. For example, a liquid may flow on a substantially steady-state basis (i.e., the average flowrate of the liquid containing the fluidic droplet deviates by less than 20% or less than 15% of the steady-state flow or the expected value of the flow of liquid with respect to time, and in some cases, the average flowrate may deviate less than 10% or less than 5%) or other predetermined basis through a fluidic system of the invention (e.g., through a channel or a microchannel), and fluidic droplets contained within the liquid may be directed to various regions, e.g., using an electric field, without substantially altering the flow of the liquid through the fluidic system. As a particular example, in FIGS. 2A, 3A and 4A, a liquid containing fluidic droplets 15 flows from fluid source 10, through channel 30 to intersection 40, and exits through channels 50 and 55. In FIG. 2A, fluidic droplets 15 are directed through both channels 50 and 55, while in FIG. 3A, fluidic droplets 15 are directed to only channel 55 and, in FIG. 4A, fluidic droplets 15 are directed to only channel 50.

Figure 9B:
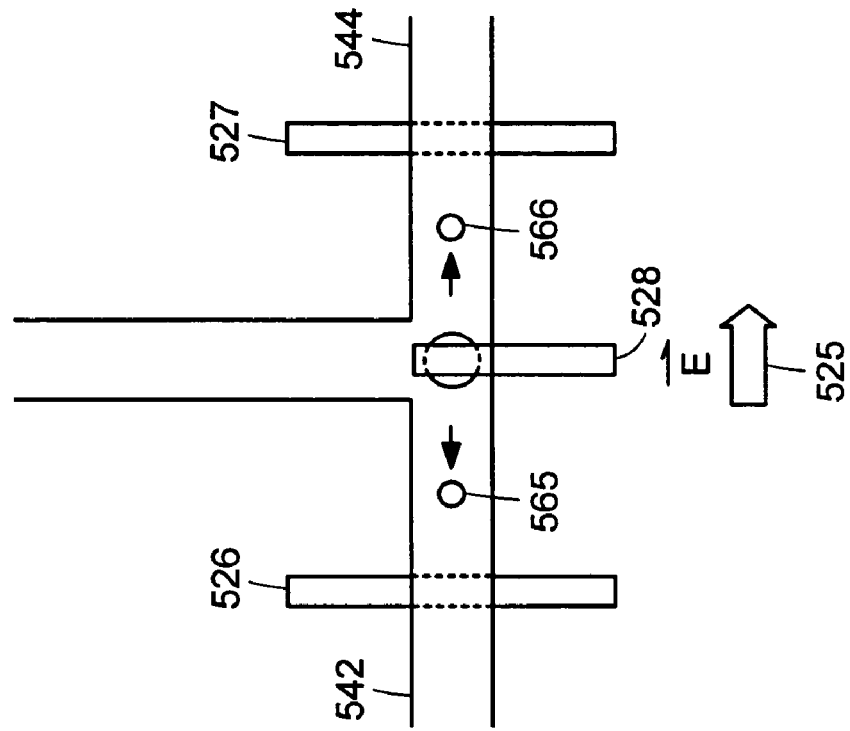
FIGS. 9a-d illustrate the induction of dipoles in droplets in accordance with the invention.

In another set of embodiments, a fluidic droplet may be sorted or steered by inducing a dipole in the fluidic droplet (which may be initially charged or uncharged), and sorting or steering the droplet using an applied electric field. The electric field may be an AC field, a DC field, etc. For example, with reference to FIG. 9A, a channel 540, containing fluidic droplet 530 and liquid 535, divides into channel 542 and 544. Fluidic droplet 530 may have an electric charge, or it may be uncharged. Electrode 526 is positioned near channel 542, while electrode 527 is positioned near channel 544. Electrode 528 is positioned near the junction of channels 540, 542, and 544. In FIGS. 9C and 9D, a dipole is induced in the fluidic droplet using electrodes 526, 527, and/or 528. In FIG. 9C, a dipole is induced in droplet 530 by applying an electric field 525 to the droplet using electrodes 527 and 528. Due to the strength of the electric field, the droplet is strongly attracted to the right, into channel 544. Similarly, in FIG. 9D, a dipole is induced in droplet 530 by applying an electric field 525 to the droplet using electrodes 526 and 528, causing the droplet to be attracted into channel 542. Thus, by applying the proper electric field, droplet 530 can be directed to either channel 542 or 544 as desired.

Figures 10A, 10B:
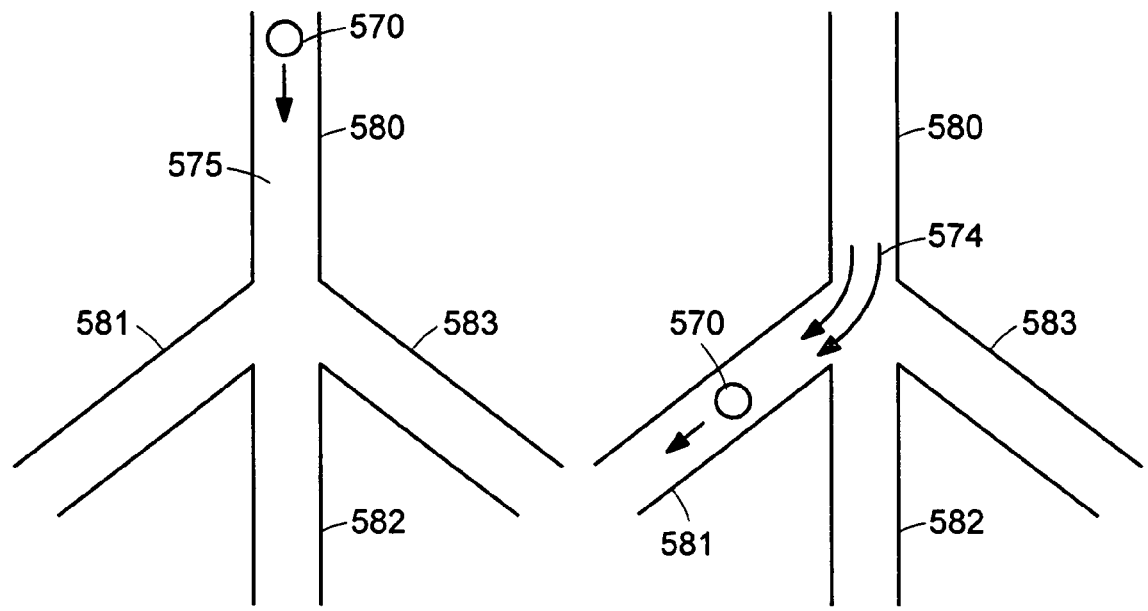
FIGS. 10a-d illustrate the sorting of microcapsules by altering the flow of carrier fluid in a microfluidic system.
Figures 10C, 10D:
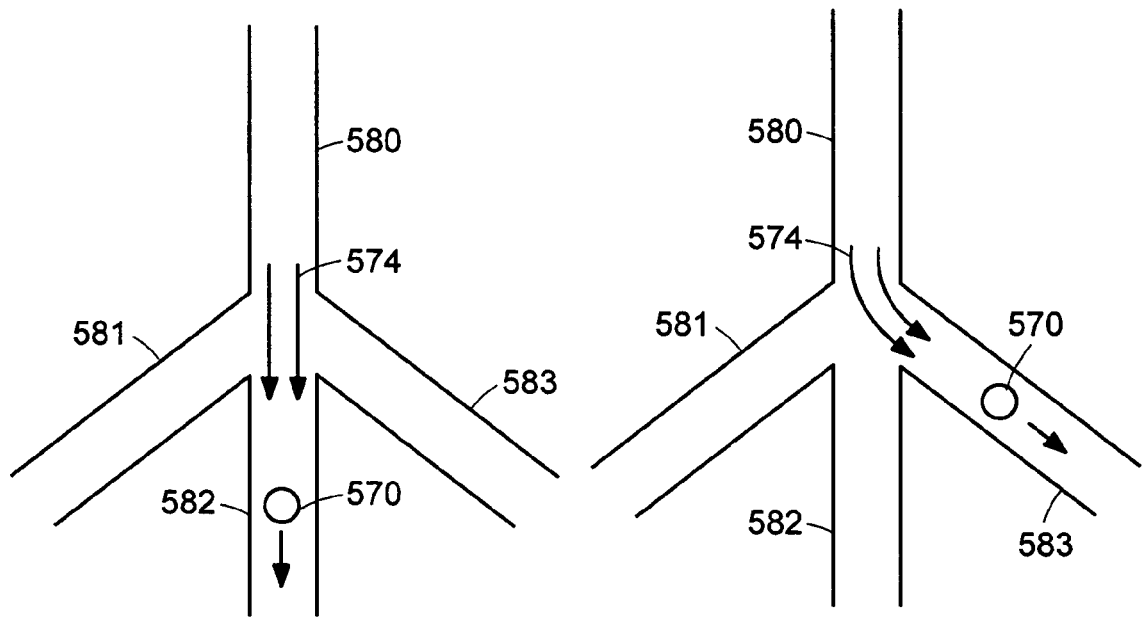

In other embodiments, however, the fluidic droplets may be screened or sorted within a fluidic system of the invention by altering the flow of the liquid containing the droplets. For instance, in one set of embodiments, a fluidic droplet may be steered or sorted by directing the liquid surrounding the fluidic droplet into a first channel, a second channel, etc. As a non-limiting example, with reference to FIG. 10A, fluidic droplet 570 is surrounded by a liquid 575 in channel 580. Channel 580 divides into three channels 581, 582, and 583. The flow of liquid 575 can be directed into any of channels 581, 582, and 583 as desired, for example, using flow-controlling devices known to those of ordinary skill in the art, for example, valves, pumps, pistons, etc. Thus, in FIG. 10B, fluidic droplet 570 is directed into channel 581 by directing liquid 575 to flow into channel 581 (indicated by arrows 574); in FIG. 10C, fluidic droplet 570 is directed into channel 582 by directing liquid 575 to flow into channel 582 (indicated by arrows 574); and in FIG. 10D, fluidic droplet 570 is directed into channel 583 by directing liquid 575 to flow into channel 583 (indicated by arrows 574).

However, it is preferred that control of the flow of liquids in microfluidic systems is not used to direct the flow of fluidic droplets therein, but that an alternative method is used. Advantageously, therefore, the microcapsules are not sorted by altering the direction of the flow of a carrier fluid in a microfluidic system.

In another set of embodiments, pressure within a fluidic system, for example, within different channels or within different portions of a channel, can be controlled to direct the flow of fluidic droplets. For example, a droplet can be directed toward a channel junction including multiple options for further direction of flow (e.g., directed toward a branch, or fork, in a channel defining optional downstream flow channels). Pressure within one or more of the optional downstream flow channels can be controlled to direct the droplet selectively into one of the channels, and changes in pressure can be effected on the order of the time required for successive droplets to reach the junction, such that the downstream flow path of each successive droplet can be independently controlled. In one arrangement, the expansion and/or contraction of liquid reservoirs may be used to steer or sort a fluidic droplet into a channel, e.g., by causing directed movement of the liquid containing the fluidic droplet. The liquid reservoirs may be positioned such that, when activated, the movement of liquid caused by the activated reservoirs causes the liquid to flow in a preferred direction, carrying the fluidic droplet in that preferred direction. For instance, the expansion of a liquid reservoir may cause a flow of liquid towards the reservoir, while the contraction of a liquid reservoir may cause a flow of liquid away from the reservoir. In some cases, the expansion and/or contraction of the liquid reservoir may be combined with other flow-controlling devices and methods, e.g., as described herein. Non-limiting examples of devices able to cause the expansion and/or contraction of a liquid reservoir include pistons and piezoelectric components. In some cases, piezoelectric components may be particularly useful due to their relatively rapid response times, e.g., in response to an electrical signal.

As a non-limiting example, in FIG. 11A, fluidic droplet 600 is surrounded by a liquid 605 in channel 610. Channel 610 divides into channels 611, 612. Positioned in fluidic communication with channels 611 and 612 are liquid reservoirs 617 and 618, which may be expanded and/or contracted, for instance, by piezoelectric components 615 and 616, by a piston (not shown), etc. In FIG. 11B, liquid reservoir 617 has been expanded, while liquid reservoir 618 has been contracted. The effect of the expansion/contractions of the reservoirs is to cause a net flow of liquid towards channel 611, as indicated by arrows 603. Thus, fluidic droplet 600, upon reaching the junction between the channels, is directed to channel 611 by the movement of liquid 605. The reverse situation is shown in FIG. 11C, where liquid reservoir 617 has contracted while liquid reservoir 618 has been expanded. A net flow of liquid occurs towards channel 612 (indicated by arrows 603), causing fluidic droplet 600 to move into channel 612. It should be noted, however, that reservoirs 617 and 618 do not both need to be activated to direct fluidic droplet 600 into channels 611 or 612. For example, in one embodiment, fluidic droplet 600 may be directed to channel 611 by the expansion of liquid reservoir 617 (without any alteration of reservoir 618), while in another embodiment, fluidic droplet 600 may be directed to channel 611 by the contraction of liquid reservoir 618 (without any alteration of reservoir 617). In some cases, more than two liquid reservoirs may be used.

Figure 6A:
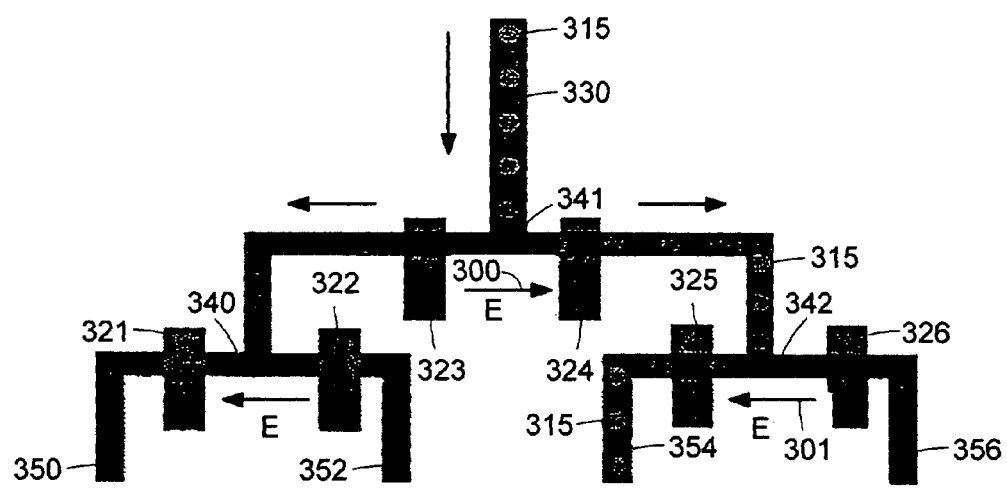
FIGS. 6A and 6B are schematic diagrams of additional embodiments of the invention.
Figure 6B:
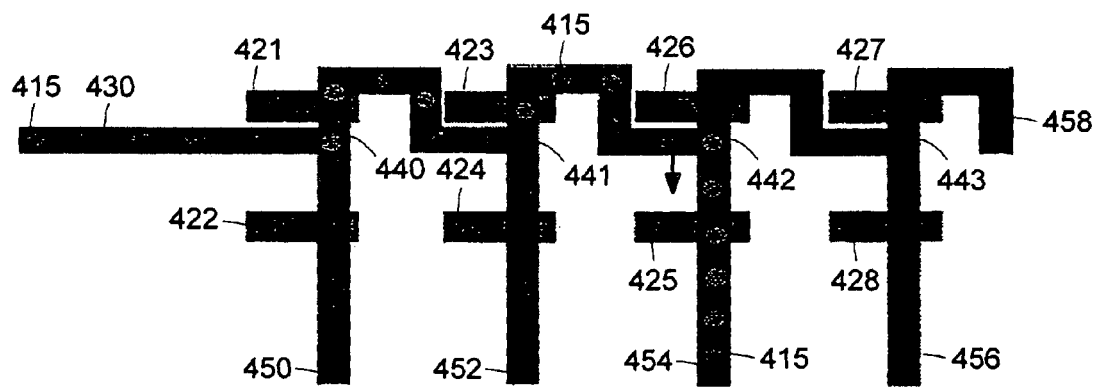

In some embodiments, the fluidic droplets may be sorted into more than two channels. Non-limiting examples of embodiments of the invention having multiple regions within a fluidic system for the delivery of droplets are shown in FIGS. 6A and 6B. Other arrangements are shown in FIGS. 10A-10D. In FIG. 6A, charged droplets 315 in channel 330 may be directed as desired to any one of exit channels 350, 352, 354, or 356, by applying electric fields to control the movement of the droplets at intersections 340, 341, and 342, using electrodes 321/322, 323/324, and 325/326, respectively. In FIG. 6A, droplets 315 are directed to channel 354 using applied electric fields 300 and 301, using principles similar to those discussed above. Similarly, in FIG. 6B, charged droplets 415 in channel 430 can be directed to any one of exit channels 450, 452, 454, 456, or 458, by applying electric fields to control the movement of the droplets at intersections 440, 441, 442, and 443, using electrodes 421/422, 423/424, 425/426, and 427/428, respectively. In this figure, droplets 415 are directed to channel 454; of course, the charged droplets may be directed to any other exit channel as desired.

Figure 2B:
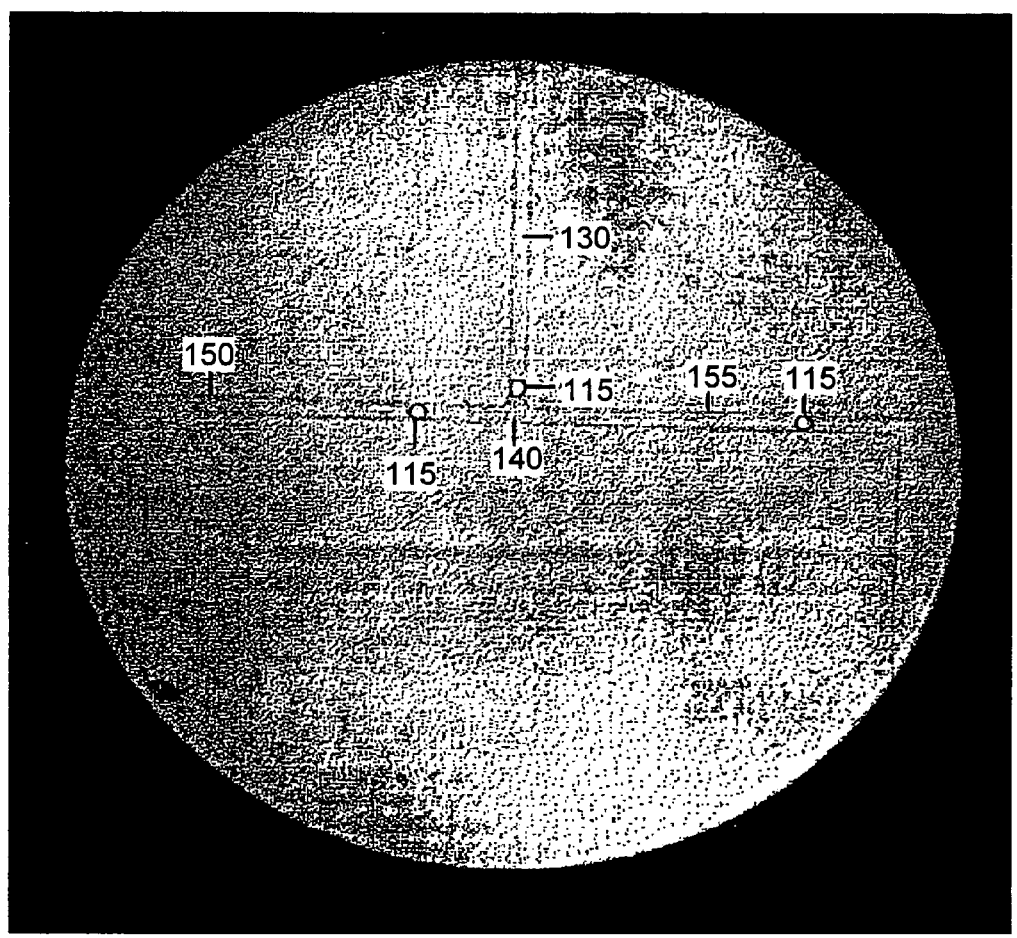

In another example, in apparatus 5, as schematically illustrated in FIG. 2A, fluidic droplets 15 created by fluid source 10 are positively charged due to an applied electric field created using electric field generator 20, which comprises two electrodes 22, 24. Fluidic droplets 15 are directed through channel 30 by a liquid containing the droplets, and are directed towards intersection 40. At intersection 40, the fluidic droplets do not have a preferred orientation or direction, and move into exit channels 50 and 55 with equal probability (in this embodiment, liquid drains through both exit channels 50 and 55 at substantially equal rates). Similarly, fluidic droplets 115 created by fluid source 110 are negatively charged due to an applied electric field created using electric field generator 120, which comprises electrodes 122 and 124. After traveling through channel 130 towards intersection 140, the fluidic droplets do not have a preferred orientation or direction, and move into exit channels 150 and 155 with equal probability, as the liquid exits through exit channels 150 and 155 at substantially equal rates. A representative photomicrograph of intersection 140 is shown in FIG. 2B.

Figure 3A:
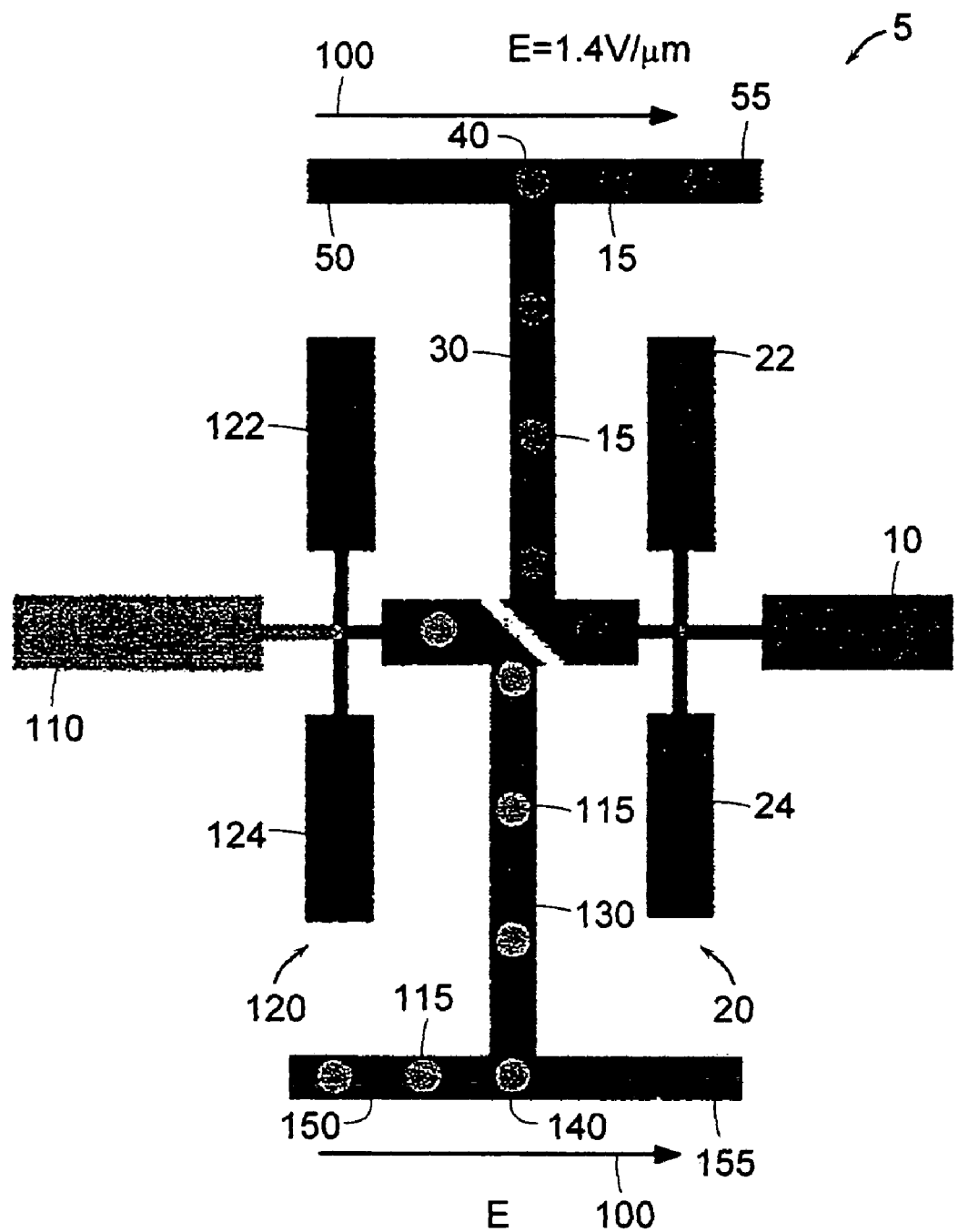
FIGS. 3A and 3B illustrate the apparatus of FIGS. 2A and 2B after the application of an electric field thereto.
Figure 3B:
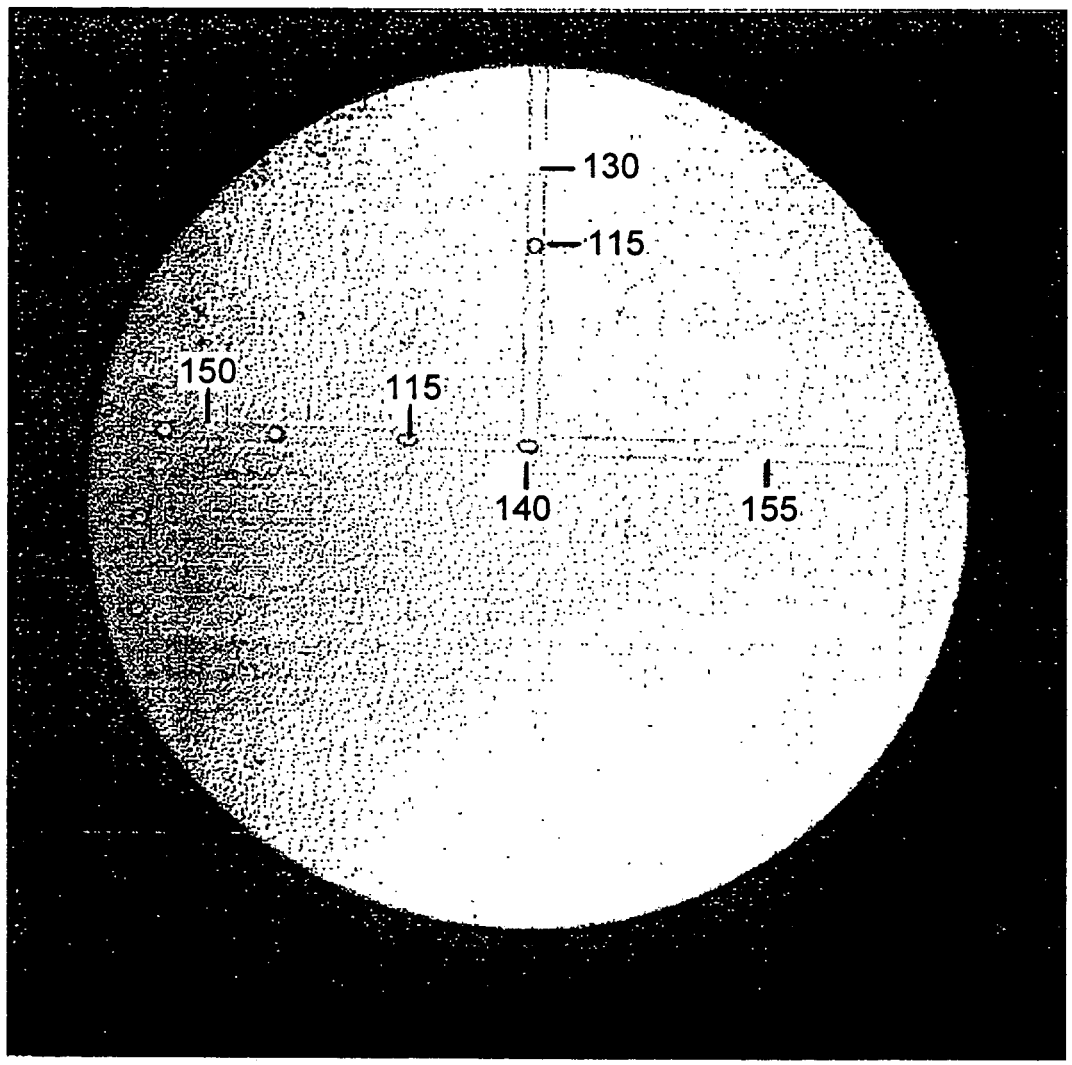
Figure 4A:
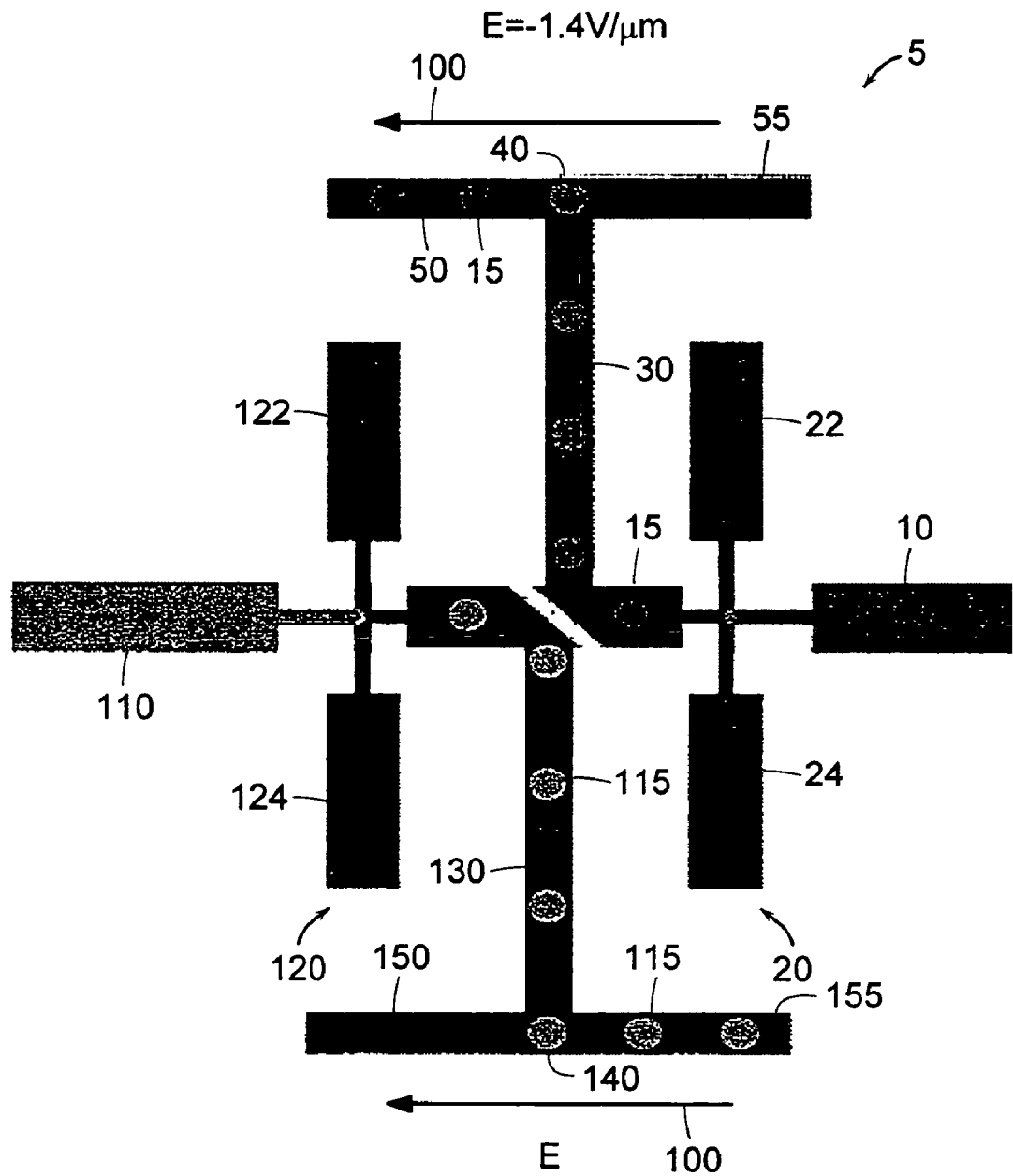
FIGS. 4A and 4B illustrate the apparatus of FIGS. 2A and 2B after the application of a reversed electric field thereto.

In the schematic diagram of FIG. 3A, an electric field 100 of 1.4 V/micrometer has been applied to apparatus 5 of FIG. 2A, in a direction towards the right of apparatus 5. Positively-charged fluidic droplets 15 in channel 30, upon reaching intersection 40, are directed to the right in channel 55 due to the applied electric field 100, while the liquid containing the droplets continues to exit through exit channels 50 and 55 at substantially equal rates. Similarly, negatively-charged fluidic droplets 115 in channel 130, upon reaching intersection 140, are directed to the left in channel 150 due to the applied electric field 100, while the liquid fluid continues to exit the device through exit channels 150 and 155 at substantially equal rates. Thus, electric field 100 can be used to direct fluidic droplets into particular channels as desired. A representative photomicrograph of intersection 140 is shown in FIG. 3B.

Figure 4B:
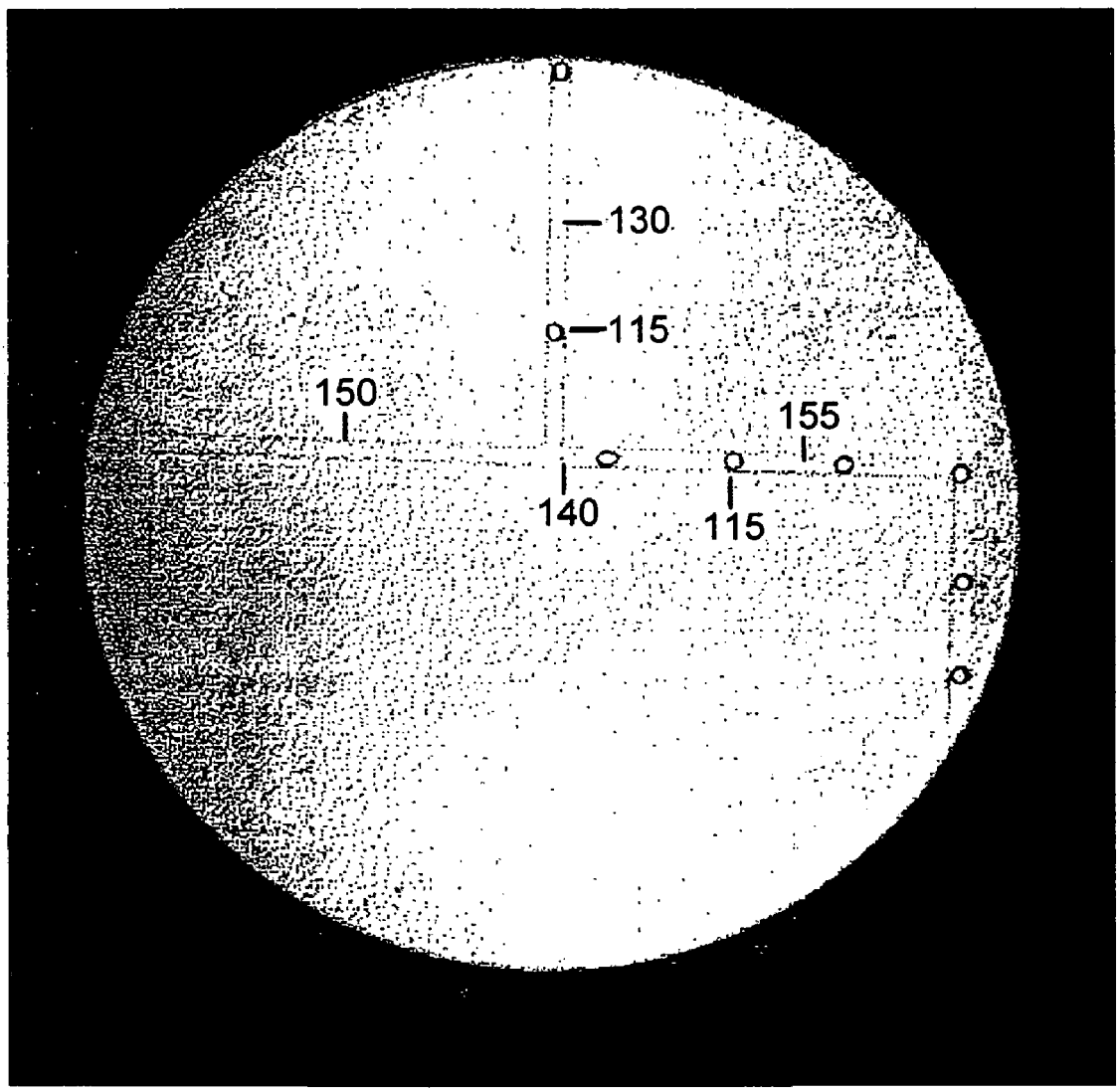

FIG. 4A is a schematic diagram of apparatus 5 of FIG. 2A, also with an applied electric field 100 of 1.4 V/micrometer, but in the opposite direction (i.e., −1.4 V/micrometer). In this figure, positively-charged fluidic droplets 15 in channel 30, upon reaching intersection 40, are directed to the left into channel 50 due to the applied electric field 100, while negatively-charged fluidic droplets 115 in channel 130, upon reaching intersection 140, are directed to the right into channel 155 due to applied electric field 100. The liquid containing the droplets exits through exit channels 50 and 55, and 150 and 155, at substantially equal rates. A representative photomicrograph of intersection 140 is shown in FIG. 4B.

In some embodiments of the invention, a fluidic droplet may be sorted and/or split into two or more separate droplets, for example, depending on the particular application. Any of the above-described techniques may be used to spilt and/or sort droplets. As a non-limiting example, by applying (or removing) a first electric field to a device (or a portion thereof), a fluidic droplet may be directed to a first region or channel; by applying (or removing) a second electric field to the device (or a portion thereof), the droplet may be directed to a second region or channel; by applying a third electric field to the device (or a portion thereof), the droplet may be directed to a third region or channel; etc., where the electric fields may differ in some way, for example, in intensity, direction, frequency, duration, etc. In a series of droplets, each droplet may be independently sorted and/or split; for example, some droplets may be directed to one location or another, while other droplets may be split into multiple droplets directed to two or more locations.

Figure 8C:
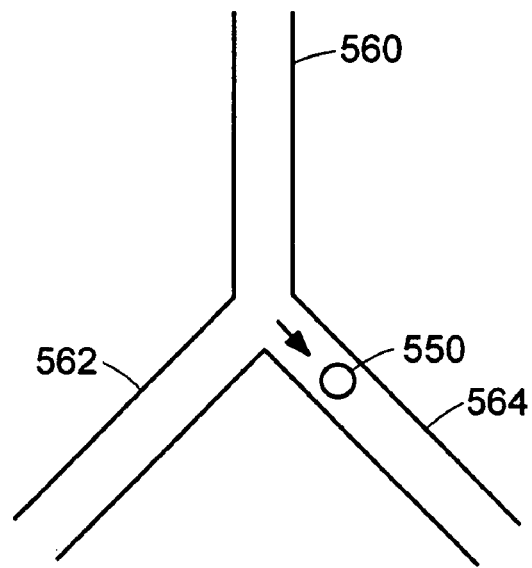
Figure 8D:
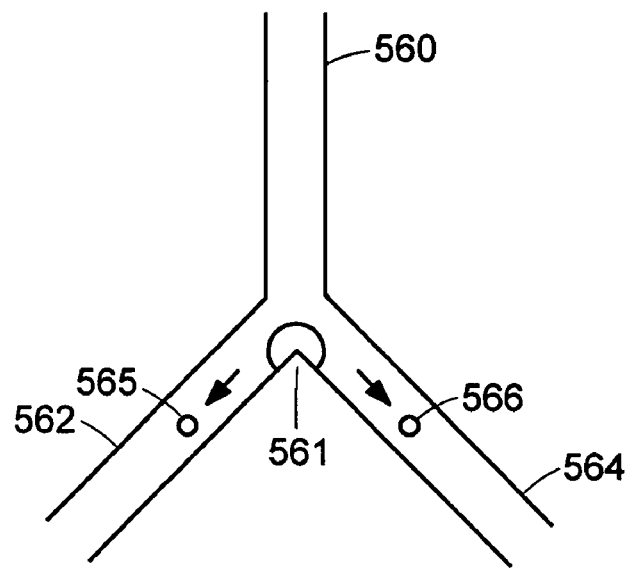
Figure 8E:
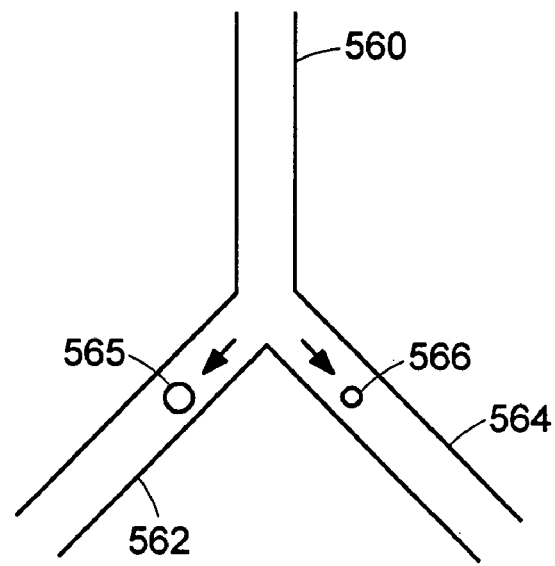
Figure 8F:
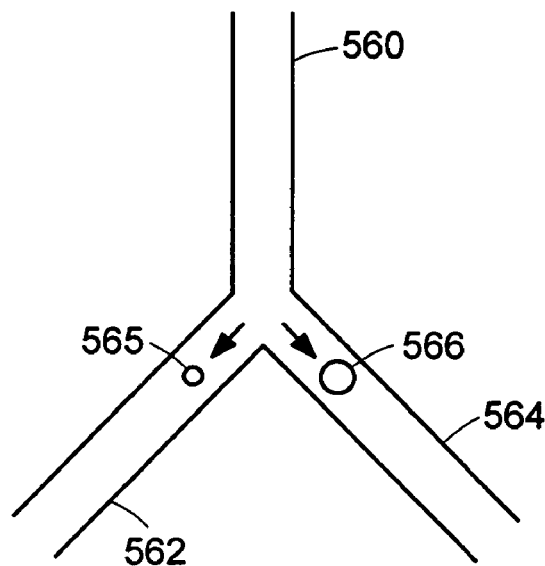

As one particular example, in FIG. 8A, fluidic droplet 550, surrounding liquid 555 in channel 560 may be directed to channel 556, channel 557, or be split in some fashion between channels 562 and 564. In FIG. 8B, by directing surrounding liquid 555 towards channel 562, fluidic droplet 550 may be directed towards the left into channel 562; in FIG. 8C, by directing surrounding liquid 555 towards channel 564, fluidic droplet 550 may be directed towards the right into channel 564, In FIG. 8D, an electric field may be applied, in combination with control of the flow of liquid 555 surrounding fluidic droplet 550, that causes the droplet to impact junction 561, which may cause the droplet to split into two separate fluidic droplets 565, 566. Fluidic droplet 565 is directed to channel 562, while fluidic droplet 566 is directed to channel 566. A high degree of control of the applied electric field may be achieved to control droplet formation; thus, for example, after fluidic droplet 565 has been split into droplets 565 and 566, droplets 565 and 566 may be of substantially equal size, or either of droplets 565 and 566 may be larger, e.g., as is shown in FIGS. 8E and 8F, respectively.

Figure 9A:
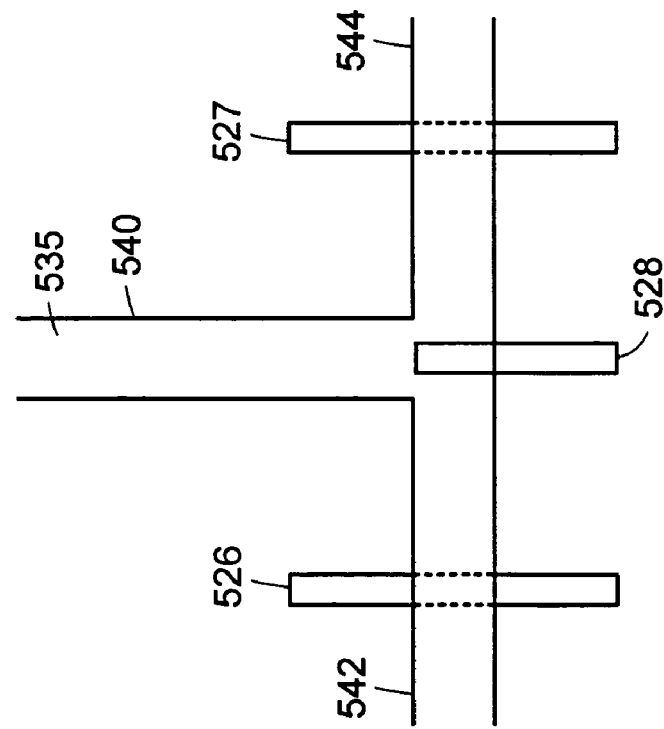
Figure 9D:
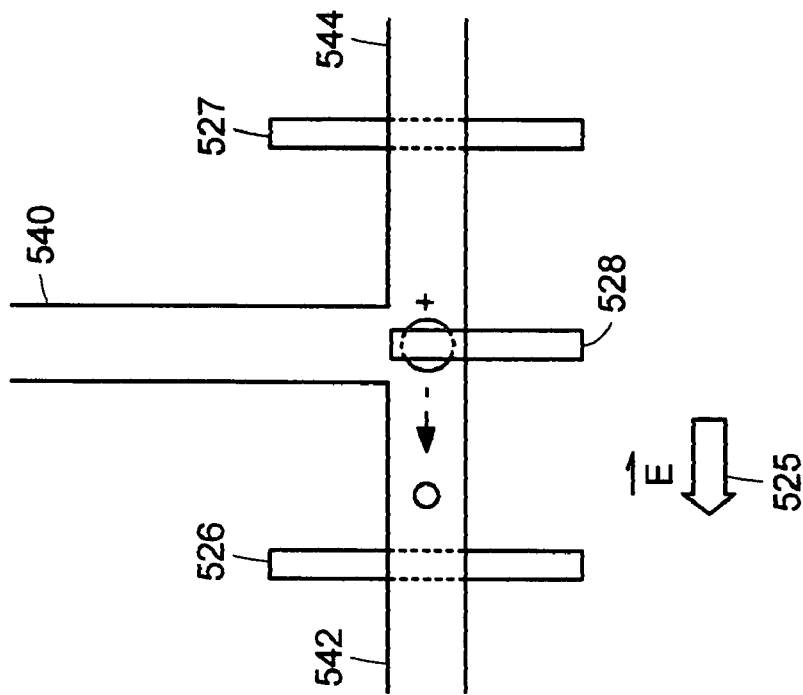
Figure 9C:
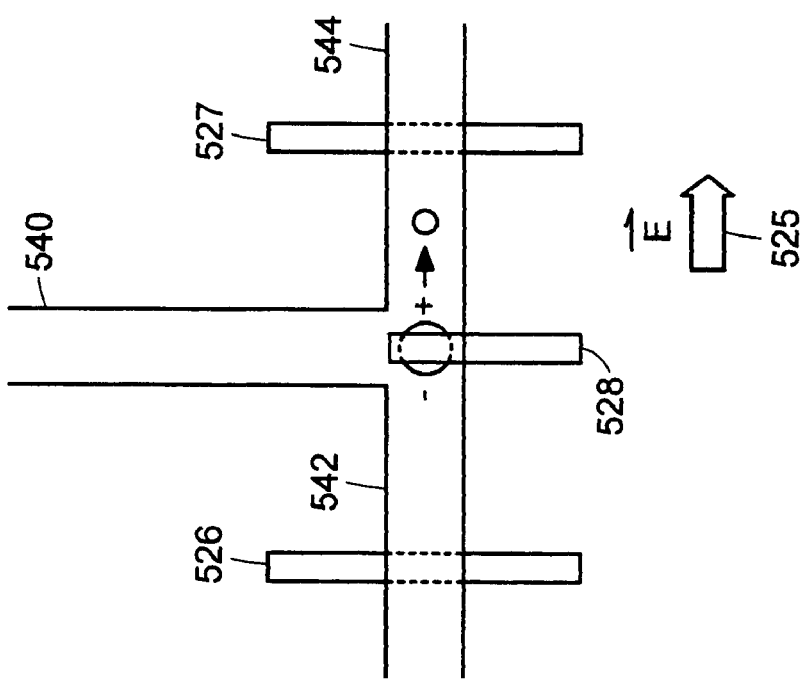

As another example, in FIG. 9A, channel 540, carrying fluidic droplet 530 and liquid 535, divides into channel 542 and 544. Fluidic droplet 530 may be electrically charged, or it may uncharged. Electrode 526 is positioned near channel 542, while electrode 527 is positioned near channel 544. Electrode 528 is positioned near the junction of channels 540, 542, and 544. When fluidic droplet 530 reaches the junction, it may be subjected to an electric field, and/or directed to a channel or other region, for example, by directing the surrounding liquid into the channel. As shown in FIG. 9B, fluidic droplet 530 may be split into two separate droplets 565 and 566 by applying an electric field 525 to the droplet using electrodes 526 and 527. In FIG. 9C, a dipole can be induced in droplet 530 by applying an electric field 525 to the droplet using electrodes 527 and 528. Due to the strength of the applied electric field, the droplet may be strongly attracted to the right, into channel 544. Similarly, in FIG. 9D, a dipole may be induced in droplet 530 by applying an electric field 525 to the droplet using electrodes 526 and 528, causing the droplet to be attracted into channel 542. By controlling which electrodes are used to induce an electric field across droplet 530, and/or the strength of the applied electric field, one or more fluidic droplets within channel 540 may be sorted and/or split into two droplets, and each droplet may independently be sorted and/or split.

Microcapsules can be optically tagged by, for example, incorporating fluorochromes. In a preferred configuration, the microcapsules are optically tagged by incorporating quantum dots: quantum dots of 6 colours at 10 concentrations would allow the encoding of $10^6$ microcapsules (Han et al., 2001). Microcapsules flowing in an ordered sequence in a microfluidic channel can be encoded (wholly or partially) by their sequence in the stream of microcapsules (positional encoding).

By means of the invention, enzymes involved in the preparation of a compound may be optimised by selection for optimal activity. The procedure involves the preparation of variants of the polypeptide to be screened, which equate to a library of polypeptides as refereed to herein. The variants may be prepared in the same manner as the libraries discussed elsewhere herein.

(B) Selection Procedures

The system can be configured to select for RNA, DNA or protein gene product molecules with catalytic, regulatory or binding activity.

(i) Selection for Binding

In the case of selection for a gene product with affinity for a specific ligand the genetic element may be linked to the gene product in the microcapsule via the ligand. Only gene products with affinity for the ligand will therefore bind to the genetic element and only those genetic elements with gene product bound via the ligand will acquire the changed optical properties which enable them to be retained in the selection step. In this embodiment, the genetic element will thus comprise a nucleic acid encoding the gene product linked to a ligand for the gene product.

The change in optical properties of the genetic element after binding of the gene product to the ligand may be induced in a variety of ways, including:

(1) the gene product itself may have distinctive optical properties, for example, it is fluorescent (e.g. green fluorescent protein, (Lorenz et al., 1991)).
(2) the optical properties of the gene product may be modified on binding to the ligand, for example, the fluorescence of the gene product is quenched or enhanced on binding (Guixe et al., 1998; Qi and Grabowski, 1998)
(3) the optical properties of the ligand may be modified on binding of the gene product, for example, the fluorescence of the ligand is quenched or enhanced on binding (Voss, 1993; Masui and Kuramitsu, 1998).
(4) the optical properties of both ligand and gene product are modified on binding, for example, there can be a fluorescence resonance energy transfer (FRET) from ligand to gene product (or vice versa) resulting in emmission at the "acceptor" emmission wavelength when excitation is at the "donor" absoption wavelength (Heim & Tsien, 1996; Mahajan et al., 1998; Miyawaki et al., 1997).

In this embodiment, it is not necessary for binding of the gene product to the genetic element via the ligand to directly induce a change in optical properties. All the gene products to be selected can contain a putative binding domain, which is to be selected for, and a common feature—a tag. The genetic element in each microcapsule is physically linked to the ligand. If the gene product produced from the genetic element has affinity for the ligand, it will bind to it and become physically linked to the same genetic element that encoded it, resulting in the genetic element being 'tagged'. At the end of the reaction, all of the microcapsules are combined, and all genetic elements and gene products pooled together in one environment. Genetic elements encoding gene products exhibiting the desired binding can be selected by adding reagents which specifically bind to, or react specifically with, the "tag" and thereby induce a change in the optical properties of the genetic element allowing there sorting. For example, a fluorescently-labelled anti-"tag" antibody can be used, or an anti-"tag" antibody followed by a second fluorescently labelled antibody which binds the first.

In an alternative embodiment, genetic elements may be sorted on the basis that the gene product, which binds to the ligand, merely hides the ligand from, for example, further binding partners which would otherwise modify the optical properties of the genetic element. In this case genetic elements with unmodified optical properties would be selected.

In an alternative embodiment, the invention provides a method according to the first aspect of the invention, wherein in step (b) the gene products bind to genetic elements encoding them. The gene products together with the attached genetic elements are then sorted as a result of binding of a ligand to gene products having the desired binding activity. For example, all gene products can contain an invariant region which binds covalently or non-covalently to the genetic element, and a second region which is diversified so as to generate the desired binding activity.

In an alternative embodiment, the ligand for the gene product is itself encoded by the genetic element and binds to the genetic element. Stated otherwise, the genetic element encodes two (or indeed more) gene products, at least one of which binds to the genetic element, and which can potentially bind each other. Only when the gene products interact in a microcapsule is the genetic element modified in a way that ultimately results in a change in a change in its optical properties that enables it to be sorted. This embodiment, for example, isused to search gene libraries for pairs of genes encoding pairs of proteins which bind each other.

Fluorescence may be enhanced by the use of Tyramide Signal Amplification (TSA™) amplification to make the genetic elements fluorescent. This involves peroxidase (linked to another protein) binding to the genetic elements and catalysing the conversion of fluorescein-tyramine in to a free radical form which then reacts (locally) with the genetic elements. Methods for performing TSA are known in the art, and kits are available commercially from NEN.

TSA may be configured such that it results in a direct increase in the fluorescence of the genetic element, or such that a ligand is attached to the genetic element which is bound by a second fluorescent molecule, or a sequence of molecules, one or more of which is fluorescent.

(ii) Selection for Catalysis

When selection is for catalysis, the genetic element in each microcapsule may comprise the substrate of the reaction. If the genetic element encodes a gene product capable of acting as a catalyst, the gene product will catalyse the conversion of the substrate into the product. Therefore, at the end of the reaction the genetic element is physically linked to the product of the catalysed reaction.

It may also be desirable, in some cases, for the substrate not to be a component of the genetic element. In this case the substrate would contain an inactive "tag" that requires a further step to activate it such as photoactivation (e.g. of a "caged" biotin analogue, (Sundberg et al., 1995; Pirrung and Huang, 1996)). The catalyst to be selected then converts the substrate to product. The "tag" is then activated and the "tagged" substrate and/or product bound by a tag-binding molecule (e.g. avidin or streptavidin) complexed with the nucleic acid. The ratio of substrate to product attached to the nucleic acid via the "tag" will therefore reflect the ratio of the substrate and product in solution.

The optical properties of genetic elements with product attached and which encode gene products with the desired catalytic activity can be modified by either:

(1) the product-genetic element complex having characteristic optical properties not found in the substrate-genetic element complex, due to, for example;
   (a) the substrate and product having different optical properties (many fluorogenic enzyme substrates are available commercially (see for example Haugland, 1996) including substrates for glycosidases, phosphatases, peptidases and proteases (Craig et al., 1995; Huang et al., 1992; Brynes et al., 1982; Jones et al., 1997; Matayoshi et al., 1990; Wang et al., 1990)), or
   (b) the substrate and product having similar optical properties, but only the product, and not the substrate binds to, or reacts with, the genetic element;
(2) adding reagents which specifically bind to, or react with, the product and which thereby induce a change in the optical properties of the genetic elements allowing their sorting (these reagents can be added before or after breaking the microcapsules and pooling the genetic elements). The reagents;
   (a) bind specifically to, or react specifically with, the product, and not the substrate, if both substrate and product are attached to the genetic element, or
   (b) optionally bind both substrate and product if only the product, and not the substrate binds to, or reacts with, the genetic element.

The pooled genetic elements encoding catalytic molecules can then be enriched by selecting for the genetic elements with modified optical properties.

An alternative is to couple the nucleic acid to a product-specific antibody (or other product-specific molecule). In this scenario, the substrate (or one of the substrates) is present in each microcapsule unlinked to the genetic element, but has a molecular "tag" (for example biotin, DIG or DNP or a fluorescent group). When the catalyst to be selected converts the substrate to product, the product retains the "tag" and is then captured in the microcapsule by the product-specific antibody. In this way the genetic element only becomes associated with the "tag" when it encodes or produces an enzyme capable of converting substrate to product. When all reactions are stopped and the microcapsules are combined, the genetic elements encoding active enzymes will be "tagged" and may already have changed optical properties, for example, if the "tag" was a fluorescent group. Alternatively, a change in optical properties of "tagged" genes can be induced by adding a fluorescently labelled ligand which binds the "tag" (for example fluorescently-labelled avidin/streptavidin, an anti-"tag" antibody which is fluorescent, or a non-fluorescent anti-"tag" antibody which can be detected by a second fluorescently-labelled antibody).

Alternatively, selection may be performed indirectly by coupling a first reaction to subsequent reactions that takes place in the same microcapsule. There are two general ways in which this may be performed. In a first embodiment, the product of the first reaction is reacted with, or bound by, a molecule which does not react with the substrate of the first reaction. A second, coupled reaction will only proceed in the presence of the product of the first reaction. A genetic element encoding a gene product with a desired activity can then be purified by using the properties of the product of the second reaction to induce a change in the optical properties of the genetic element as above.

Alternatively, the product of the reaction being selected may be the substrate or cofactor for a second enzyme-catalysed reaction. The enzyme to catalyse the second reaction can either be translated in situ in the microcapsules or incorporated in the reaction mixture prior to microencapsulation. Only when the first reaction proceeds will the coupled enzyme generate a product which can be used to induce a change in the optical properties of the genetic element as above.

This concept of coupling can be elaborated to incorporate multiple enzymes, each using as a substrate the product of the previous reaction. This allows for selection of enzymes that will not react with an immobilised substrate. It can also be designed to give increased sensitivity by signal amplification if a product of one reaction is a catalyst or a cofactor for a second reaction or series of reactions leading to a selectable product (for example, see Johannsson and Bates, 1988; Johannsson, 1991). Furthermore an enzyme cascade system can be based on the production of an activator for an enzyme or the destruction of an enzyme inhibitor (see Mize et al., 1989). Coupling also has the advantage that a common selection system can be used for a whole group of enzymes which generate the same product and allows for the selection of complicated chemical transformations that cannot be performed in a single step.

Such a method of coupling thus enables the evolution of novel "metabolic pathways" in vitro in a stepwise fashion, selecting and improving first one step and then the next. The selection strategy is based on the final product of the pathway, so that all earlier steps can be evolved independently or sequentially without setting up a new selection system for each step of the reaction.

Expressed in an alternative manner, there is provided a method of isolating one or more genetic elements encoding a gene product having a desired catalytic activity, comprising the steps of:

(1) expressing genetic elements to give their respective gene products;
(2) allowing the gene products to catalyse conversion of a substrate to a product, which may or may not be directly selectable, in accordance with the desired activity;
(3) optionally coupling the first reaction to one or more subsequent reactions, each reaction being modulated by the product of the previous reactions, and leading to the creation of a final, selectable product;
(4) linking the selectable product of catalysis to the genetic elements by either:
   a) coupling a substrate to the genetic elements in such a way that the product remains associated with the genetic elements, or
   b) reacting or binding the selectable product to the genetic elements by way of a suitable molecular "tag" attached to the substrate which remains on the product, or
   c) coupling the selectable product (but not the substrate) to the genetic elements by means of a product-specific reaction or interaction with the product; and
(5) selecting the product of catalysis, together with the genetic element to which it is bound, either by means of its characteristic optical properties, or by adding reagents which specifically bind to, or react specifically with, the product and which thereby induce a change in the optical properties of the genetic elements wherein steps (1) to (6) each genetic element and respective gene product is contained within a microcapsule.

(iii) Selecting for Enzyme Substrate Specificity/Selectivity

Genetic elements encoding enzymes with substrate specificity or selectivity can be specifically enriched by carrying out a positive selection for reaction with one substrate and a negative selection for reaction with another substrate. Such combined positive and negative selection pressure should be of great importance in isolating regio-selective and stereo-selective enzymes (for example, enzymes that can distinguish between two enantiomers of the same substrate). For example, two substrates (e.g. two different enantiomers) are each labelled with different tags (e.g. two different fluorophores) such that the tags become attached to the genetic element by the enzyme-catalysed reaction. If the two tags confer different optical properties on the genetic element the substrate specificity of the enzyme can be determined from the optical properties of the genetic element and those genetic elements encoding gene products with the wrong (or no) specificity rejected. Tags conferring no change in optical activity can also be used if tag-specific ligands with different optical properties are added (e.g. tag-specific antibodies labelled with different fluorophores).

(iv) Selection for Regulation

A similar system can be used to select for regulatory properties of enzymes.

In the case of selection for a regulator molecule which acts as an activator or inhibitor of a biochemical process, the components of the biochemical process can either be translated in situ in each microcapsule or can be incorporated in the reaction mixture prior to microencapsulation. If the genetic element being selected is to encode an activator, selection can be performed for the product of the regulated reaction, as described above in connection with catalysis. If an inhibitor is desired, selection can be for a chemical property specific to the substrate of the regulated reaction.

There is therefore provided a method of sorting one or more genetic elements coding for a gene product exhibiting a desired regulatory activity, comprising the steps of:

(1) expressing genetic elements to give their respective gene products;
(2) allowing the gene products to activate or inhibit a biochemical reaction, or sequence of coupled reactions, in accordance with the desired activity, in such a way as to allow the generation or survival of a selectable molecule;
(3) linking the selectable molecule to the genetic elements either by
  a) having the selectable molecule, or the substrate from which it derives, attached to the genetic elements, or
  b) reacting or binding the selectable product to the genetic elements, by way of a suitable molecular "tag" attached to the substrate which remains on the product, or
  c) coupling the product of catalysis (but not the substrate) to the genetic elements, by means of a product-specific reaction or interaction with the product;
(4) selecting the selectable product, together with the genetic element to which it is bound, either by means of its characteristic optical properties, or by adding reagents which specifically bind to, or react specifically with, the product and which thereby induce a change in the optical properties of the genetic elements wherein steps (1) to (3) each genetic element and respective gene product is contained within a microcapsule.

(v) Selection for Optical Properties of the Gene Product

It is possible to select for inherent optical properties of gene products if, in the microcapsules, the gene product binds back to the genetic element, for example through a common element of the gene product which binds to a ligand which is part of the genetic element. After pooling the genetic elements they can then be sorted using the optical properties of the bound gene products. This embodiment can be used, for example, to select variants of green fluorescent protein (GFP) (Cormack et al., 1996; Delagrave et al., 1995; Ehrig et al., 1995), with improved fluorescence and/or novel absoption and emmission spectra.

(vi) Screening Using Cells

In the current drug discovery paradigm, validated recombinant targets form the basis of in vitro high-throughput screening (HTS) assays. Isolated genetic constructs or polypeptides cannot, however, be regarded as representative of complex biological systems; hence, cell-based systems can provide greater confidence in compound activity in an intact biological system. A wide range of cell-based assays for drug leads are known to those skilled in the art. Cells can be compartmentalised in microcapsules, such as the aqeous microdroplets of a water-in-oil emulsion (Ghadessy, 2001). The effect of a compound(s) on a target can be determined by compartmentalising a cell (or cells) in a microcapsule together with a genetic element(s) and using an appropriate cell-based assay to identify those compartments containing genetic elements with the desired effect on the cell(s). The use of water-in-fluorocarbon emulsions may be particularly advantageous: the high gas dissolving capacity of fluorocarbons can support the exchange of respiratory gases and has been reported to be beneficial to cell culture systems (Lowe, 2002).

(vii) Flow Analysis and Sorting

In a preferred embodiment of the invention the microcapsules will be analysed and, optionally, sorted by flow cytometry. Many formats of microcapsule can be analysed and, optionally, sorted directly using flow cytometry.

In a highly preferred embodiment, microfluidic devices for flow analysis and, optionally, flow sorting (Fu, 2002) of microcapsules will be used. Such a sorting device can be integrated directly on the microfluidic device, and can use electronic means to sort the microcapsules and/or genetic elements. Optical detection, also integrated directly on the microfluidic device, can be used to screen the microcapsules to trigger the sorting. Other means of control of the microcapsules, in addition to charge, can also be incorporated onto the microfluidic device.

A variety of optical properties can be used for analysis and to trigger sorting, including light scattering (Kerker, 1983) and fluorescence polarisation (Rolland et al., 1985). In a highly preferred embodiment the difference in optical properties of the microcapsules or microbeads will be a difference in fluorescence and, if required, the microcapsules or microbeads will be sorted using a microfluidic or conventional fluorescence activated cell sorter (Norman, 1980; Mackenzie and Pinder, 1986), or similar device. Flow cytometry has a series of advantages:

(1) fluorescence activated cell sorting equipment from established manufacturers (e.g. Becton-Dickinson, Coulter, Cytomation) allows the analysis and sorting at up to 100,000 microcapsules or microbeads per second.
(2) the fluorescence signal from each microcapsule or microbead corresponds tightly to the number of fluorescent molecules present. As little as few hundred fluorescent molecules per microcapsules or microbeads can be quantitatively detected;

(3) the wide dynamic range of the fluorescence detectors (typically 4 log units) allows easy setting of the stringency of the sorting procedure, thus allowing the recovery of the optimal number microcapsules or microbeads from the starting pool (the gates can be set to separate microcapsules or microbeads with small differences in fluorescence or to only separate out microcapsules or microbeads with large differences in fluorescence, dependant on the selection being performed);

(4) fluorescence-activated cell sorting equipment can perform simultaneous excitation and detection at multiple wavelengths (Shapiro, 1995). allowing positive and negative selections to be performed simultaneously by monitoring the labelling of the microcapsules or microbeads with two to thirteen (or more) fluorescent markers, for example, if substrates for two alternative targets are labelled with different fluorescent tags the microcapsules or microbeads can labelled with different fluorophores dependent on the target regulated.

If the microcapsules or microbeads are optically tagged, flow cytometry can also be used to identify the genetic element or genetic elements in the microcapsule or coated on the microbeads (see below). Optical tagging can also be used to identify the concentration of reagents in the microcapsule (if more than one concentration is used in a single experiment) or the number of compound molecules coated on a microbead (if more than one coating density is used in a single experiment). Furthermore, optical tagging can be used to identify the target in a microcapsule (if more than one target is used in a single experiment). This analysis can be performed simultaneously with measuring activity, after sorting of microcapsules containing microbeads, or after sorting of the microbeads.

(viii) Microcapsule Identification and Sorting

The invention provides for the identification and, optionally, the sorting of intact microcapsules where this is enabled by the sorting techniques being employed. Microcapsules may be identified and, optionally, sorted as such when the change induced by the desired genetic element either occurs or manifests itself at the surface of the microcapsule or is detectable from outside the microcapsule. The change may be caused by the direct action of the gene product, or indirect, in which a series of reactions, one or more of which involve the gene product having the desired activity leads to the change. For example, where the microcapsule is a membranous microcapsule, the microcapsule may be so configured that a component or components of the biochemical system comprising the target are displayed at its surface and thus accessible to reagents which can detect changes in the biochemical system regulated by the gene product within the microcapsule.

In a preferred aspect of the invention, however, microcapsule identification and, optionally, sorting relies on a change in the optical properties of the microcapsule, for example absorption or emission characteristics thereof, for example alteration in the optical properties of the microcapsule resulting from a reaction leading to changes in absorbance, luminescence, phosphorescence or fluorescence associated with the microcapsule. All such properties are included in the term "optical". In such a case, microcapsules can be identified and, optionally, sorted by luminescence, fluorescence or phosphorescence activated sorting. In a highly preferred embodiment, flow cytometry is employed to analyse and, optionally, sort microcapsules containing gene products having a desired activity which result in the production of a fluorescent molecule in the microcapsule.

The methods of the current invention allow reagents to be mixed rapidly (in <2 ms), hence a spatially-resolved optical image of microcapsules in microfluidic network allows time resolved measurements of the reactions in each microcapsule. Microcapsules can, optionally, be separated using a microfluidic flow sorter to allow recovery and further analysis or manipulation of the molecules they contain. Advantageously, the flow sorter would be an electronic flow sorting device. Such a sorting device can be integrated directly on the microfluidic device, and can use electronic means to sort the microcapsules. Optical detection, also integrated directly on the microfluidic device, can be used to screen the microcapsules to trigger the sorting. Other means of control of the microcapsules, in addition to charge, can also be incorporated onto the microfluidic device.

In an alternative embodiment, a change in microcapsule fluorescence, when identified, is used to trigger the modification of the microbead within the compartment. In a preferred aspect of the invention, microcapsule identification relies on a change in the optical properties of the microcapsule resulting from a reaction leading to luminescence, phosphorescence or fluorescence within the microcapsule. Modification of the microbead within the microcapsules would be triggered by identification of luminescence, phosphorescence or fluorescence. For example, identification of luminescence, phosphorescence or fluorescence can trigger bombardment of the compartment with photons (or other particles or waves) which leads to modification of the microbead or molecules attached to it. A similar procedure has been described previously for the rapid sorting of cells (Keij et al., 1994). Modification of the microbead may result, for example, from coupling a molecular "tag", caged by a photolabile protecting group to the microbeads: bombardment with photons of an appropriate wavelength leads to the removal of the cage. Afterwards, all microcapsules are combined and the microbeads pooled together in one environment. Genetic elements exhibiting the desired activity can be selected by affinity purification using a molecule that specifically binds to, or reacts specifically with, the "tag".

(ix) Flow Sorting of Genetic Elements

In a preferred embodiment of the invention the genetic elements will be sorted by flow cytometry. A variety of optical properties can be used to trigger sorting, including light scattering (Kerker, 1983) and fluorescence polarisation (Rolland et al., 1985). In a highly preferred embodiment the difference in optical properties of the genetic elements will be a difference in fluorescence and the genetic elements will be sorted using a fluorescence activated cell sorter (Norman, 1980; Mackenzie and Pinder, 1986), or similar device. Such a sorting device can be integrated directly on the microfluidic device, and can use electronic means to sort the genetic elements. Optical detection, also integrated directly on the microfluidic device, can be used to screen the genetic elements to trigger the sorting. Other means of control of the genetic elements, in addition to charge, can also be incorporated onto the microfluidic device. In an especially preferred embodiment the genetic element comprises of a nonfluorescent nonmagnetic (e.g. polystyrene) or paramagnetic microbead (see Formusek and Vetvicka, 1986), optimally 0.6 to 1.0 µm diameter, to which are attached both the gene and the groups involved in generating a fluorescent signal:

(1) commercially available fluorescence activated cell sorting equipment from established manufacturers (e.g.

Becton-Dickinson, Coulter) allows the sorting of up to $10^8$ genetic elements (events) per hour;

(2) the fluorescence signal from each bead corresponds tightly to the number of fluorescent molecules attached to the bead. At present as little as few hundred fluorescent molecules per particle can be quantitatively detected;

(3) the wide dynamic range of the fluorescence detectors (typically 4 log units) allows easy setting of the stringency of the sorting procedure, thus allowing the recovery of the optimal number of genetic elements from the starting pool (the gates can be set to separate beads with small differences in fluorescence or to only separate out beads with large differences in fluorescence, dependant on the selection being performed;

(4) commercially available fluorescence-activated cell sorting equipment can perform simultaneous excitation at up to two different wavelengths and detect fluorescence at up to four different wavelengths (Shapiro, 1983) allowing positive and negative selections to be performed simultaneously by monitoring the labelling of the genetic element with two (or more) different fluorescent markers, for example, if two alternative substrates for an enzyme (e.g. two different enantiomers) are labelled with different fluorescent tags the genetic element can labelled with different fluorophores dependent on the substrate used and only genes encoding enzymes with enantioselectivity selected.

(5) highly uniform derivatised and non-derivatised non-magnetic and paramagnetic microparticles (beads) are commercially available from many sources (e.g. Sigma, and Molecular Probes) (Formusek and Vetvicka, 1986).

(x) Multi-Step Procedure

It will be also be appreciated that according to the present invention, it is not necessary for all the processes of transcription/replication and/or translation, and selection to proceed in one single step, with all reactions taking place in one microcapsule. The selection procedure may comprise two or more steps. First, transcription/replication and/or translation of each genetic element of a genetic element library may take place in a first microcapsule. Each gene product is then linked to the genetic element which encoded it (which resides in the same microcapsule), for example via a gene product-specific ligand such as an antibody. The microcapsules are then broken, and the genetic elements attached to their respective gene products optionally purified. Alternatively, genetic elements can be attached to their respective gene products using methods which do not rely on encapsulation. For example phage display (Smith, G. P., 1985), polysome display (Mattheakkis et al., 1994), RNA-peptide fusion (Roberts and Szostak, 1997) or lac repressor peptide fusion (Cull, et al., 1992).

In the second step of the procedure, each purified genetic element attached to its gene product is put into a second microcapsule containing components of the reaction to be selected. This reaction is then initiated. After completion of the reactions, the microcapsules are again broken and the modified genetic elements are selected. In the case of complicated multistep reactions in which many individual components and reaction steps are involved, one or more intervening steps may be performed between the initial step of creation and linking of gene product to genetic element, and the final step of generating the selectable change in the genetic element.

If necessary, release of the gene product from the genetic element within a secondary microcapsule can be achieved in a variety of ways, including by specific competition by a low-molecular weight product for the binding site or cleavage of a linker region joining the binding domain of the gene product from the catalytic domain either enzymatically (using specific proteases) or autocatalytically (using an integrin domain).

(xi) Selection by Activation of Reporter Gene Expression In Situ

The system can be configured such that the desired binding, catalytic or regulatory activity encoded by a genetic element leads, directly or indirectly to the activation of expression of a "reporter gene" that is present in all microcapsules. Only gene products with the desired activity activate expression of the reporter gene. The activity resulting from reporter gene expression allows the selection of the genetic element (or of the compartment containing it) by any of the methods described herein.

For example, activation of the reporter gene may be the result of a binding activity of the gene product in a manner analogous to the "two hybrid system" (Fields and Song, 1989). Activation can also result from the product of a reaction catalysed by a desirable gene product. For example, the reaction product can be a transcriptional inducer of the reporter gene. For example arabinose may be used to induce transcription from the araBAD promoter. The activity of the desirable gene product can also result in the modification of a transcription factor, resulting in expression of the reporter gene. For example, if the desired gene product is a kinase or phosphatase the phosphorylation or dephosphorylation of a transcription factor may lead to activation of reporter gene expression.

(xii) Amplification

According to a further aspect of the present invention the method comprises the further step of amplifying the genetic elements. Selective amplification may be used as a means to enrich for genetic elements encoding the desired gene product.

In all the above configurations, genetic material comprised in the genetic elements may be amplified and the process repeated in iterative steps. Amplification may be by the polymerase chain reaction (Saiki et al., 1988) or by using one of a variety of other gene amplification techniques including; Qb replicase amplification (Cahill, Foster and Mahan, 1991; Chetverin and Spirin, 1995; Katanaev, Kurnasov and Spirin, 1995); the ligase chain reaction (LCR) (Landegren et al., 1988; Barany, 1991); the self-sustained sequence replication system (Fahy, Kwoh and Gingeras, 1991) and strand displacement amplification (Walker et al., 1992). Advantageously, the amplification procedure can be performed in a microfluidic device.

(C) Rapid Mixing of Reagents in Microcapsules

Advantageously, after fusion of microcpasules, the reagents contained in the fused microcapsule can be mixed rapidly using chaotic advection by passing the droplets through channels that disrupt the laminar flow lines of the fluid within the droplets, their contents can be rapidly mixed, fully initiating any chemical reactions.

(D) Sensing Microcapsule Characteristics

In certain aspects of the invention, sensors are provided that can sense and/or determine one or more characteristics of the fluidic droplets, and/or a characteristic of a portion of the fluidic system containing the fluidic droplet (e.g., the liquid surrounding the fluidic droplet) in such a manner as to allow the determination of one or more characteristics of the fluidic droplets. Characteristics determinable with respect to the droplet and usable in the invention can be identified by those of ordinary skill in the art. Non-limiting examples of such characteristics include fluorescence, spectroscopy (e.g., optical, infrared, ultraviolet, etc.), radioactivity, mass, volume, density, temperature, viscosity, pH, concentration of a substance, such as a biological substance (e.g., a protein, a nucleic acid, etc.), or the like.

In some cases, the sensor may be connected to a processor, which in turn, causes an operation to be performed on the fluidic droplet, for example, by sorting the droplet, adding or removing electric charge from the droplet, fusing the droplet with another droplet, splitting the droplet, causing mixing to occur within the droplet, etc., for example, as previously described. For instance, in response to a sensor measurement of a fluidic droplet, a processor may cause the fluidic droplet to be split, merged with a second fluidic droplet, sorted etc.

One or more sensors and/or processors may be positioned to be in sensing communication with the fluidic droplet. "Sensing communication," as used herein, means that the sensor may be positioned anywhere such that the fluidic droplet within the fluidic system (e.g., within a channel), and/or a portion of the fluidic system containing the fluidic droplet may be sensed and/or determined in some fashion. For example, the sensor may be in sensing communication with the fluidic droplet and/or the portion of the fluidic system containing the fluidic droplet fluidly, optically or visually, thermally, pneumatically, electronically, or the like. The sensor can be positioned proximate the fluidic system, for example, embedded within or integrally connected to a wall of a channel, or positioned separately from the fluidic system but with physical, electrical, and/or optical communication with the fluidic system so as to be able to sense and/or determine the fluidic droplet and/or a portion of the fluidic system containing the fluidic droplet (e.g., a channel or a microchannel, a liquid containing the fluidic droplet, etc.). For example, a sensor may be free of any physical connection with a channel containing a droplet, but may be positioned so as to detect electromagnetic radiation arising from the droplet or the fluidic system, such as infrared, ultraviolet, or visible light. The electromagnetic radiation may be produced by the droplet, and/or may arise from other portions of the fluidic system (or externally of the fluidic system) and interact with the fluidic droplet and/or the portion of the fluidic system containing the fluidic droplet in such as a manner as to indicate one or more characteristics of the fluidic droplet, for example, through absorption, reflection, diffraction, refraction, fluorescence, phosphorescence, changes in polarity, phase changes, changes with respect to time, etc. As an example, a laser may be directed towards the fluidic droplet and/or the liquid surrounding the fluidic droplet, and the fluorescence of the fluidic droplet and/or the surrounding liquid may be determined. "Sensing communication," as used herein may also be direct or indirect. As an example, light from the fluidic droplet may be directed to a sensor, or directed first through a fiber optic system, a waveguide, etc., before being directed to a sensor.

Non-limiting examples of sensors useful in the invention include optical or electromagnetically-based systems. For example, the sensor may be a fluorescence sensor (e.g., stimulated by a laser), a microscopy system (which may include a camera or other recording device), or the like. As another example, the sensor may be an electronic sensor, e.g., a sensor able to determine an electric field or other electrical characteristic. For example, the sensor may detect capacitance, inductance, etc., of a fluidic droplet and/or the portion of the fluidic system containing the fluidic droplet.

As used herein, a "processor" or a "microprocessor" is any component or device able to receive a signal from one or more sensors, store the signal, and/or direct one or more responses (e.g., as described above), for example, by using a mathematical formula or an electronic or computational circuit. The signal may be any suitable signal indicative of the environmental factor determined by the sensor, for example a pneumatic signal, an electronic signal, an optical signal, a mechanical signal, etc.

As a particular non-limiting example, a device of the invention may contain fluidic droplets containing one or more cells. The desired activity of one or more gene products may result in the expression (or inhibition of expression) of a 'marker' gene, for example a gene for green fluorescent protein (GFP). The cells may be exposed to a fluorescent signal marker that binds if a certain condition is present, for example, the marker may bind to a first cell type but not a second cell type, the marker may bind to an expressed protein, the marker may indicate viability of the cell (i.e., if the cell is alive or dead), the marker may be indicative of the state of development or differentiation of the cell, etc., and the cells may be directed through a fluidic system of the invention based on the presence/absence, and/or magnitude of the fluorescent signal marker. For instance, determination of the fluorescent signal marker may cause the cells to be directed to one region of the device (e.g., a collection chamber), while the absence of the fluorescent signal marker may cause the cells to be directed to another region of the device (e.g., a waste chamber). Thus, in this example, a population of cells may be screened and/or sorted on the basis of one or more determinable or targetable characteristics of the cells, for example, to select live cells, cells expressing a certain protein, a certain cell type, etc.

(E) Materials

A variety of materials and methods, according to certain aspects of the invention, can be used to form any of the above-described components of the microfluidic systems and devices of the invention. In some cases, the various materials selected lend themselves to various methods. For example, various components of the invention can be formed from solid materials, in which the channels can be formed via micromachining, film deposition processes such as spin coating and chemical vapor deposition, laser fabrication, photolithographic techniques, etching methods including wet chemical or plasma processes, and the like. See, for example, Scientific American, 248:44-55, 1983 (Angell, et al). In one embodiment, at least a portion of the fluidic system is formed of silicon by etching features in a silicon chip. Technologies for precise and efficient fabrication of various fluidic systems and devices of the invention from silicon are known. In another embodiment, various components of the systems and devices of the invention can be formed of a polymer, for example, an elastomeric polymer such as polydimethylsiloxane ("PDMS"), polytetrafluoroethylene ("PTFE" or Teflon®), or the like.

Different components can be fabricated of different materials. For example, a base portion including a bottom wall and side walls can be fabricated from an opaque material such as silicon or PDMS, and a top portion can be fabricated from a transparent or at least partially transparent material, such as glass or a transparent polymer, for observation and/or control of the fluidic process. Components can be coated so as to expose a desired chemical functionality to fluids that contact interior channel walls, where the base supporting material does not have a precise, desired functionality. For example, components can be fabricated as illustrated, with interior channel walls coated with another material. Material used to fabricate various components of the systems and devices of the invention, e.g., materials used to coat interior walls of fluid channels, may desirably be selected from among those materials that will not adversely affect or be affected by fluid flowing through the fluidic system, e.g., material(s) that is chemically inert in the presence of fluids to be used within the device.

In one embodiment, various components of the invention are fabricated from polymeric and/or flexible and/or elastomeric materials, and can be conveniently formed of a hardenable fluid, facilitating fabrication via molding (e.g. replica molding, injection molding, cast molding, etc.). The hardenable fluid can be essentially any fluid that can be induced to solidify, or that spontaneously solidifies, into a solid capable of containing and/or transporting fluids contemplated for use in and with the fluidic network. In one embodiment, the hardenable fluid comprises a polymeric liquid or a liquid polymeric precursor (i.e. a "prepolymer"). Suitable polymeric liquids can include, for example, thermoplastic polymers, thermoset polymers, or mixture of such polymers heated above their melting point. As another example, a suitable polymeric liquid may include a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art. A variety of polymeric materials, many of which are elastomeric, are suitable, and are also suitable for forming molds or mold masters, for embodiments where one or both of the mold masters is composed of an elastomeric material. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Non-limiting examples of silicone elastomers suitable for use according to the invention include those formed from precursors including the chlorosilanes such as methylchlorosilanes, ethylchlorosilanes, phenylchlorosilanes, etc.

Silicone polymers are preferred in one set of embodiments, for example, the silicone elastomer polydimethylsiloxane. Non-limiting examples of PDMS polymers include those sold under the trademark Sylgard by Dow Chemical Co., Midland, Mich., and particularly Sylgard 182, Sylgard 184, and Sylgard 186. Silicone polymers including PDMS have several beneficial properties simplifying fabrication of the microfluidic structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, about an hour. Also, silicone polymers, such as PDMS, can be elastomeric and thus may be useful for forming very small features with relatively high aspect ratios, necessary in certain embodiments of the invention. Flexible (e.g., elastomeric) molds or masters can be advantageous in this regard.

One advantage of forming structures such as microfluidic structures of the invention from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, components can be fabricated and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Specifically, in addition to being irreversibly sealable to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in the art, for example, in an article entitled "Rapid Prototyping of Microfluidic Systems and Polydimethylsiloxane," *Anal. Chem.*, 70:474-480, 1998 (Duffy et al.), incorporated herein by reference.

Another advantage to forming microfluidic structures of the invention (or interior, fluid-contacting surfaces) from oxidized silicone polymers is that these surfaces can be much more hydrophilic than the surfaces of typical elastomeric polymers (where a hydrophilic interior surface is desired). Such hydrophilic channel surfaces can thus be more easily filled and wetted with aqueous solutions than can structures comprised of typical, unoxidized elastomeric polymers or other hydrophobic materials.

In one embodiment, a bottom wall is formed of a material different from one or more side walls or a top wall, or other components. For example, the interior surface of a bottom wall can comprise the surface of a silicon wafer or microchip, or other substrate. Other components can, as described above, be sealed to such alternative substrates. Where it is desired to seal a component comprising a silicone polymer (e.g. PDMS) to a substrate (bottom wall) of different material, the substrate may be selected from the group of materials to which oxidized silicone polymer is able to irreversibly seal (e.g., glass, silicon, silicon oxide, quartz, silicon nitride, polyethylene, polystyrene, epoxy polymers, and glassy carbon surfaces which have been oxidized). Alternatively, other sealing techniques can be used, as would be apparent to those of ordinary skill in the art, including, but not limited to, the use of separate adhesives, thermal bonding, solvent bonding, ultrasonic welding, etc.

Various aspects and embodiments of the present invention are illustrated in the following examples. It will be appreciated that modification of detail may be made without departing from the scope of the invention.

All documents mentioned in the text are incorporated by reference.

EXAMPLES

Example 1

Figure 15:
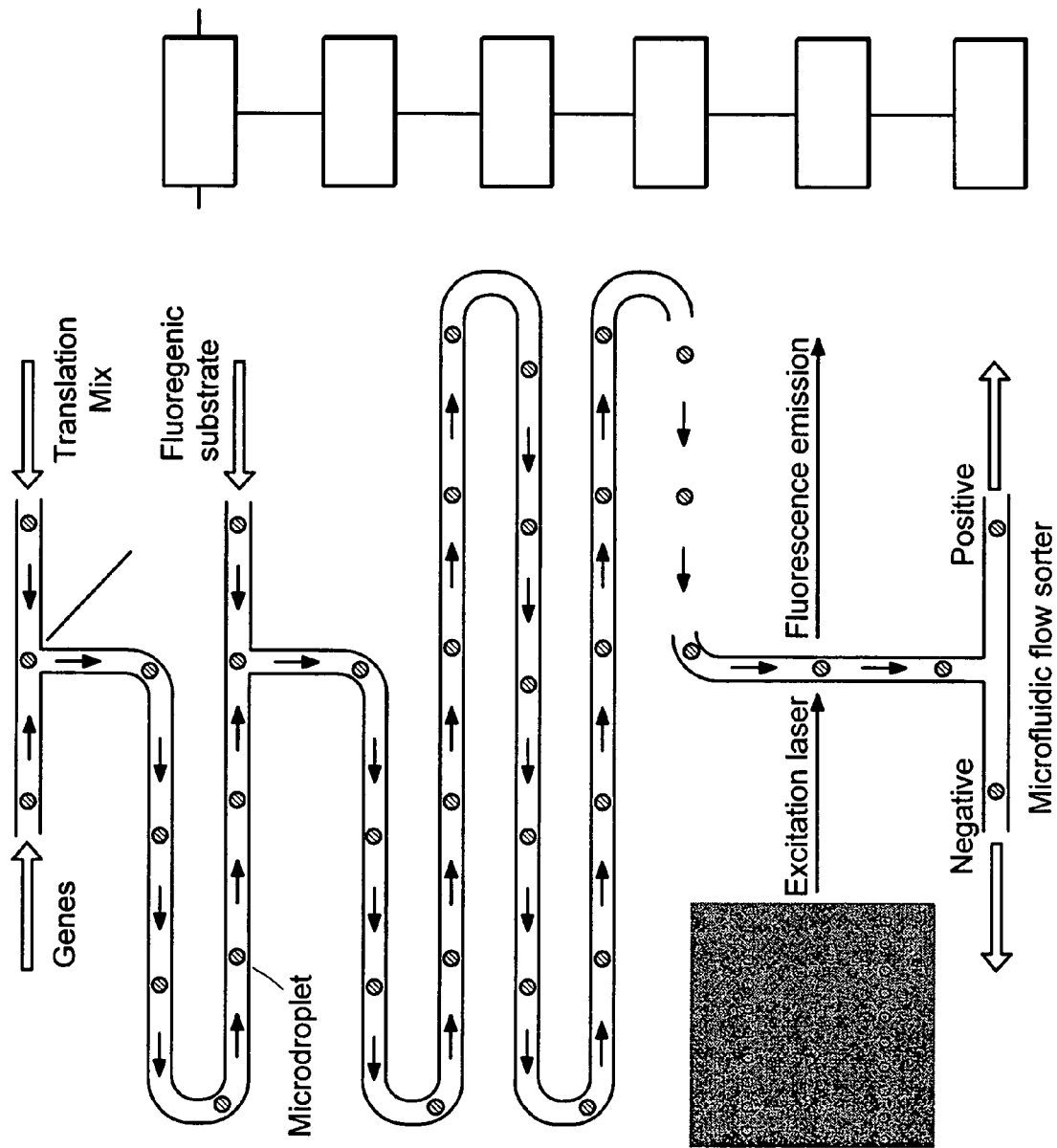
FIG. 15. Directed evolution of enzymes using microdroplets in a microfluidic system. Panel A: schematic of the core system. Panel B: process block diagram showing the modules in the core system. Libraries of mutated enzyme genes are encapsulated in aqueous microdroplets (FIG. 16A) such that, statistically, the majority of droplets contain no more than one gene per droplet. Each of these microdroplets is fused with a second microdroplet (FIG. 16C) containing an in vitro translation system. After allowing time for the genes to be translated into protein each microdroplet is fused with another microdroplet containing an inhibitor of translation (puromycin) and a fluorogenic enzyme substrate. The rate of the enzymatic reaction is determined by measuring the fluorescence of each microdroplet, ideally at multiple points (corresponding to different times). Microdroplets with catalyic rates over a desired threshold value (e.g. the fastest 1%) will be sorted (FIG. 16D) and collected and the genes contained therein amplified using the polymerase chain reaction (PCR). The selected genes will then either be characterised, re-selected directly, or first re-mutated randomly, or recombined before re-selection.
Figure 16A:
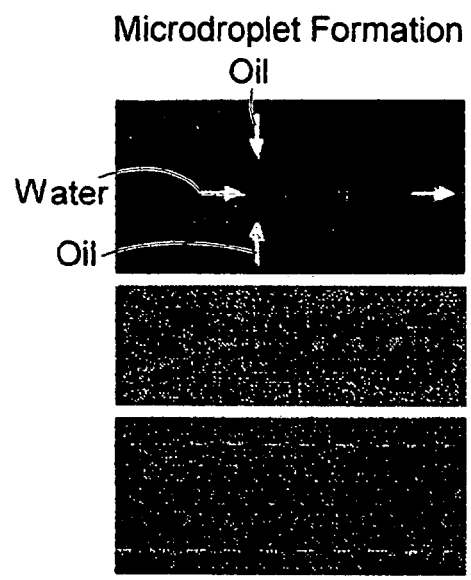
FIG. 16. Examples of microdroplet formation and manipulation using microfluidics. Panel A: microdroplets can be created at up to $10^4$ sec$^{-1}$ by hydrodynamic-focussing (top two panels) and show <1.5% polydispersity (bottom panel). Panel B: microdroplets can be split symmetrically or asymmetrically. Panel C: microdroplets carrying positive (+q) and negative (−q) electrical charges fuse spontaneously. Panel D: charged microdroplets can also be steered using an applied electrical field (E).
Figure 16B:
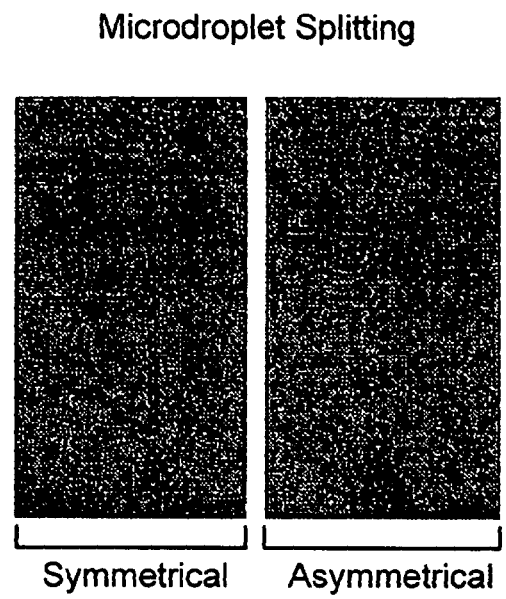
Figure 16C:
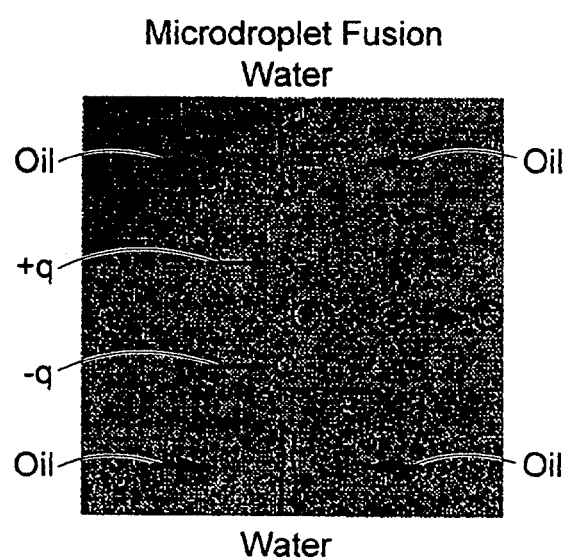
Figure 16D:
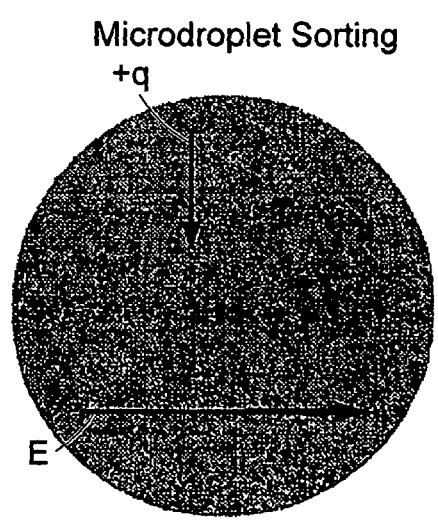

Microfluidic Device for Selection of Genes Using In Vitro Compartmentalisation A schematic representation of the microfluidic device is shown in FIG. 15. Microchannels are fabricated with rectangular cross-sections using rapid prototyping in poly(dimethylsiloxane) (PDMS) (McDonald and Whitesides, 2002) and rendered hydrophobic as (Song and Ismagilov, 2003). Syringe pumps were used to drive flows (Harvard Apparatus PHD 2000 Infusion pumps). For aqueous solutions, 250 µl Hamilton Gastight syringes (1700 series, TLL) with removeable needles of 27-gauge are used with 30-gauge Teflon tubing (Weico Wire and Cable). For the carrier fluid, 1 ml Hamilton Gastight syringes (1700 series, TLL) are used with 30-gauge Teflon needles with one hub from Hamilton (Song and Ismagilov, 2003). The carrier fluid is 9% (v/v) $C_6F_{11}C_2H_4OH$ in perfluorodecaline (PFD) (Song et al., 2003). The microfluidic device consists of a series of interconnected modules. Each module has a specific function. These include modules that will produce droplets, fuse droplets, mix droplets, react droplets, detect droplets, and sort droplets (see FIG. 16). In one example, droplets are made, consisting of different molecules or different concentrations of molecules. Droplets are made at rates of up to $10^4$ sec$^{-1}$, and are made with a polydispersity of less than 1.5% and with sizes ranging from 1 μm to 100 μm. Each droplet is fused with a second droplet containing a second set of reactants, and is rapidly mixed to initiate the chemical reaction. This chemical reaction is allowed to proceed in each droplet by passing it through a delay channel. Each droplet is then fused with another droplet containing a second set of reactants, and is subsequently rapidly mixed to initiate the second set of chemical reactions. After the second reaction has proceeded in a delay module, the results of the reaction is determined using an optical sensor or other form of detection module. Finally, the desired droplets are sorted into two populations based on signal form the optical detection module, one population is kept for further processing and the other discarded. These and other modules can be used in this combination, or in other combinations.

Figure 17A:
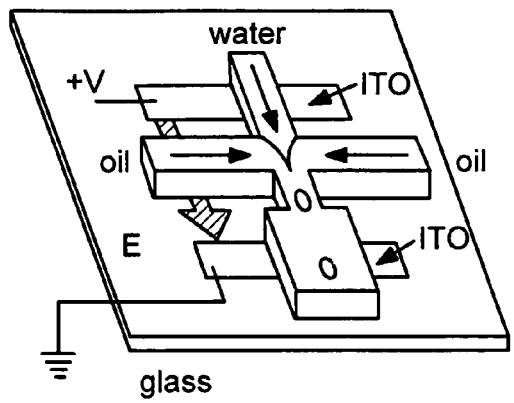
FIG. 17 Charged droplet generation. (A), Oil and water streams converge at a 30 micron orifice. A voltage V applied to indium-tin-oxide (ITO) electrodes on the glass produces an electric field E to capacitively charges the aqueous-oil interface. Drop size is independent of charge at low field strengths but decreases at higher fields, as shown in the photomicrographs, [(B) V=0, (C) V=400, (D) V=600 and (E) V=800] at higher fields. (F) Droplet size as a function of voltage showing the crossover between flow-dominated and field-dominated snap-off for three different flow rates of the continuous phase oil ($Q_c$=80 nL/s, 110 nL/s, and 140 nL/s). The infusion rate of the water is constant $Q_d$=20 nL/s.}
Figure 17B:
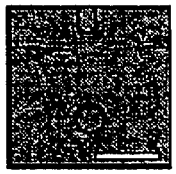
Figure 17C:
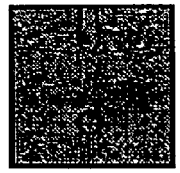
Figure 17D:
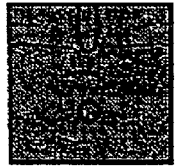
Figure 17E:
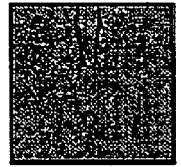
Figure 17F:
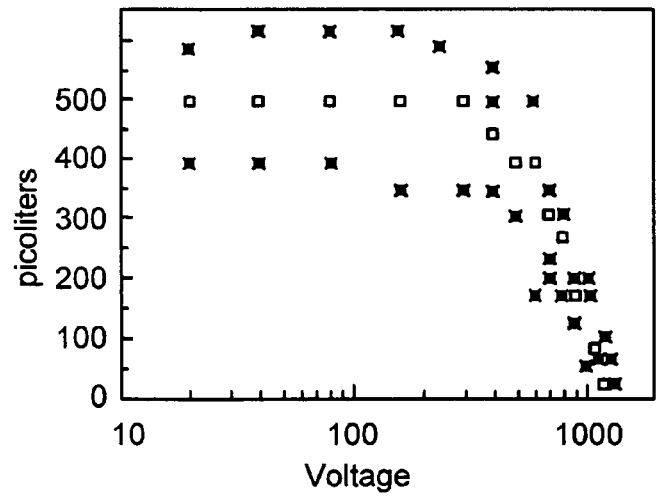

Droplet generation module: We use a flow-focusing geometry to form the drops. A water stream is infused from one channel through a narrow constriction; counter propagating oil streams hydrodynamically focus the water stream reducing its size as it passes through the constriction as shown in FIG. 17A. This droplet generator can be operated in a flow regime that produces a steady stream of uniform droplets of water in oil. The size of the water droplets is controlled by the relative flow rates of the oil and the water; the viscous forces overcome surface tension to create uniform droplets. If the flow rate of the water is too high a longer jet of fluid passes through the orifice and breaks up into droplets further down stream; these droplets are less uniform in size. If the flow rate of the water is too low, the droplet breakup in the orifice becomes irregular again, producing a wider range of droplet sizes. While this emulsification technology is robust, it is limited to producing droplets of one size at any given flow rate; this droplet size is largely determined by the channel dimensions. Moreover, the timing of the droplet production cannot be controlled.

We overcome these limitations by incorporating electric fields to create an electrically addressable emulsification system. To achieve this, we apply high voltage to the aqueous stream and charge the oil water interface, as shown schematically in FIG. 17A. The water stream behaves as a conductor while the oil is an insulator; electrochemical reactions charge the fluid interface like a capacitor. At snap-off, charge on the interface remains on the droplet. In addition, the droplet volume, $V_d$, and frequency, f, can be tailored over nearly three orders of magnitude without changing the infusion rate of the oil or water. Droplet size and frequency are not independent; instead their product is determined by the infusion rate of the dispersed phase $Q_d = f V_d$. The droplet size decreases with increasing field strength, as shown in FIGS. 17, B to E. The dependence of the droplet size on applied voltage for three different flow rates is summarized in FIG. 17F. At low applied voltages the electric field has a negligible effect, and droplet formation is driven exclusively by the competition between surface tension and viscous flow. By contrast, at high electric field strengths, there is a significant additional force on the growing drop, F=qE, where q is the charge on the droplet. Since the droplet interface behaves as a capacitor, q is proportional to the applied voltage, V. This leads to a $V^2$ dependence of the force, which accounts for the decrease in droplet size with increasing applied field shown in FIG. 17F. If the electric field becomes too large, the charged interface of the water stream is repelled by the highly charged drops; this destabilizes the production and increases the variation in droplet size.

The electronic control afforded by the field-induced droplet formation provides an additional valuable benefit: it allows the phase of the droplet break-off to be adjusted within the production cycle. This is accomplished by increasing the field above the critical break-off field only at the instant the droplet is required. This provides a convenient means to precisely synchronize the production and arrival of individual droplets at specific locations.

Droplet coalescer module: An essential component in any droplet-based reaction-confinement system is a droplet coalescing module which combines two or more reagents to initiate a chemical reaction. This is particularly difficult to achieve in a microfluidic device because surface tension, surfactant stabilization, and drainage forces all hinder droplet coalescence; moreover, the droplets must cross the stream lines that define their respective flows and must be perfectly synchronized to arrive at a precise location for coalescence.

Use of electrostatic charge overcomes these difficulties; placing charges of opposite sign on each droplet and applying an electric field forces them to coalesce. As an example we show a device consisting of two separate nozzles that generate droplets with different compositions and opposite charges, sketched in FIG. 18A. The droplets are brought together at the confluence of the two streams. The electrodes used to charge the droplets upon formation also provide the electric field to force the droplets across the stream lines, leading to coalesce. Slight variations in the structure of the two nozzles result in slight differences in the frequency and phase of their droplet generation in the absence of a field. Thus the droplets differ in size even though the infusion rates are identical. Moreover, the droplets do not arrive at the point of confluence at exactly the same time. As a result the droplets do not coalesce as shown in FIG. 18B. By contrast, upon application of an electric field, droplet formation becomes exactly synchronized, ensuring that pairs of identically sized droplets each reach the point of confluence simultaneously. Moreover, the droplets are oppositely charged, forcing them to traverse the stream lines and contact each other, thereby causing them to coalesce, as shown in FIG. 18C. The remarkable synchronization of the droplet formation results from coupling of the break-off of each of the pair of droplets as mediated by the electric field; the magnitude of the electric field varies as the separation between the leading edges of the two droplets changes and the frequency of droplet break-off is mode-locked to the electric field. A minimum charge is required to cause droplets to coalesce, presumably because of the stabilizing effects of the surfactant coating; this is clear from FIG. 18D which shows the voltage dependence of the percentage of drops that contact each other that actually coalesce.

Figure 19A:
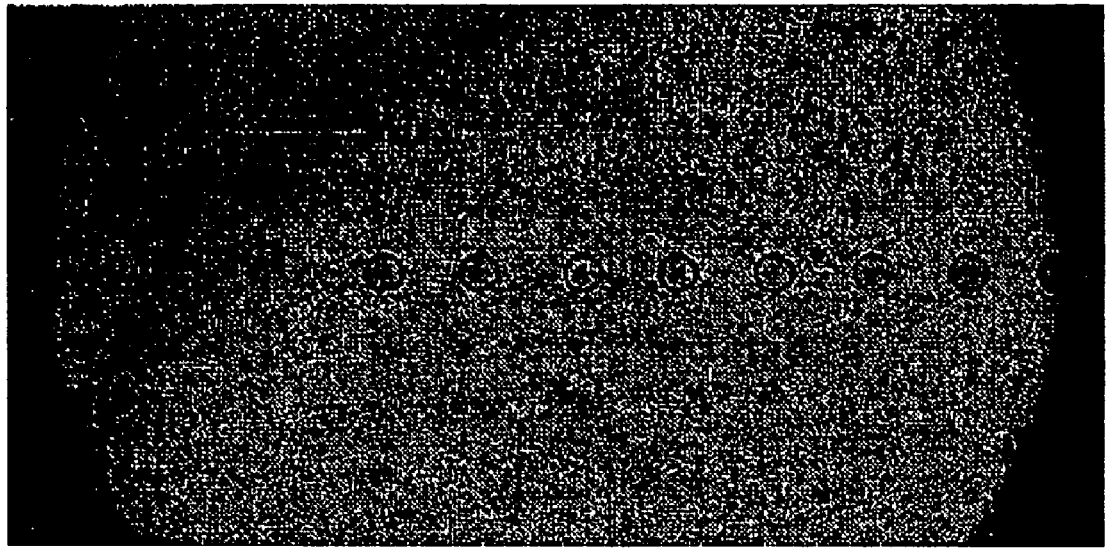
FIG. 19: Droplets carrying a pH sensitive dye coalesce with droplets of a different pH fluid. Chaotic advection rapidly mixes the two fluids through a combination of translation and rotation as the droplets pass around corners.
Figure 19B:
Figure 20A:
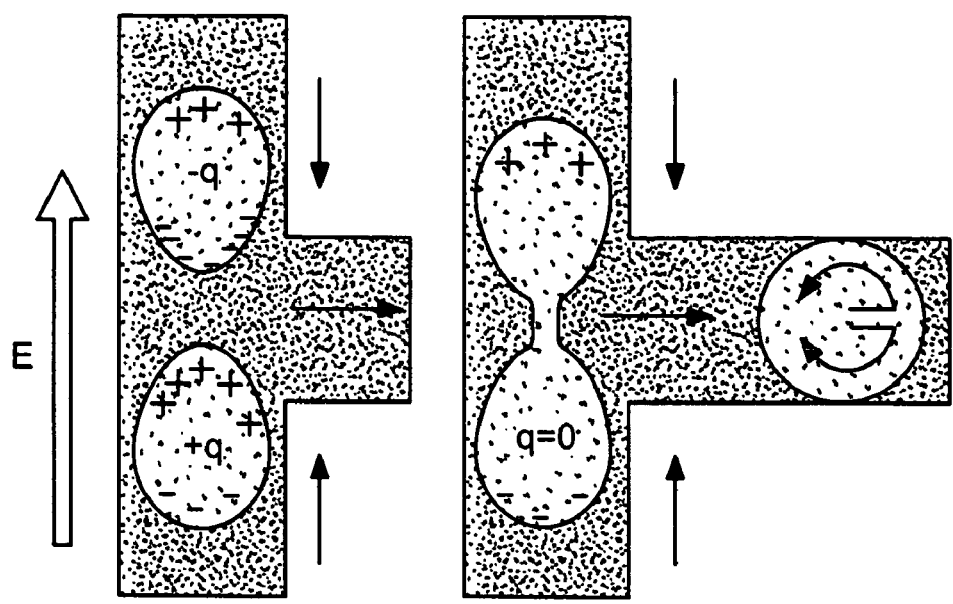
FIG. 20: Diffusion limited and rapid mixing strategies. (A) Drops meet and coalesce along the direction of E and then move off in a perpendicular direction, as sketched the counter rotating vortices after coalescence do not mix the two fluid parts as each vortex contains a single material. (B) As the drops approach each other the increasing field causes there interfaces to deform and (C) a bridge to jump out connecting the drops, to create (D) in the case of 20 nm silica particles and MgCl_2 a sharp interface where the particles begin to gel. (E) A typical unmixed droplet with particles in one hemisphere. (F) To achieve fast mixing, droplets are brought together in the direction perpendicular to the electric field and move off in the direction parallel to the direction they merged along. Counter rotating vortexes are then created where each vortex is composed of half of the contentes from each of the pre-merger-droplets. (G) Shows a pH sensitive dye in the lower drop and a different pH fluid in the upper droplet. (H) After merger the droplets are split by a sharp line. (I) A uniform intensity indicating that mixing has been occurred is achieved in the droplet after it translates one diameter, typically this takes 1 to 2 ms.
Figure 20B:
Figure 20C:
Figure 20D:
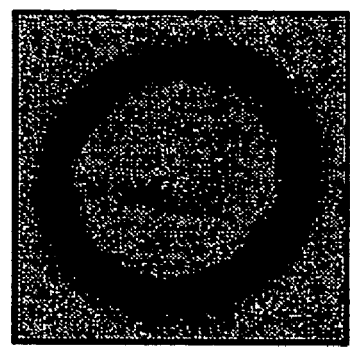
Figure 20E:

Droplet mixer module: Rapid mixing is achieved through either successive iterations of translation and rotation, FIG. 19, or by coalescing drops along the direction parallel to the flow direction, FIG. 20.

Figure 21A:
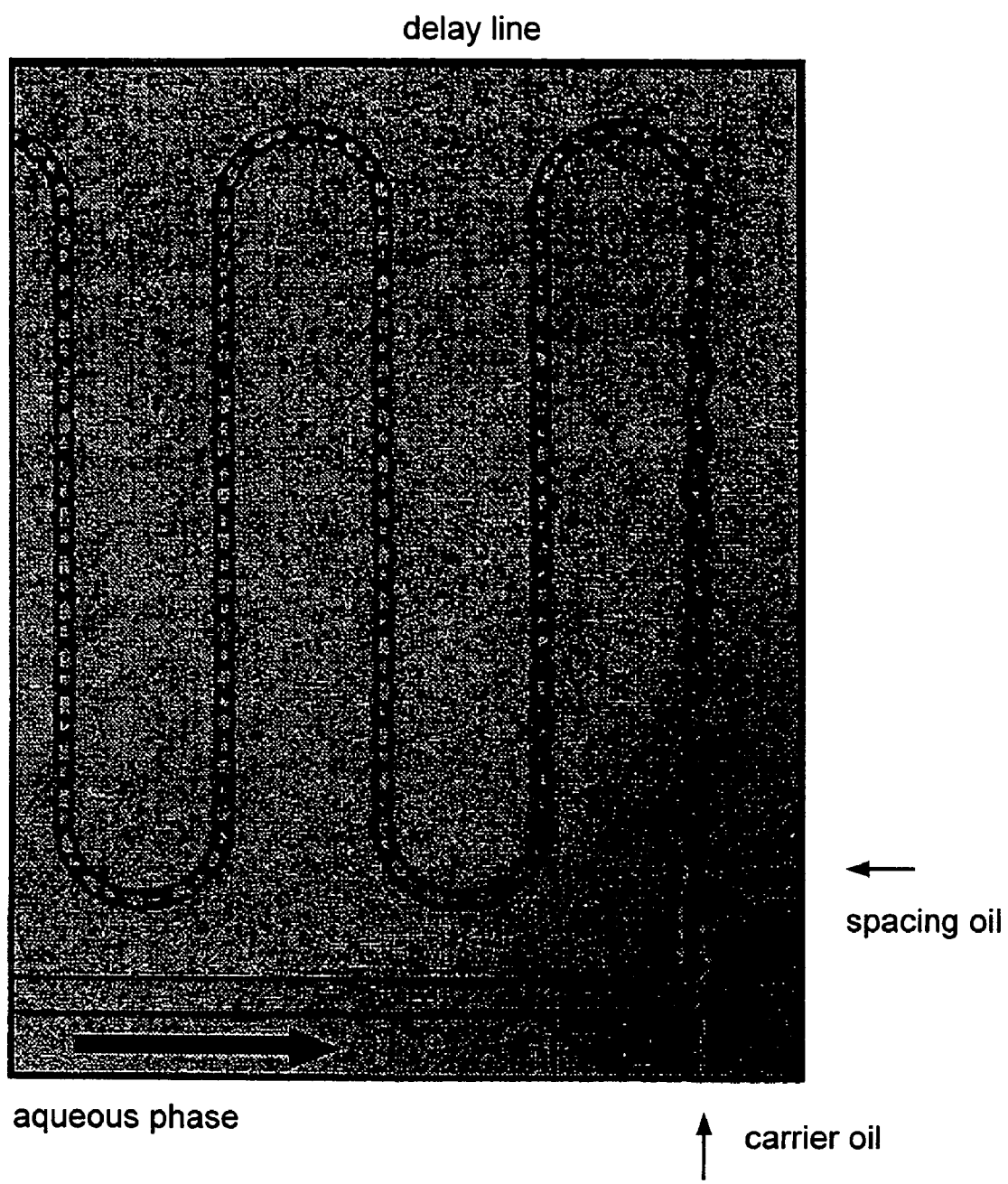
FIG. 21 Time delay reaction module. (A) Droplets of perfluorodecaline alternate with aqueous droplets in a hexadecane carrier fluid. The 'single-file' ordering of the droplets provides for long delays with essentially no deviation in the precise spacing of aqueous droplets or droplet order. (B) Increasing the width and height of the channel to create a 'large cross-sectional area' channel provides for extremely long time delays from minutes to hours. The exact ordering and spacing between the droplets is not maintained in this type of delay line.

Droplet reactor/time delay module: A delay line is used to provide a fixed time for a reaction. Two non-limiting examples of how this can be achieved are 'single file' and 'large cross-section' channels. The 'single file' delay line uses length to achieve a fixed reaction time. As this often results in exceptionally long channels, it is desirable to place spacer droplets of a third fluid, immiscible with both the carrier oil and the aqueous droplets inbetween aqueous droplet pairs. There is then an alternation between aqueous and non-aqueous droplets in a carrier oil. This is shown in FIG. 21A. A second possibility for achieving a long time delay is to use wide and deap channel having a 'large cross-sectiononal area' to slow the average velocity of the droplets. An example of this is shown in FIG. 21B.

Figure 22A:
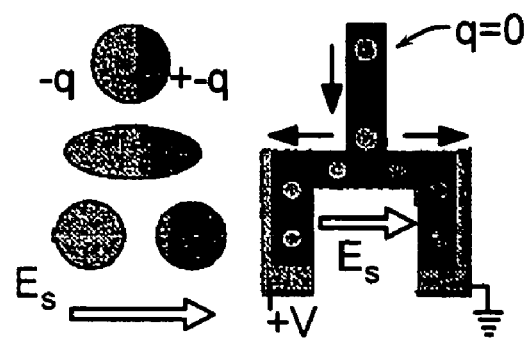
FIG. 22 Recharging neutral drops. (A) Schematic to recharge neutral drops by breaking them in the presence of an electric field. Uncharged drops (q=0) are polarized in an electric field ($E_S \neq 0$), and provided $E_S$ is sufficiently large, as shown in the photomicrograph of (B), they break into two oppositely charged daughter drops in the extensional flow at a bifurcation. The enlargement of the dashed rectangle, shown in (C), reveals that the charged drops are stretched in the electric field ES but return to spherical on contacting the electrodes indicated by dashed vertical lines.
Figure 22B:
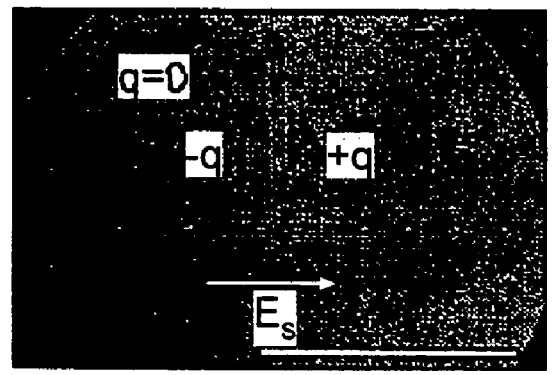
Figure 22C:

Recharging module: The use of oppositely charged droplets and an electric field to combine and mix reagents is extremely robust, and 100% of the droplets coalesce with their partner from the opposite stream. However, after they coalesce the resultant drops carry no electrostatic charge. While it is convenient to charge droplets during formation, other methods must be employed in any robust droplet-based microfluidic system to recharge the mixed droplets if necessary for further processing. This is readily accomplished through the use of extensional flow to split neutral droplets in the presence of an electric field which polarizes them, resulting in two oppositely charged daughter droplets; this is sketched in FIG. 22A. The photomicrograph in FIG. 22B shows neutral droplets entering a bifurcation and splitting into charged daughter droplets. The dashed region in FIG. 22B is enlarged in FIG. 22C to illustrate the asymmetric stretching of the charged droplets in the electric field. The vertical dashed lines indicate the edges of the electrodes where the droplets return to their symmetric spherical shape. The electric field also allows precision control of the droplet splitting providing the basis for a robust droplet division module which allows the splitting of the contents into two or more aliquots of identical reagent, facilitating multiple assays on the contents of the same microreactor.

Figure 23:
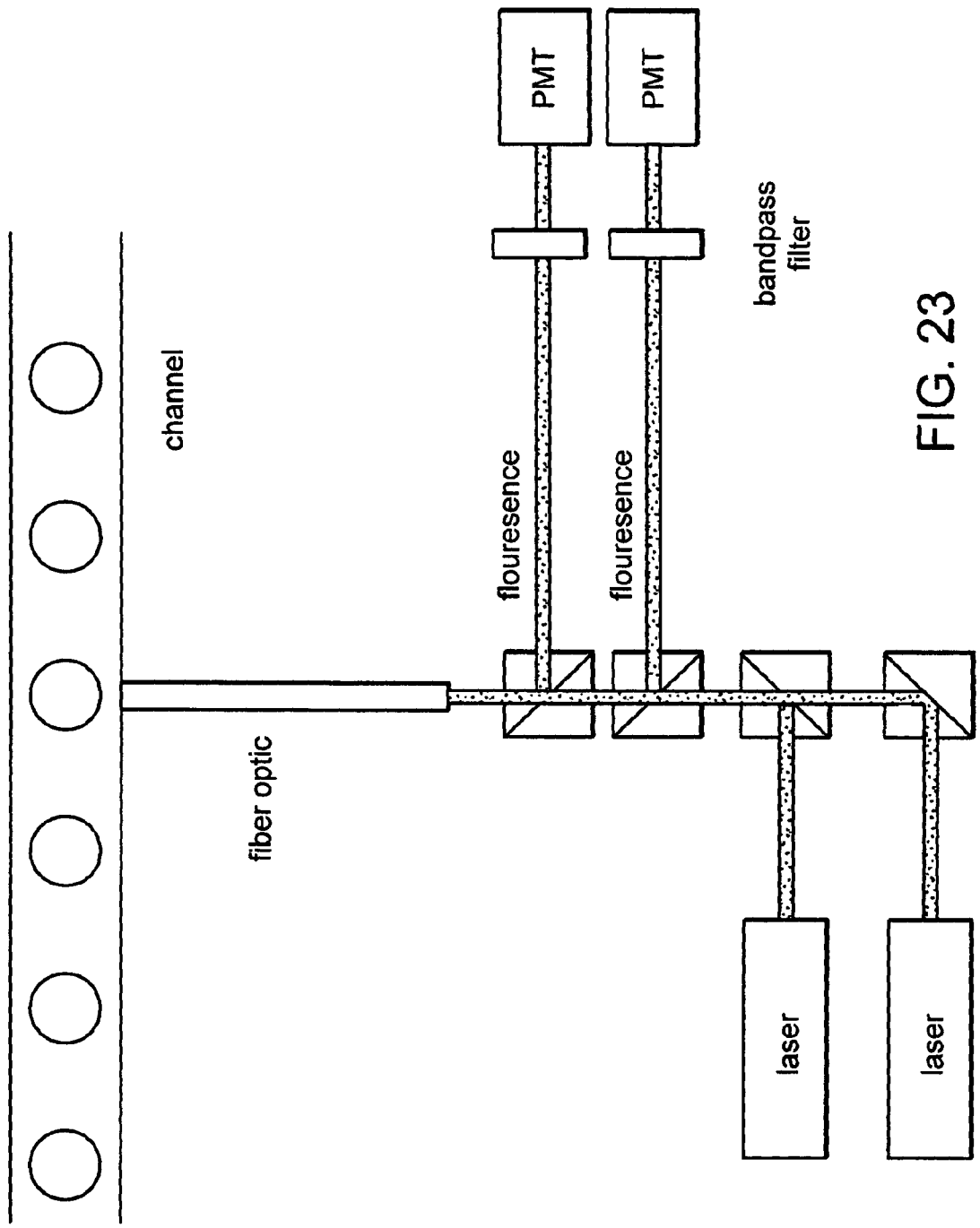
FIG. 23 Detection module. One or more lasers are coupled to an optical fibre that is used to excite the fluorescence in each droplet as it passes over the fibre. The fluorescence is collected by the same fibre and dichroic beam splitters separate off specific wavelengths of the fluorescent light and the intensity of the fluorescence is measured with a photomultiplier tube (PMT) after the light passes through a band-pass filter.

Detection module: The detection module consists of an optical fiber, one or more laser, one or more dichroic beam splitter, bandpass filters, and one or more photo multiplying tube (PMT) as sketched in FIG. 23.

Figure 24A:
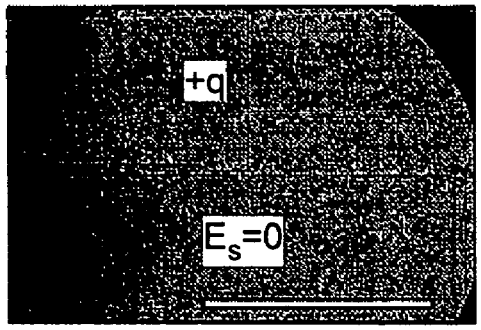
FIG. 24 Manipulating charged drops. In (A) charged drops alternately enter the right and left channels when there is no field applied ($E_S=0$). The sketch in (B) shows the layout for using an electric field $E_S$ to select the channel charged drops will enter at a bifurcation. When an electric field is applied to the right (C), the drops enter the right branch at the bifurcation; they enter the left branch when the field is reversed (D). After the bifurcation, the distance between drops is reduced to half what it was before indicating the oil stream is evenly divided. The inset of (D) shows the deformation in the shape of a highly charged drop in an electric field.
Figure 24B:
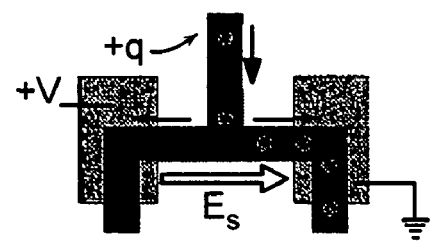
Figure 24C:
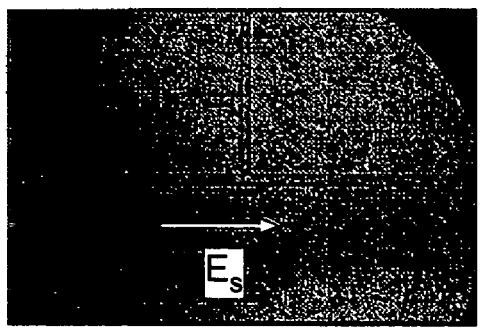
Figure 24D:
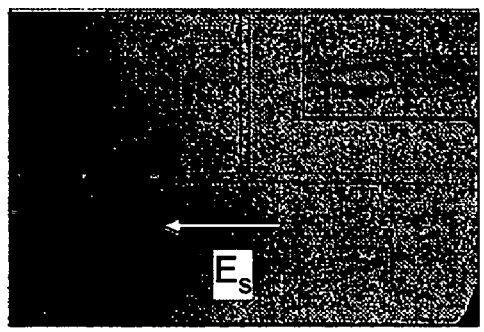

Sorting module: The contents of individual droplets must be probed, and selected droplets sorted into discreet streams. The use of electrostatic charging of droplets provides a means for sorting that can be precisely controlled, can be switched at high frequencies, and requires no moving parts. Electrostatic charge on the droplets enables drop-by-drop sorting based on the linear coupling of charge to an external electric field. As an example, a T-junction bifurcation that splits the flow of carrier fluid equally will also randomly split the droplet population equally into the two streams, as shown in FIG. 24A. However, a small electric field applied at the bifurcation precisely dictates which channel the drops enter; a schematic of the electrode configuration is shown in FIG. 24B. Varying the direction of the field varies the direction of the sorted droplets as shown in FIGS. 24C and 24D. The large forces that can be imparted on the droplets and the high switching frequency make this a fast and robust sorting engine with no moving parts; thus the processing rate is limited only by the rate of droplet generation.

Example 2

Enrichment of lacZ Genes from a Pool of Mutant lacZ Genes Based on □-Galactosidase Activity Inside Aqueous Droplets in a Microfluidic Device An example is given how single genes encoding enzymes with a desired activity can be selected from a pool of genes by making and manipulating aqueous droplets using the microfluidic device described in Example 1. It is demonstrated that lacZ genes encoding for active β-galactosidase enzyme can be selected from a pool of mutant lacZ genes by: (1) forming droplets containing (a) a coupled in vitro transcription/translation system and (b) genes; (2) fusing droplets (a) and (b) to initiate translation with the concentration of genes such that the majority of combined droplets (c) contain no more than one gene per droplet; (3) passing the combined droplets (c) down a microfluidic channel to allow translation; (4) fusing each droplet (c) with a droplet (d) which contains an inhibitor of translation (puromycin) and the fluorogenic substrate, fluorescein digalactoside (FDG); (5) passing the combined droplets (e) down a microfluidic channel to allow catalysis and; (6) monitoring the fluorescence of the droplets. When the gene present in the aqueous droplet encodes for an active □-galactosidase enzyme, FDG inside the compartment will be converted into the fluorescent product fluorescein (excitation 488 nm, emission 514 nm). After a single round of selection, lacZ genes can be enriched from a mixture of genes by over 100-fold.

DNA Preparation

The lacZ gene encoding for β-galactosidase is amplified from genomic DNA isolated from strain BL21 of *Escherichia coli* using primers GALBA and GALFO (GALBA: 5'-CAGACTGCACCATGG CCATGATTACGGATTCACTGGCCGTCGTTTTAC-3'; SEQ ID NO: 1; GALFO: 5'-ACGATGTCAGGATCCTTATTATTTTTGAC ACCAGACCAACTGGTAATGGTAG-3'; SEQ ID NO: 2) The PCR product is digested with restriction endonucleases NcoI and BamHI (New England Biolabs Inc., Beverly, Mass., USA). Digested DNA is gel purified and ligated into vector pIVEX2.2b (Roche Biochemicals GmbH, Mannheim, Germany) that is digested with the same enzymes. The ligation product is transformed into XL-10 gold cells (Stratagene). Minicultures are grown from 5 single colonies in 3 ml LB medium supplemented with 100 μg/ml ampicillin at 37° C. over night. From these overnight cultures, plasmid DNA (pDNA) is isolated and sequenced for the presence of the right insert. Linear DNA constructs are generated by PCR using pDNA from a sequenced clone (containing the correct lacZ sequence) as template and primers LMB2-10E (5'-GATGGCGCCCAACAGTCC-3'; SEQ ID NO: 3) and PIVB-4 (5'-TTTGGCCGCCGCCCAGT-3': SEQ ID NO:4).

Full-length mutant lacZ (lacZmut), which has an internal frameshift and hence does not encode an active β-galactosidase, is obtained by cutting pIVEX2.2b-LacZ with restriction enzyme SacI (NEB). Digested DNA is blunted by incubation for 15 min at 12° C. with T4 DNA polymerase (2 U) and dNTPs (500 μM final concentration). The reaction is quenched by adding EDTA to a final concentration of 10 mM and heating to 75° C. for 20 minutes. Blunted DNA is purified and self-ligated with T4 DNA ligase (1 Weiss unit) in the presence of 5% PEG 4,000 by incubating for 2 hrs at 22° C. pDNA is directly transformed into XL-10 Gold cells. Minicultures are grown from 5 single colonies in 3 ml LB medium supplemented with 100 μg/ml ampicillin at 37° C. over night and plasmid DNA is isolated. pDNA is digested with SacI and one of the clones lacking the internal SacI site is used to generate linear DNA constructs as described above.

In Vitro Transcription and Translation Inside Aqueous Droplets in a Microfluidic System LacZ and lacZmut linear DNA constructs are mixed at a molar ratio of 1:5, 1:100 and 1:1000, respectively in nuclease-free water.

A commercial in vitro translation system (EcoProT7, Novagen/EMD biosciences Ltd, Madison, Wis., USA) is used according to the manufacturer's protocol. Using the device described in Example 1, EcoProT7 extract is compartmentalised into droplets (a) of mean 10 μm diameter (520 fl volume). Droplets (b), of mean 7.4 μm diameter (220 fl volume) are formed containing 0.67 mM L-methionine and 0.25 mM 7-hydroxycoumarin-3-carboxylic acid (Sigma Aldrich) (excitation 386 μm, emission 448 nm), and 0.75 pM DNA (mixes of LacZ and lacZmut linear DNA at the ratios described above) in nuclease-free water. The droplets are formed in a carrier fluid consisting of perfluorinated oil; the perfluorinated oil can either consist of the mixture described in example 1 or alternatively one of the 3M™ Fluorinert™ liquids. Each droplet (a) is fused with a droplet (b). The concentration of DNA is such that the majority of combined droplets (c) contain no more than one gene per droplet (the mean number of genes per droplet=0.1). According to the Poisson Distribution, $P(a)=e^{-m}[m^a/a!]$, where m=0.1=the mean number of genes per droplet, and P(a)=the probability of finding a genes per droplet, 90.5% of droplets contain no genes, 9.05% contain 1 gene, and 0.45% contain 2 genes and 0.016% contain more than two genes). The combined droplets (c) are passed down the microfluidic channel held at 30° C. for 30 minutes to allow in vitro transcription and translation.

Screening and Selection for □-Galactosidase Activity

After the translation step, a series of droplets (d) of 11.2 μm diameter (740 fl volume, equal in volume to droplets (c)) and which contain 4 mM puromycin (to stop translation) and 1 mM FDG (Molecular Probes) in water. Each droplet (c) is fused with a droplet (d) to stop translation and start the catalytic reaction. The combined droplets (e) are passed down the microfluidic channel held at 30° C. for 10 minutes to allow catalysis. The fluorescence of the droplets is monitored. All droplets contain 7-hydroxycoumarin-3-carboxylic acid allowing their identification. Monitoring of the flourescence signal from individual droplets is achieved by coupling both excitation and fluorescent signals to the droplets through an optical fiber. The continuous wave emission from two diode lasers (363 nm and 488 nm) is used for excitation dichroic beam splitters and band pass filters (450±20 nm and 530±20 μm) are used to isolate the fluorescent emission to detect the 7-hydroxycoumarin-3-carboxylic acid fluorescence and the fluorescein fluorescence as measured with photomultiplying tubes. Droplets with the highest fluorescein fluorescence (with a sorting gate set such that less than 0.05% of the population of droplets from a negative control without DNA) are sorted. For each sort, 10,000 droplets are collected.

DNA Recovery from Sorted Droplets

DNA from the sorted droplets is precipitated by adding 100 μl 0.3 M sodium acetate pH 5.2 and 70 μl isopropanol in the presence of 20 μg glycogen as carrier (Roche Biochemicals GmbH, Mannheim, Germany). DNA is pelleted by centrifugation at 20,000×g for 15 min at 4° C. Precipitated DNA is ished twice with 100 μl 70% ethanol and the DNA pellet is dried using a Speedvac (Eppendorf). DNA is resuspended into 10 μl nuclease-free water.

PCR Amplification of Recovered DNA

PCR reactions are set up at 50 μl total volume, using Expand Long Template PCR mix with buffer 1 according to the manufacturer's protocol (Roche). Primers LMB2-11E (5'-GCCCGATCTTCCCCATCGG-3'; SEQ ID NO: 5) and PIVB-8 (5'-CACACCCGTCCTGTGGA-3'; SEQ ID NO: 6) are used at a concentration of 300 μM each. Reactions are incubated for 2 min at 94° C. and subsequently subjected to 10 cycles at 94° C., 15 s; 55° C., 30 s; 68° C., 2 min, another 22 cycles with an increment in elogation time of 10 s/cycle and a final incubation step for 7 min at 68° C. PCR products are purified using a Wizard PCR prep kit (Promega).

SacI Digestion of PCR Products

To be able to distinguish between lacZ DNA and lacZmut DNA, purified PCR products are digested with 20 U of SacI enzyme. SacI cuts the lacZ gene but not lacZmut. SacI enzyme is heat-inactivated (15 min at 65° C.) and 5 μl of digested DNA is loaded onto a 1% agarose gel in TAE. DNA is electrophoresed at 5V/cm. DNA is visualized by staining with ethidium bromide and quantified using ImageQuant TL gel analysis software (Amersham Biosciences).

Genes encoding an active β-galactosidase (lacZ genes) are significantly enriched from a pool of mutant genes (lacZmut genes) encoding an inactive β-galactosidase with all ratios of lacZ:lacZmut tested. With an initial gene concentration of 0.1% lacZ genes, the lacZ genes could be enriched over 100-fold in a single round of selection.

Example 3

Mutants with Improved β-Galactosidase Activity can be Selected from a Random Mutagenesis Library of Eevolved β-Galactosidase (Ebg) Using Compartmentalisation of Genes in Aqueous Droplets in a Microfluidic Device The gene encoding for evolved-β-galactosidase (Ebg) is often used as a model to study the evolution of novel enzyme functions within an organism. The wild type ebgA gene of *Escherichia coli* encodes an enzyme with feeble β-galactosidase activity, but ebgA has the potential to evolve sufficient activity to replace the lacZ gene for growth on the sugars lactose and lactulose. Genetic analysis of these mutants has revealed that only two amino acid replacements account for the drastic increase in β-galactosidase activity.

Here we show that similar mutants can be obtained in vitro by creating a random mutagenesis library of the ebg gene and subjecting them to selection for β-galactosidase activity by making and manipulating aqueous droplets using the microfluidic device described in Example 1.

Error Prone Mutagenesis of EbgAC Using Base Analogues

A gene segment encoding for the A domain and the C domain of evolved β-galactosidase enzyme is amplified from genomic DNA of *E. coli* strain BL21 using primers EbgACFw (5'-CAGACTGCACCGCGGGATGAATCGC TGGGAAAACATTCAGC -3'; SEQ ID NO: 7) and EbgACBw (5'-GCGAGG AGCTCTTATTTGTTATG-GAAATAACCATCTTCG-3'; SEQ ID NO: 8). The PCR product is cloned into vector pIVEX2.2b using restriction endonucleases SacII and SacI (NEB). DNA is transfected into XL10-gold cells and single colonies are screened for the presence of the EbgAC gene construct with the right nucleotide sequence. pDNA from a single clone with the right EbgAC gene sequence is used as template to generate a random mutagenesis library using nucleoside analogues essentially as described by Zaccolo et al. (J Mol Biol 255(4): 589-603, 1996). A mixture of the 5'-triphosphates of 6-(2-deoxy-b-D-ribofuranosyl)-3,4-dihydro-8H-pyrimido-[4,5-C][1,2]oxazin-7-one (dPTP) and of 8-oxo-2'deoxyguanosine (8-oxodG) is prepared in PCR grade water at 2 mM and 10 mM concentrations, respectively. This base analogue mix is diluted 167× and 333× in expand long template PCR buffer 1 (Roche), containing $MgCl_2$ (2 mM), dNTPs (500 μM), expand long template PCR polymerase enzyme mix (Roche), primer LMB2-9E (5'-GCATTTATCAGGGTTATTGTC-3; SEQ ID NO: 9; 500 nM') and triple biotinylated primer PIVB-1 (5'-3Bi-GCGTTGATGCAATTTCT-3'; SEQ ID NO: 10; 500 nM) in a total reaction volume of 50 µl. Five nanograms of pIVEX2.2b-EbgAC DNA is added and samples are subjected to 1 cycle of 2 minutes at 94° C., followed by 3 cycles at 94° C., 1 min; at 50° C., 1 min; at 68° C., 4 min), followed by a final extension of 7 min at 68° C. Ten micrograms of molecular biology-grade glycogen is added to the DNA prior to purification using a Qiaquick PCR purification kit. After purification DNA is recovered in 50 µl PCR-grade water. Ten micrograms of Streptavidin-coated magnetic beads (Dynabeads M-280 streptavidin, Dynal Biotech, Oslo, Norway) are rinsed in 2× binding buffer provided with the beads, resuspended into 50 µl 2× binding buffer and added to the purified DNA. Beads and DNA are incubated for 2.5 hrs at room temperature in a rotating device. Beads are collected with a magnet and rinsed twice with ish buffer that is provided with the beads and twice with PCR-grade water. Finally, beads are resuspended into 25 µl water. 5 µl of bead-bound DNA is used as template in a second PCR reaction (25 cycles of 15 s at 94° C., 30s at 55° C. and 2 min at 68° C.). PCR product is purified using a Qiaquick PCR purification kit and recovered in 50 µl of PCR-grade water.

Iterative Rounds of In Vitro Selection Using a Microfluidic System

The generated random mutagenesis library of ebgAC is subjected to 2 successive rounds of selection. Each selection round consisted of 7 separate steps: (1) forming droplets containing (a) a coupled in vitro transcription/translation system and (b) genes; (2) fusing droplets (a) and (b) to initiate translation with the concentration of genes such that the majority of combined droplets (c) contain no more than one gene per droplet; (3) passing the combined droplets (c) down a microfluidic channel to allow translation; (4) fusing each droplet (c) with a droplet (d) which contains an inhibitor of translation (puromycin) and the fluorogenic substrate, fluorescein digalactoside (FDG); (5) passing the combined droplets (e) down a microfluidic channel to allow catalysis; (6) monitoring the fluorescence of the droplets. When the gene present in the aqueous droplet encodes for an active β-galactosidase enzyme, FDG inside the compartment will be converted into the fluorescent product fluorescein (excitation 488 nm, emission 514 nm) and; (7) recovery and amplification of genes from the selected double emulsion droplets. The entire procedure is described in detail above (Example 2). Sets of nested primers are used for subsequent selection rounds (Table 1).

After each selection round, the number of positive droplets within the Ebg library increased by at least 10-fold.

Characterisation of the β-Galactosidase Activity of Single Members of the Ebg Library After the $2^{nd}$ selection round, DNA is recovered from the double emulsions by standard isopropanol precipitation and PCR amplified using primers LMB2-11 and PIVB-11. Amplified DNA is digested with restriction endonucleases SacI and SacII and cloned into pIVEX2.2b that is digested with the same enzymes. The ligation product is transformed into ElectroBlue electrocompetent cells (Strategene) by electroporation (at 17 kV/cm, 600 Ω, 25 µF) and plated onto LB agar plates with ampicillin. Ebg gene constructs are amplified from single colonies by colony PCR using primers LMB2-10E and PIVB-4. One microliter of PCR product is added to 14 µl of IVT mix (Novagen's EcoProT7 extract, supplemented with 200 µM L-methionine) and incubated for 90 min at 30° C. Forty microliters substrate solution (250 µM FDG, 10 mM $MgCl_2$, 50 mM NaCl, 1 mM DTT and 100 µg/ml BSA in 10 mM Tris-HCl, pH 7.9) is added and the conversion of FDG into fluorescein is monitored every 45 s for 90 min at 37° C.

The screened clones show a broad variety of β-galactosidase activities. ~50% of colonies have β-galactosidase activities that are comparable to or lower than wild type Ebg. ~12.5% of clones show β-galactosidase activity that is comparable to the Class I and Class II mutants (single point mutations) described by Hall et al. (*FEMS Microbiol Lett* 174(1): 1-8, 1999; *Genetica* 118(2-3): 143-56, 2003). In conclusion, the system described here can be used for the selection of ebg variants with improved β-galactosidase activity from a large gene library.

REFERENCES

Anderson, C. W., Straus, J. W. and Dudock, B. S. (1983) Methods Enzymol, 101, 635-44.

Anderson, J. E. (1993) Curr. Op. Struct. Biol., 3, 24-30. Ash, M. and Ash, I. (1993) *H*andbook of industrial surfactants. Gower, Aldershot.

Atwell, S. & Wells, J. A. (1999). *Proc. Natl. Acad. Sci. USA* 96, 9497-9502.

Baccanari, D. P., Averett, D., Briggs, C. and Burchall, J. (1977) Biochemistry, 16, 3566-72. Barany, F. (1991) PCR Methods Applic., 1, 5-16.

Baez. S., Segura-Aguilar, J., Widersten, M., Johansson, A.-S. & Mannervik, B. (1997) *Biochem. J.* 324, 25-28.

TABLE 1 list of primers used to amplify recovered DNA from successive rounds of selection

| Selection round | Forward primer | Backward primer |
|---|---|---|
| 0 | LMB2-9E<br>5'-GCATTTATCAGGGTTATTGTC-3'<br>SEQ ID NO: 9 | PIVB-1<br>5'-GCGTTGATGCAATTTCT-3'<br>SEQ ID NO: 10 |
| 1 | LMB2-10E<br>5'-GATGGCGCCCAACAGTCC-3'<br>SEQ ID NO: 3 | PIVB-4<br>5'-TTTGGCCGCCGCCCAGT-3'<br>SEQ ID NO: 4 |
| 2 | LMB2-11<br>5'-ATGCGTCCGGCGTAGAGG-3'<br>SEQ ID NO: 11 | PIVB-11<br>5'-AGCAGCCAACTCAGCTTCC-3'<br>SEQ ID NO: 12 |

Bass, S., Greene, R. and Wells, J. A. (1990) Proteins, 8, 309-14.

Becher, P. (1957) Emulsions: theory and practice. Reinhold, N.Y. Benita, S., Ed. (1996). Microencapsulation: methods and industrial applications. Drugs and pharmaceutical sciences. Edited by Swarbrick, J. New York: Marcel Dekker.

Benner, S. A. (1994) Trends Biotechnol, 12, 158-63.

Berman, J., Eisenberg, S. and Tye, B. K. (1987) Methods Enzymol, 155, 528-37.

Betlach, L., Hershfield, V., Chow, L., Brown, W., Goodman, H. M. & Boyer, H. W. (1976). A restriction endonuclease analysis of the bacterial plasmid controlling the EcoRI restriction and modification of DNA. *Federation Proceedings* 35, 2037-2043.

Blattner, F. R. and Dahlberg, J. E. (1972) Nature New Biol, 237, 227-32.

Bougueleret, L., Schwarzstein, M., Tsugita, A. & Zabeau, M. (1984). Characterization of the genes coding for the Eco RV restriction and modification system of *Escherichia coli*. *Nucleic Acids Res* 12(8), 3659-76.

Bru, R. & Walde, P. (1991). Product inhibition of alpha-chymotrypsin in reverse micelles. *Eur J Biochem* 199(1), 95-103. Bru, R. & Walde, P. (1993). Catalytic activity of elastase in reverse micelles. *Biochem Mol Biol Int* 31(4), 685-92.

Brynes, P. J., Andrade, P. & Gordon D. (1982). Sensitive fluorogenic substrates for the detection of trypsin-like proteases and pancreatic elastase. *Anal. Biochem.* 126, 447.

Cahill, P., Foster, K. and Mahan, D. E. (1991) Clin Chem, 37, 1482-5.

Chakrabarti, A. C., Breaker, R. R., Joyce, G. F. & Deamer, D. W. (1994). Production of RNA by a polymerase protein encapsulated within phospholipid vesicles. *J Mol Evol* 39(6), 555-9.

Chamberlin, M. and Ring, J. (1973) J Biol Chem, 248, 2235-2244.

Chang, T. M. (1987). Recycling of NAD(P) by multienzyme systems immobilized by microencapsulation in artificial cells. *Methods Enzymol* 136(67), 67-82.

Chang, T. M. S. (1992). Recent advances in artificial cells based on microencapsulation. In *Microcapsules and nanoparticles in medicine and pharmacy* (Donbrow, M., ed.), pp. 323-339. CRC Press, Boca Raton, Fla.

Chapman, K. B. and Szostak, J. W. (1994) Curr. op. Struct. Biol., 4, 618-622.

Chetverin, A. B. and Spirin, A. S. (1995) Prog Nucleic Acid Res Mol Biol, 51, 225-70.

Clackson, T. and Wells, J. A. (1994) Trends Biotechnol, 12, 173-84.

Cormack, B. P., Valdivia, R. H. & Falkow, S. (1996). FACS-optimized mutants of the green fluorescent protein (GFP). *Gene*(33).

Craig, D. et al. (1995). Fluorescence-based enzymatic assay by capillary electrophoresis laser-induced fluorescence detection for the determination of a few □-galactosidase molecules. *Anal. Biochem.* 226, 147.

Creagh, A. L., Prausnitz, J. M. & Blanch, H. W. (1993). Structural and catalytic properties of enzymes in reverse micelles. *Enzyme Microb Technol* 15(5), 383-92.

Cull, M. G., Miller, J. F. and Schatz, P. J. (1992) Proc Natl Acad Sci USA, 89, 1865-9.

Delagrave, S., Hawtin, R. E., Silva, C. M., Yang, M. M. & Youvan, D. C. (1995). Red-shifted excitation mutants of the green fluorescent protein. *Biotechnology NY* 13(2), 151-4.

Demartis, S., Huber, A., Viti, F., Lozzi, L., Giovannoni, L., Neri, P., Winter, G. & Neri, D. (1999). *J. Mol. Biol.* 286, 617-633.

Dickinson, E. (1994) In Wedlock, D. J. (ed.), Emulsions and droplet size control. Butterworth-Heinemann, Oxford, Vol. pp. 191-257.

Ehrig, T., O'Kane, D. J. & Prendergast, F. G. (1995). Green-fluorescent protein mutants with altered fluorescence excitation spectra. *Febs Lett* 367(2), 163-6.

Ellington, A. D. and Szostak, J. W. (1990) Nature, 346, 81822.

Ellman, J., Mendel, D., Anthony, C. S., Noren, C. J. and Schultz, P. G. (1991) Methods Enzymol, 202, 301-36.

Fahy, E., Kwoh, D. Y. and Gingeras, T. R. (1991) PCR Methods Appl, 1, 25-33.

Fields, S. & Song, O. (1989) A novel genetic system to detect protein-protein interactions. *Nature* 340, 245-6.

Finch, C. A. (1993). Encapsulation and controlled release. *Spec. Publ.-R. Soc. Chem.* 138, 35.

Fisch, I., Kontermann, R. E., Finnern, R., Hartley, O., Soler, G. A., Griffiths, A. D. and Winter, G. (1996) Proc Natl Acad Sci USA, 93, 7761-6.

Fomusek, L. and Vetvicka, V. (1986). Polymeric microspheres as diagnostic tools for cell surface marker tracing. *Crit. Rev. Ther. Drug Carrier Syst.* 2, 137-74

Freese, E. (1959) J. Mol. Biol., 1, 87.

Friedberg, E. C., Walker, G. C. and Siede, W. (1995) DNA repair and mutagenesis. ASM Press, Washington D.C.

Gold, L., Polisky, B., Uhlenbeck, O. and Yarus, M. (1995) Annu Rev Biochem, 64, 763-97.

Green, R. and Szostak, J. W. (1992) Science, 258, 1910-5.

Gregoriadis, G. (1976) Methods Enzymol, 44, 21 8-27.

Griffiths, A. D., Williams, S. C., Hartley, O., Tomlinson, I. M., Waterhouse, P., Crosby, W. L., Kontermann, R. E., Jones, P. T., Low, N. M., Allison, T. J. and et a.l. (1994) Embo *J*, 13, 3245-60.

Guixe, V., Rodriguez, P. H. & Babul, J. (1998). Ligand-induced conformational transitions in *Escherichia coli* phosphofructokinase 2. *Biochemistry* 37, 13269-75.

Haber, J., Maslakiewicz, P., Rodakiewicz, N. J. & Walde, P. (1993). Activity and spectroscopic properties of bovine liver catalase in sodium bis(2-ethylhexyl)sulfosuccinate/isooctane reverse micelles. *Eur J Biochem* 217(2), 567-73.

Habig, W. H. & Jakoby, W. B. (1981). *Methods in Enzymology,* 77, 398-405.

Hanes, J. & Pluckthun, A. (1997). In vitro selection and evolution of functional proteins by using ribosome display. *Proc. Natl. Acad. Sci. USA* 94, 4937-4942.

Haugland, R. H. (ed.). (1996). Handbook of Fluorescent Probes and Research Chemicals, Sixth Edition, Molecular Probes, pp 201-250.

Heim, R. & Tsien, R. Y. (1996). Engineering green fluorescent protein for improved brightness, longer wavelengths and fluorescence resonance energy transfer. *Curr Biol* 6(2), 178-82.

Hermanson, G. T. (1996) Bioconjugate techniques. Academic Press, San Diego.

Hochuli, E., Dobeli, H. and Schacher, A. (1987) J Chromatogr, 411, 177-84.

Hong, S.-B. & Raushel, F. M. (1999). *Biochemistry,* 38, 1159-1165.

Hoogenboom, H. R. (1997). Designing and optimizing library selection strategies for generating high-affinity antibodies. *Trends Biotechnol.* 15, 62-70.

Hoogenboom, H. R., et al., (1991) Nucl. Acids Res., 91, 4133-4137.

Huang, Z. et al. (1992). A sensitive competitive ELISA for 2,4-dinitrophenol using 3,6-fluorescein diphosphate as a fluorogenic substrate. *J. Immunol. Meth.* 149, 261.

Janda, K. D., Lo, L.-C., Lo, C.-H. L., Sim, M., -M., Wang, R., Wong, C.-H. and Lerner, R. A. (1997) Science, 275, 945-948.

Jestin, J.-L., Kristensen, P. & Winter, G. (1999). *Angew. Chem. Int. Ed. Engl.* 38, 1124-1127.

Johannsson, A. (1991) In Price, C. P. and Newman, D. J. (ed.), Heterogeneous enzyme immunoassays. Stockton Press, New York, Vol. pp. 295-325.

Johannsson, A. and Bates, D. L. (1988) In Kemeny, D. M. and Challacombe, S. i. (ed.) Amplification by second enzymes. John Wiley, Chichester, Vol. pp. 85-106.

Jones, L. J. et al. (1997). Quenched BODIPY dye-labeled casein substrates for the assay of protease activity by direct fluorescence measurement. *Anal. Biochem.* 251, 144.

Joyce, G. F. (1994) *Curr. op. Structural Biol.,* 4, 331-336.

Kadir, F. H. and Moore, G. R. (1990) *Febs Lett,* 276, 81-4.

Kallen, R. G. & Jencks, W. P. (1966). The mechanism of the condensation of formaldehyde with tetrahydrofolic acid. *J. Biol. Chem.* 241, 5851-5863.

Katanaev, V. L., Kurnasov, O. V. and Spirin, A. S. (1995) Febs Lett, 359, 89-92.

Keij, J. F., Groenewegen, A. C. & Visser, J. W. M. (1994) High-speed photodamage cell sorting: An evaluation of the ZAPPER prototype. *Methods in cell biology* 42, 371-358.

Kerker, M. (1983) Elastic and inelastic light scattering in flow cytometry. *Cytometry* 4, 1-10

Klug, A. (1995) Ann NY Acad Sci, 758, 143-60.

Klug, A. and Schwabe, J. W. (1995) Faseb T, 9, 597-604.

Kolb, V. A., Makeyev, E. V., Kommer, A. and Spirin, A. S. (1995) Biochem Cell Biol, 73, 1217-20.

Kowalczykowski, S. C., Dixon, D. A., Eggleston, A. K., Lauder, S. D. and Rehrauer, W. M. (1994) Microbiol Rev, 58, 401-65.

Krumdiek, C. L. & Baugh, C. M. (1980) Solid-phase synthesis of pteroylpolyglutamates. Methods Enzymol. pp. 524-529

Kumar, A., Kumar, A. & Katiyar, S. S. (1989). Activity and kinetic characteristics of glutathione reductase in vitro in reverse micellar waterpool. *Biochim Biophys Acta* 996(1-2), 1-6.

Landegren, U., Kaiser, R., Sanders, J. and Hood, L. (1988) Science, 241, 1077-80.

Lesley, S. A., Brow, M. A. & Burgess, R. R. (1991). Use of in vitro protein synthesis from polymerase chain reaction-generated templates to study interaction of *Escherichia coli* transcription factors with core RNA polymerase and for epitope mapping of monoclonal antibodies. *J Biol Chem* 266(4), 2632-8.

Lesley, S. A. (1995) Methods Mol Biol, 37, 265-78.

Leung, D. W., Chen, E. and Goeddel, D. V. (1989) Technique, 1, 11-15.

Liao, H., McKenzie, T. and Hageman, R. (1986) Proc Natl Acad Sci USA, 83, 576-80.

Lim, F. & Sun, A. M. (1980). Microencapsulated islets as bioartificial endocrine pancreas. *Science* 210(4472), 908-10.

Lim, F., Ed. (1984). Biomedical applications of microencapsulation. Boca Raton, Fla.: CRC Press.

Lissant, K. J., ed *Emulsions and emulsion technology*. Surfactant Science New York: Marcel Dekker, 1974.

Lissant, K. J., ed. *Emulsions and emulsion technology*. Surfactant Science New York: Marcel Dekker, 1984.

Lorenz, W. W., McCann, R. O., Longiaru, M. & Cormier, M. J. (1991). Isolation and expression of a cDNA encoding *Renilla reniformis* luciferase. *Proc Natl Acad Sci USA* 88(10), 4438-42.

Low, N. M., Holliger, P. H. and Winter, G. (1996) J Mol Biol, 260, 359-68.

Lowman, H. B., Bass, S. H., Simpson, N. and Wells, J. A. (1991) Biochemistry, 30, 10832-8.

Luisi, P. L. & B., S.-H. (1987). Activity and conformation of enzymes in reverse micellar solutions. *Methods Enzymol* 136(188), 188-216.

Ma, C., Kudlicki, W., Odom, O. W., Kramer, G. and Hardesty, B. (1993) Biochemistry, 32, 7939-45.

Mackenzie, N. M. & Pinder, A. C. (1986). The application of flow microfluorimetry to biomedical research and diagnosis: a review. *Dev. Biol. Stand.* 64, 181-193.

Magdassi, S., Frenkel, M., Carti, N. and Cazan, R. (1984) 97, 377-379.

Mahajan, N. P., Linder, K., Berry, G., Gordon, G. W., Heim, R. & Herman, B. (1998). Bcl-2 and Bax interactions in mitochondria probed with green fluorescent protein and fluorescence resonance energy transfer. *Nat Biotechnol* 16(6), 547-52.

Manley, J. L., Fire, A., Samuels, M. and Sharp, P. A. (1983) Methods Enzymol. 101, 568-82.

Mao, Q. & Walde, P. (1991). Substrate effects on the enzymatic activity of alpha-chymotrypsin in reverse micelles. *Biochem Biophys Res Commun* 178(3), 1105-12.

Mao, Q., Walde, P. & Luisi, P. L. (1992). Kinetic behaviour of alpha-chymotrypsin in reverse micelles. A stopped-flow study. *Eur J Biochem* 208(1), 165-70.

Masui, R. & Kuramitsu, S. (1998). Probing of DNA-binding sites of *Escherichia coli* RecA protein utilizing 1-anilinonaphthalene-8-sulfonic acid. *Biochemistry* 37, 12133-12143.

Matayoshi, E. D. et al. (1990). Novel fluorogenic substrates for assaying retroviral proteases by resonance energy transfer. *Science* 247, 954.

Mattheakis, L. C., Bhatt, R. R. and Dower, W. J. (1994) Proc Natl Acad Sci USA, 91, 9022-6.

McCafferty, J., Griffiths, A. D., Winter, G. and Chiswell, D. J. (1990) Nature, 348, 552-4.

Melton, D. A., Krieg, P. A., Rebagliati, M. R., Maniatis, T., Zinn, K. and Green, M. R. (1984) Nucleic Acids Res, 12, 703556.

Mendel, D., Cornish, V. W. and Schultz, P. G. (1995) Annu Rev Biophys Biomol Struct, 24, 435-62.

Menger, F. M. & Yamada, K. (1979). *J. Am. Chem. Soc.* 101, 6731-6734.

Miele, E. A., Mills, D. R. and Kramer, F. R. (1983) J Mol Biol, 171, 281-95.

Miroux, B., Walker, J. E. (1996) *Journal of Molecular Biology,* 260, 289-298

Miyawaki, A., Llopis, J., Heim, R., McCaffery, J. M., Adams, J. A., Ikura, M. & Tsien, R. Y. (1997). Fluorescent indicators for Ca2+ based on green fluorescent proteins and calmodulin. *Nature* 388(6645), 882-7.

Mize, P. D., Hoke, R. A., Linn, C. P., Reardon, J. E. and Schulte, T. H. (1989) Anal Biochem, 179, 229-35.

Mock, D. M., Langford, G., DuBois, D., Criscimagna, N. & Horowitz, P. (1985) *Anal. Biochem.* 151, 178-181.

Montigiani, S., Neri, G., Neri, P. and Neri, D. (1996) J Mol Biol, 258, 6-13.

Moore, M. J. (1995) Nature, 374, 766-7.

Mulbry, W. W. & Karns, J. S. (1989) *Journal of Bacteriology,* 171, 6740-6746.

Nemoto, N., Miyamoto-Sato, E., Husimi, Y. and Yanagawa, H. (1997). In vitro virus: Bonding of mRNA bearing puromycin at the 3′-terminal end to the C-terminal end of its encoded protein on the ribosome in vitro. *FEBS Letters* 414, 405-408.

New, R. R. C., Ed. (1990). Liposomes: a practical approach. The practical appraoch series. Edited by Rickwood, D. & Hames, B. D. Oxford: Oxford University Press.

Nissim, A., Hoogenboom, H. R. I Tomlinson, I. M., Flynn, G., Midgley, C., Lane, D. and Winter, G. (1994) Embo J, 13, 692-8.

Norman, S. O. (1980). Flow cytometry. *Med. Phys.* 7, 609-615.

Oberholzer, T., Albrizio, M. & Luisi, P. L. (1995a). Polymerase chain reaction in liposomes. *Chemistry and Biology* 2, 677-682.

Oberholzer, T., Wick, R., Luisi, P. L. & Biebricher, C. K. (1995b). Enzymatic RNA replication in self-reproducing vesicles: an approach to a minimal cell. *Biochem Biophys Res Commun* 207(1), 250-7.

Omburo, G. A., Kuo, J. M., Mullins, L. S. and Raushel, F. M. (1992) *Journal of Biological Chemistry*, 267, 13278-13283.

Parmley, S. F. and Smith, G. P. (1988) Gene, 73, 305-18.

Pederson, H., Holder, S., Sutherlin, D. P., Schwitter, U., King, D. S. & Schultz, P. G. (1998). *Proc. Natl. Acad. Sci. USA* 95, 10523-10528.

Pelham, H. R. and Jackson, R. J. (1976) Eur J Biochem, 67, 247-56.

Perelson, A. S. and Oster, G. F. (1979) J Theor Biol, 81, 64570.

Perez, G. M., Sanchez, F. A. & Garcia, C. F. (1992). Application of active-phase plot to the kinetic analysis of lipoxygenase in reverse micelles. *Biochem J*.

Pirrung & Huang (1996) *Bioconjugate Chemistry*, 7, 317-321.

Posner, B. A., Li, L., Bethell, R., Tsuji, T. and Benkovic, S. J. (1996) Biochemistry, 35, 1653-63.

Qi-X; Grabowski-GA. (1998). Acid beta-glucosidase: intrinsic fluorescence and conformational changes induced by phospholipids and saposin C. *Biochemistry* 37, 11544-115554.

Roberts, B. E., Gorecki, M., Mulligan, R. C., Danna, K. J., Rozenblatt, S. and Rich, A. (1975) Proc Natl Acad Sci USA, 72, 1922-6.

Roberts, J. W. (1969) Nature, 224, 1168-74.

Roberts, R. W. & Szostak, J. W. (1997). RNA-peptide fusions for the in vitro selection of peptides and proteins. *Proc. Natl. Acad. Sci. USA* 94, 12297-12302.

Rolland, J. M., Dimitropoulos, K., Bishop, A., Hocking, G. R. and Nairn R. C. 1985 Fluorescence polarization assay by flow cytometry. *J. Immunol. Methods* 76, 1-10.

Rosenberg, M., Weissman, S. and decrombrugghe, B. (1975) J Biol Chem, 250, 4755-64.

Saiki, R. K., Gelfand, D. H., Stoffel, S., Scharf, S. J., Higuchi, R., Horn, G. T., Mullis, K. B. and Erlich, H. A. (1988) Science, 239, 487-91.

Sambrook, J., Fritsch, E. F. and Maniatis, T. (1989) Molecular cloning: a laboratory manual. Cold Spring Harbor Laboratory Press, New York.

Savage, M. D., Mattson, G., Desai, S., Nielander, G. W., Morgensen, S. and Conklin, E. J. (1994) Avidin-biotin chemistry: a handbook. Pierce Chemical Company, Rockford.

Schick, M. J. (1966) Nonionic surfactants. Marcel Dekker, New York.

Shapiro, H. M. (1983). Multistation multiparameter flow cytometry: a critical review and rationale. *Cytometry* 3, 227-243.

Sherman, P. (1968) Emulsion science. Academic Press, London.

Siemering, K. R., Golbik, R., sever, R. and Haselhof, J. (1996). Mutations that suppress the thermosensitivity of green fluorescent protein. *Current Biology* 6, 1653-1663.

Smith, G. P. (1985) Science, 228, 1315-7.

Soumillion, P., Jaspers, L., Bouchet, M., Marchand, B. J., Winter, G. and Fastrez, J. (1994) J Mol Biol, 237, 415-22.

Stemmer, W. P. (1994a) Nature, 370, 389-91.

Stemmer, W. P. (1994b) Proc Natl Acad Sci USA, 91, 10747-51.

Stofko, H. R., Carr, D. W. and Scott, J. D. (1992) Febs Lett, 302, 274-8.

Sun, A. M., Vasek, I. & Tai, I. (1992). Microencapsulation of living cells and tissues. In *Microencapsulation and nanoparticles in medicine and pharmacy* (Donbrow, M., ed.), pp. 315-322. CRC Press, Boca Raton, Fla.

Sundberg et al. (1995) *J. Am. Chem. Soc.*, 117, 12050-12057.

Tawfik, D. S., Green, B. S., Chap, R., Sela, M. & Eshhar, Z. (1993). catELISA: a facile general route to catalytic antibodies. *Proc Natl Acad Sci USA* 90(2), 373-7.

Tawfik, D. S., Lindner, A. B., Chap, R., Kim, S.-H., Green, B. S. & Eshhar, Z. (1997). In *Immunology Methods Manual*. pp. 553-559, Ed., I. Lefkovits. Academic Press, London.

Tawfik, D. S. & Griffiths, A. D. (1998). Man-made cell-like compartments for molecular evolution. *Nature Biotechnology* 16, 652-656.

Tokatlidis, K., Friguet, B., Deville, B. D., Baleux, F., Fedorov, A. N., Navon, A., Djavadi, O. L. and Goldberg, M. E. (1995) Philos Trans R Soc Lond B Biol Sci, 348, 89-95.

Tripet, B., Yu, L., Bautista, D. L., Wong, W. Y., Irvin, R. T. and Hodges, R. S. (1996) Protein Engng., 9, 1029-1042.

Tuerk, C. and Gold, L. (1990) Science, 249, 505-10.

van Hal, D. A., Bouwstra, J. A. & Junginger, H. E. (1996). Nonionic surfactant vesicles containing estradiol for topical application. In *Microencapsulation: methods and industrial applications* (Benita, S., ed.), pp. 329-347. Marcel Dekker, New York.

Voss, E. W. 1993. Kinetic measurements of molecular interactions by spectrofluorometry. *J. Mol. Recognit.* 6, 51-58.

Walde, P., Goto, A., Monnard, P.-A., Wessicken, M. & Luisi, P. L. (1994). Oparin's reactions revisited: enzymatic synthesis of poly(adenylic acid) in micelles and self-reproducing vesicles. *J. Am. Chem. Soc.* 116, 7541-7547.

Walde, P., Han, D. & Luisi, P. L. (1993). Spectroscopic and kinetic studies of lipases solubilized in reverse micelles. *Biochemistry* 32(15), 4029-34.

Walde, P., Peng, Q., Fadnavis, N. W., Battistel, E. & Luisi, P. L. (1988). Structure and activity of trypsin in reverse micelles. *Eur J Biochem* 173(2), 401-9.

Walker, G. T., Fraiser, M. S., Schram, J. L., Little, M. C., Nadeau, J. G. and Malinowski, D. P. (1992) Nucleic Acids Res, 20, 1691-6.

Wang, G. T. et al. (1990). Design and synthesis of new fluorogenic HIV protease substrates based on resonance energy transfer. *Tetrahedron Lett.* 31, 6493.

Weil, P. A., Luse, D. S., Segall, J. and Roeder, R. G. (1979) Cell, 18, 469-84.

Whateley, T. L. (1996). Microcapsules: preparation by interfacial polymerisation and interfacial complexation and their applications. In *Microencapsulation: methods and industrial applications* (Benita, S., ed.), pp. 349-375. Marcel Dekker, New York.

Wick, R. & Luisi, P. L. (1996). Enzyme-containing liposomes can endogenously produce membrane-constituting lipids. *Chem Biol* 3(4), 277-85.

Widersten, M. and Mannervik,. B. (1995) J Mol Biol, 250, 115-22.

Williams, J. W., Morrison, J. F. and Duggleby, R. G. (1979) Biochemistry, 18, 2567-73.

Winter, G., Griffiths, A. D., Hawkins, R. E. and Hoogenboom, H. R. (1994) Annu Rev Immunol, 12, 433-55.

Wyatt, J. R. 1 Chastain, M. and Puglisi, J. D. (1991) Biotechniques, 11, 764-9.

Yamagishi, J., Kawashima, H., Matsuo, N., Ohue, M., Yamayoshi, M., Fukui, T., Kotani, H., Furuta, R., Nakano, K. and Yamada, M. (1990) Protein Eng, 3, 713-9.

Yelamos, J., Klix, N., Goyenechea, B., Lozano, F., Chui, Y. L., Gonzalez, F. A., Pannell, R., Neuberger, M. S. and Milstein, C. (1995) Nature, 376, 225-9.

Zaccolo, M., Williams, D. M., Brown, D. M. and Gherardi, E. (1996) J Mol Biol, 255, 589-603.

Zakrzewski, S. F. (1980) Preparation of tritiated dihydrofolic acid of high specific activity. Methods Enzymol. pp. 539-.

Zaug, A. J. and Cech, T. R. (1986) Biochemistry, 25, 4478-82.

Zaug, A. J. and Cech, T. R. (1986) Science, 231, 470-5.

Zaug, A. J., Been, M. D. and Cech, T. R. (1986) Nature, 324, 429-33.

Zubay, G. (1973) Annu Rev Genet, 7, 267-87.

Zubay, G. (1980) Methods Enzymol, 65, 856-77.

All publications mentioned in the above specification, and references cited in said publications, are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

The invention claimed is:

1. A method for isolating one or more genetic elements encoding a gene product having a desired activity, comprising the steps of:
provide one or more genetic elements;
compartmentalising the genetic elements into a microcapsule by forming a water-in-fluorocarbon or water-in-perfluorocarbon emulsion microcapsule within a microfluidic device;
expressing the genetic elements to produce their respective gene products within the microcapsules; and
sorting the genetic elements which express gene product(s) having the desired activity; wherein the method is under microfluidic control.

2. A method according to claim 1, wherein the fluorocarbon is perfluorooctyl bromide or perfluorooctylethane.

3. A method according to claim 1, wherein the emulsion is formed using F-alkyl dimorpholinophosphate(s).

4. A method according to claim 3, wherein the F-alkyl dimorpholinophosphate(s) have the general formula $C_nF_{2+1}C_mH_2mOP(O)[N(CH_2CH_2)_2O]_2$.

5. A method according to claim 4 wherein the F-alkyl dimorpholinophosphate is $C_8F_{17}C_{11}H_{22}OP(O)[N(CH_2CH_2)_2O]_2$.

* * * * *

SEQUENCE LISTING

```
<160> NUMBER OF SEQ ID NOS: 12

<210> SEQ ID NO 1
<211> LENGTH: 48
<212> TYPE: DNA
<213> ORGANISM: Artificial
<220> FEATURE:
<223> OTHER INFORMATION: GALBA primer

<400> SEQUENCE: 1
cagactgcac catggccatg attacggatt cactggccgt cgttttac                48

<210> SEQ ID NO 2
<211> LENGTH: 52
<212> TYPE: DNA
<213> ORGANISM: Artificial
<220> FEATURE:
<223> OTHER INFORMATION: GALFO primer

<400> SEQUENCE: 2
acgatgtcag gatccttatt atttttgaca ccagaccaac tggtaatggt ag          52

<210> SEQ ID NO 3
<211> LENGTH: 18
<212> TYPE: DNA
<213> ORGANISM: Artificial
<220> FEATURE:
<223> OTHER INFORMATION: LMB2-10E primer

<400> SEQUENCE: 3
gatggcgccc aacagtcc                                                18

<210> SEQ ID NO 4
<211> LENGTH: 17
<212> TYPE: DNA
<213> ORGANISM: Artificial
<220> FEATURE:
<223> OTHER INFORMATION: PIVB-4 primer

<400> SEQUENCE: 4
tttggccgcc gcccagt                                                 17

<210> SEQ ID NO 5
```

```
<211> LENGTH: 19
<212> TYPE: DNA
<213> ORGANISM: Artificial
<220> FEATURE:
<223> OTHER INFORMATION: LMB2-11E primer

<400> SEQUENCE: 5
gcccgatctt ccccatcgg                                                  19

<210> SEQ ID NO 6
<211> LENGTH: 17
<212> TYPE: DNA
<213> ORGANISM: Artificial
<220> FEATURE:
<223> OTHER INFORMATION: PIVB-8 primer

<400> SEQUENCE: 6
cacacccgtc ctgtgga                                                    17

<210> SEQ ID NO 7
<211> LENGTH: 41
<212> TYPE: DNA
<213> ORGANISM: Artificial
<220> FEATURE:
<223> OTHER INFORMATION: EbgACFw primer

<400> SEQUENCE: 7
cagactgcac cgcgggatga atcgctggga aaacattcag c                         41

<210> SEQ ID NO 8
<211> LENGTH: 39
<212> TYPE: DNA
<213> ORGANISM: Artificial
<220> FEATURE:
<223> OTHER INFORMATION: EbgACBw primer

<400> SEQUENCE: 8
gcgaggagct cttatttgtt atggaaataa ccatcttcg                            39

<210> SEQ ID NO 9
<211> LENGTH: 21
<212> TYPE: DNA
<213> ORGANISM: Artificial
<220> FEATURE:
<223> OTHER INFORMATION: LMB2-9E primer

<400> SEQUENCE: 9
gcatttatca gggttattgt c                                               21

<210> SEQ ID NO 10
<211> LENGTH: 17
<212> TYPE: DNA
<213> ORGANISM: Artificial
<220> FEATURE:
<223> OTHER INFORMATION: PIVB-1 primer

<400> SEQUENCE: 10
gcgttgatgc aatttct                                                    17

<210> SEQ ID NO 11
<211> LENGTH: 18
<212> TYPE: DNA
<213> ORGANISM: Artificial
<220> FEATURE:
<223> OTHER INFORMATION: LMB2-11 primer

<400> SEQUENCE: 11
```

```
atgcgtccgg cgtagagg                                              18

<210> SEQ ID NO 12
<211> LENGTH: 19
<212> TYPE: DNA
<213> ORGANISM: Artificial
<220> FEATURE:
<223> OTHER INFORMATION: PIVB-11

<400> SEQUENCE: 12
agcagccaac tcagcttcc                                             19
```